Figure 1:
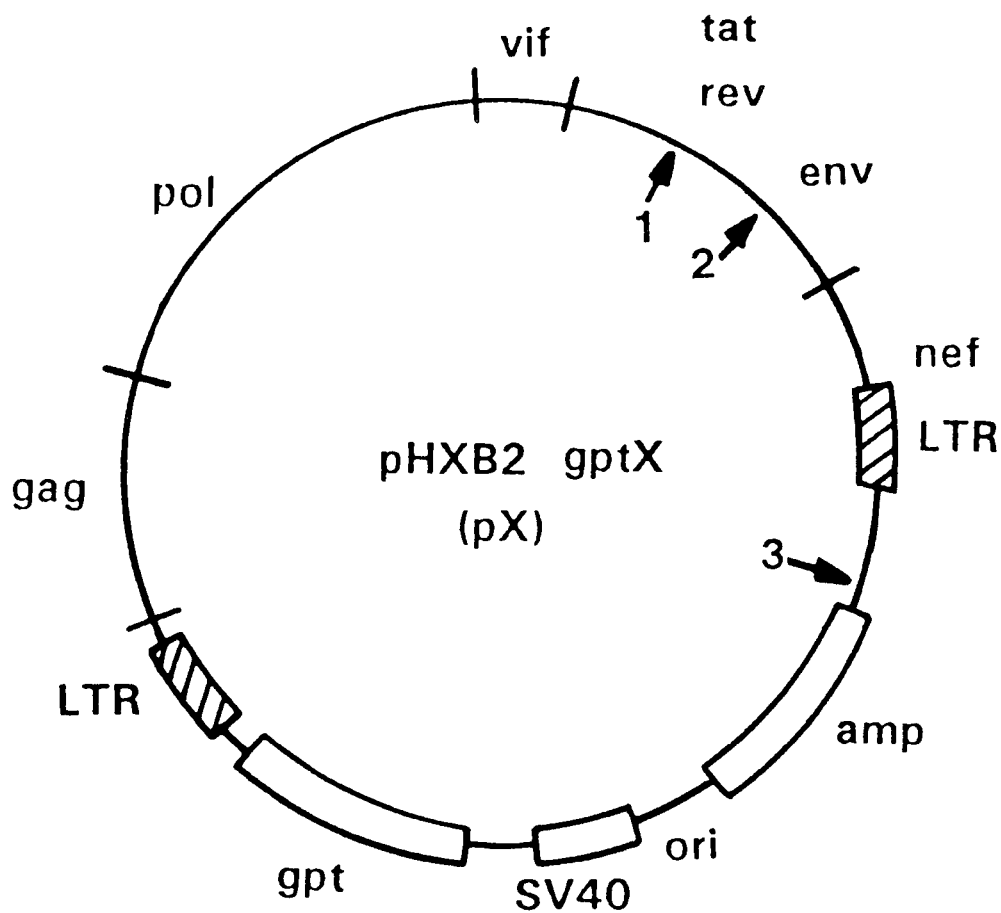

United States Patent [19]
Hu et al.

[11] Patent Number: 6,107,062
[45] Date of Patent: Aug. 22, 2000

[54] ANTISENSE VIRUSES AND ANTISENSE-RIBOZYME VIRUSES

[75] Inventors: Wen Hu; Jie Wang, both of Honolulu, Hi.

[73] Assignee: Inpax, Inc., Honolulu, Hi.

[21] Appl. No.: 07/921,104

[22] Filed: Jul. 30, 1992

[51] Int. Cl.[7] .............................. C12N 15/64; C12N 7/01; C07H 21/04; C07H 21/02

[52] U.S. Cl. ..................................... 435/91.41; 435/235.1; 435/236; 435/320.1; 435/456; 536/23.1; 536/23.72; 536/24.5

[58] Field of Search ................................. 435/69.1, 172.1, 435/235.1, 236, 320.1, 91.4, 91.41, 456; 536/23.1, 24.1, 24.5, 23.72

[56] References Cited

PUBLICATIONS

Rhodes et al. "Inhibition of Human Immunodeficiency Virus Replication in Cell Culture by Endogenously Synthesized Antisense RNA", J. Gen. Virol., vol. 71, 1990, pp. 1965–1974.

von Ruden et al. "Inhibition of Human T–Cell Leukemia Virus Type I Replication in Primary Human T Cells That Express Antisense RNA", J. Virol., Feb. 1989, pp. 677–682.

Lima et al. "Implication of RNA Structure on Antisense Oligonucleotide Hybridization Kinetics", Biochemistry, vol. 31, 1992, pp. 12055–12061.

*Primary Examiner*—David Guzo
*Attorney, Agent, or Firm*—Nixon & Vanderhye P.C.

[57] ABSTRACT

Antisense viruses and antisense ribozyme viruses are disclosed. The novel artificial viruses, their synthesis and their use in preventing and treating viral infections are presented.

11 Claims, 7 Drawing Sheets

SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (iv) ANTI-SENSE: NO (xi) SEQUENCE DESCRIPTION: SEQ ID NO:1:

TCTTCCTGCC ATAGGCAGAA TAGGCGTTAC TCGACAGAG                    39

(2) INFORMATION FOR SEQ ID NO:2:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (iv) ANTI-SENSE: NO (xi) SEQUENCE DESCRIPTION: SEQ ID NO:2:

TGGGTGTCGA CATAGAGATG CCTAAGGCTT TTGTTATG                     38

(2) INFORMATION FOR SEQ ID NO:3:

(i) SEQUENCE CHARACTERISTICS:
      (A) LENGTH: 201 base pairs
      (B) TYPE: nucleic acid
      (C) STRANDEDNESS: double
      (D) TOPOLOGY: linear (iv) ANTI-SENSE: YES (xi) SEQUENCE DESCRIPTION: SEQ ID NO:3:

TGGGTGTCGA CATAGAGATG CCTAAGGCTT TGTTATGAA ACAAACTTGG CAATGAAAGC    60

AACACTTTTT ACAATAGCAA TTGGTACAAG CAGTTTTAGG CTGACTTCCT GGATGCTTCC   120

AGGGCTCTAG TCTAGGATCT ACTGGCTCCA TTTCTTGCTC TCCTCTGTCG AGTAACGCCT   180

ATTCTGCCTA TGGCAGGAAG A                                                     201

(2) INFORMATION FOR SEQ ID NO:4:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (iv) ANTI-SENSE: NO (xi) SEQUENCE DESCRIPTION: SEQ ID NO:4:

TCTTCCTGCC CTAGGCAGAA TAGGCGTTAC TCGACAGAG                                   39

(2) INFORMATION FOR SEQ ID NO:5:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:5:

TGGGTGTCGA CATAGAGATG CCTAAGGCTT TGTTATGAA ACAAACTTGG CAATGAAAGC              60

AACACTTTTT ACAATAGCAA TTGGTACAAG CAGTTTTAGG CTGACTTCCT GGATGCTTCC            120

AGGGCTCTAG TCTAGGATCT ACTGGCTCCA TTTCTTGCTC TCCTCTGTCG AGTAACGCCT            180

ATTCTGCCTA GGGCAGGAAG A                                                     201

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:6:

CTGGAAGCAT CCAGGAAGTT TCGGCCATCA GGCCTCATCA GAGCCTAAAA CTGCTTGTAC             60

(2) INFORMATION FOR SEQ ID NO:7:

(i) SEQUENCE CHARACTERISTICS:
        (A) LENGTH: 222 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:7:

TGGGTGTCGA CATAGAGATG CCTAAGGCTT TGTTATGAA ACAAACTTGG CAATGAAAGC              60

AACACTTTTT ACAATAGCAA TTGGTACAAG CAGTTTTAGG CTCTGATGAG GCCTGATGGC            120

CGAAACTTCC TGGATGCTTC CAGGGCTCTA GTCTAGGATC TACTGGCTCC ATTTCTTGCT            180

CTCCTCTGTC GAGTAACGCC TATTCTGCCT ATGGCAGGAA GA                              222

(2) INFORMATION FOR SEQ ID NO:8:

(i) SEQUENCE CHARACTERISTICS:
        (A) LENGTH: 222 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:8:

TGGGTGTCGA CATAGAGATG CCTAAGGCTT TGTTATGAA ACAAACTTGG CAATGAAAGC              60

AACACTTTTT ACAATAGCAA TTGGTACAAG CAGTTTTAGG CTCTGATGAG GCCTGATGGC            120

CGAAACTTCC TGGATGCTTC CAGGGCTCTA GTCTAGGATC TACTGGCTCC ATTTCTTGCT            180

```
CTCCTCTGTC GAGTAACGCC TATTCTGCCT AGGGCAGGAA GA                           222

(2) INFORMATION FOR SEQ ID NO:9:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (iv) ANTI-SENSE: NO (xi) SEQUENCE DESCRIPTION: SEQ ID NO:9:

CAATGAAAGC AACACTTTTC TGATGAGGCC TGATGGCCTA AACAATAGCA ATTGGTACAA        60

(2) INFORMATION FOR SEQ ID NO:10:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (iv) ANTI-SENSE: NO (xi) SEQUENCE DESCRIPTION: SEQ ID NO:10:

AGGGCTCTAG TCTAGGATCC TGATGAGGCC TGATGGCCGA AACTGGCTC CATTTCTTGCT        60

(2) INFORMATION FOR SEQ ID NO:11:

(i) SEQUENCE CHARACTERISTICS:
         (A) LENGTH: 264 base pairs
         (B) TYPE: nucleic acid
         (C) STRANDEDNESS: double
         (D) TOPOLOGY: linear (iv) ANTI-SENSE: YES (xi) SEQUENCE DESCRIPTION: SEQ ID NO:11:

TGGGTGTCGA CATAGAGATG CCTAAGGCTT TGTTATGAA ACAAACTTGG CAATGAAAGC         60

AACACTTTTC TGATGAGGCC TGATGGCCGA AACAATAGCA ATTGGTACAA GCAGTTTTAG       120

GCTCTGATGA GGCCTGATGG CCGAAACTTC CTGGATGCTT CCAGGGCTCT AGTCTAGGAT       180

CCTGATGAGG CCTGATGGCC GAAACTGGCT CCATTTCTTG CTCTCCTCTG TCGAGTAACG       240

CCTATTCTGC CTATGGCAGG AAGA                                             264

(2) INFORMATION FOR SEQ ID NO:12:

(i) SEQUENCE CHARACTERISTICS:
         (A) LENGTH: 264 base pairs
         (B) TYPE: nucleic acid
         (C) STRANDEDNESS: double
         (D) TOPOLOGY: linear (iv) ANTI-SENSE: YES (xi) SEQUENCE DESCRIPTION: SEQ ID NO:12:

TGGGTGTCGA CATAGAGATG CCTAAGGCTT TGTTATGAA ACAAACTTGG CAATGAAAGC         60

AACACTTTTC TGATGAGGCC TGATGGCCGA AACAATAGCA ATTGGTACAA GCAGTTTTAG       120

GCTCTGATGA GGCCTGATGG CCGAAACTTC CTGGATGCTT CCAGGGCTCT AGTCTAGGAT       180

CCTGATGAGG CCTGATGGCC GAAACTGGCT CCATTTCTTG CTCTCCTCTG TCGAGTAACG       240

CCTATTCTGC CTAGGGCAGG AAGA                                             264
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:13:

GGGCGGGAAT CAAGCAGG                                          18

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:14:

TTGAGAATTC TAACAGCACT ATTCTTTAG                        29

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:15:

CCGAGATCTT CAGACCGGGA GGAGGAGATA TGAGGG              36

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:16:

ATAAGAATTC TGCAACAACT GCTG                                24

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:17:

TTAGATCGAT GATAGCACAC AAGTAGACCC TG                32

(2) INFORMATION FOR SEQ ID NO:18:

(i) SEQUENCE CHARACTERISTICS:
        (A) LENGTH: 27 base pairs (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:18:

CTATGTCGAC ACCCAATTCT GAAATGG                                      27

(2) INFORMATION FOR SEQ ID NO:19:

(i) SEQUENCE CHARACTERISTICS:
            (A) LENGTH: 485 base pairs
            (B) TYPE: nucleic acid
            (C) STRANDEDNESS: double
            (D) TOPOLOGY: linear (iv) ANTI-SENSE: NO (ix) FEATURE:
            (A) NAME/KEY: CDS
            (B) LOCATION: 1..9

(ix) FEATURE:
            (A) NAME/KEY: CDS
            (B) LOCATION: 250..485

(xi) SEQUENCE DESCRIPTION: SEQ ID NO:19:

```
TTA GAT CGA TGATAGCACA CAAGTAGACC CTGACCTAGC AGACCAACTA             49
Leu Asp Arg
  1

ATTCATCTGC ACTATTTTGA TTGTTTTTCA GAATCTGCTA TAAGAAATAC CATATTAGGA  109

CGTATAGTTA GTCCTAGGTG TGAATATCAA GCAGGACATA ACAAGGTAGG ATCTCTACAG  169

TACTTGGCAC TAGCAGCATT AATAAAACCA AAACAGATAA AGCCACCTTT GCCTAGTGTT  229

AGGAAACTGA CAGAGGACAG ATG GAA CAA GCC CCA GAA GAC CAA GGG CCA     279
                         Met Glu Gln Ala Pro Glu Asp Gln Gly Pro
                           1               5                  10

CAG AGG GAG CCA TAC AAT GAA TGG ACA CTA GAG CTT TTA GAG GAA CTT   327
Gln Arg Glu Pro Tyr Asn Glu Trp Thr Leu Glu Leu Leu Glu Glu Leu
             15                  20                  25

AAG AGT GAA GCT GTT AGA CAT TTT CCT AGG ATA TGG CTC CAT AAC TTA   375
Lys Ser Glu Ala Val Arg His Phe Pro Arg Ile Trp Leu His Asn Leu
         30                  35                  40

GGA CAA CAT ATC TAT GAA ACT TAC GGG GAT ACT TGG GCA GGA GTG GAA   423
Gly Gln His Ile Tyr Glu Thr Tyr Gly Asp Thr Trp Ala Gly Val Glu
     45                  50                  55

GCC ATA ATA AGA ATT CTG CAA CAA CTG CTG TTT ATC CAT TTC AGA ATT   471
Ala Ile Ile Arg Ile Leu Gln Gln Leu Leu Phe Ile His Phe Arg Ile
 60                  65                  70

GGG TGT CGA CATAG                                                  485
Gly Cys Arg His
 75
```

(2) INFORMATION FOR SEQ ID NO:20:

(i) SEQUENCE CHARACTERISTICS:
            (A) LENGTH: 576 base pairs
            (B) TYPE: nucleic acid
            (C) STRANDEDNESS: double
            (D) TOPOLOGY: linear (iv) ANTI-SENSE: NO (ix) FEATURE:
            (A) NAME/KEY: CDS
            (B) LOCATION: 1..45

(ix) FEATURE:
          (A) NAME/KEY: CDS
          (B) LOCATION: 286..573

(xi) SEQUENCE DESCRIPTION: SEQ ID NO:20:

```
ATG GGT GCG AGA GCG TCA GTA TTA TGC GGG GGA GAA TTA GAT CGA            45
Met Gly Ala Arg Ala Ser Val Leu Cys Gly Gly Glu Leu Asp Arg
 1               5                  10                  15

TGATAGCACA CAAGTAGACC CTGACCTAGC AGACCAACTA ATTCATCTGC ACTATTTTGA     105

TTGTTTTTCA GAATCTGCTA TAAGAAATAC CATATTAGGA CGTATAGTTA GTCCTAGGTG     165

TGAATATCAA GCAGGACATA ACAAGGTAGG ATCTCTACAG TACTTGGCAC TAGCAGCATT     225

AATAAAACCA AAACAGATAA AGCCACCTTT GCCTAGTGTT AGGAAACTGA CAGAGGACAG     285

ATG GAA CAA GCC CCA GAA GAC CAA GGG CCA CAG AGG GAG CCA TAC AAT       333
Met Glu Gln Ala Pro Glu Asp Gln Gly Pro Gln Arg Glu Pro Tyr Asn
 1               5                  10                  15

GAA TGG ACA CTA GAG CTT TTA GAG GAA CTT AAG AGT GAA GCT GTT AGA       381
Glu Trp Thr Leu Glu Leu Leu Glu Glu Leu Lys Ser Glu Ala Val Arg
            20                  25                  30

CAT TTT CCT AGG ATA TGG CTC CAT AAC TTA GGA CAA CAT ATC TAT GAA       429
His Phe Pro Arg Ile Trp Leu His Asn Leu Gly Gln His Ile Tyr Glu
        35                  40                  45

ACT TAC GGG GAT ACT TGG GCA GGA GTG GAA GCC ATA ATA AGA ATT CTG       477
Thr Tyr Gly Asp Thr Trp Ala Gly Val Glu Ala Ile Ile Arg Ile Leu
    50                  55                  60

CAA CAA CTG CTG TTT ATC CAT TTC AGA ATT GGG TGT CGA CAT AGC AGA       525
Gln Gln Leu Leu Phe Ile His Phe Arg Ile Gly Cys Arg His Ser Arg
65                  70                  75                  80

ATA GGC GTT ACT CGA CAG AGG AGA GCA AGA AAT GGA GCC AGT AGA TCC       573
Ile Gly Val Thr Arg Gln Arg Arg Ala Arg Asn Gly Ala Ser Arg Ser
                85                  90                  95

TAG                                                                    576
```

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:21:

```
CAAGCTTCTC TATCAAAGCA ACCCACCTCC CAACCCCGAG                            40
```

(2) INFORMATION FOR SEQ ID NO:22:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:22:

```
ATAAGAATTC TGCAACAACT GCTGTTTATC CATTTTCAGA ATTGGGTGTC GACATAGCAG      60

AATAGGCGTT ACTCGACAGA GGAGAGCAAG AAATGGAGCC AGTAGATCCT AGACTAGAGC     120

CCTGGAAGCA TCCAGGAAGT CAGCCTAAAA CTGCTTGTAC CAATTGCTAT TGTAAAAAGT     180
```

```
GTTGCTTTCA TTGCCAAGTT TGTTTCATAA CAAAAGCCTT AGGCATCTCC TATGGCAGGA      240

AGAAGCGGAG ACAGCGACGA AGAGCTCATC AGAACAGTCA GACTCATCAA GCTTCTCTAT      300

CAAAGCAACC CACCTCCCAA CCCCGAGGGG ACCCGACAGG CCCGAAGGAA TAGAAGAAGA      360

AGGTGGAGAG AGAGACAGAG ACAGATCCAT TCGATTAGTG AACGGATCCT TGGCACTTAT      420

CTGGGACGAT CTGCGGAGCC TGTGCCTCTT CAGCTACCAC CGCTTGAGAG ACTTACTCTT      480

GATTGTAACG AGGATTGTGG AACTTCTGGG ACGCAGGGGG TGGGAAGCCC TCAAATATTG      540

GTGGAATCTC CTACAGTATT GGAGTCAGGA ACTAAAGAAT AGTGCTGTTA GAATTCTCAA      600
```

(2) INFORMATION FOR SEQ ID NO:23:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (iv) ANTI-SENSE: NO (ix) FEATURE:
        (A) NAME/KEY: CDS
        (B) LOCATION: 13..270

(xi) SEQUENCE DESCRIPTION: SEQ ID NO:23:

```
GTCGGAATTC AC ATG GAA CCT GTG GAC CCA CGT TTG GAA CCA TGG AAA           48
              Met Glu Pro Val Asp Pro Arg Leu Glu Pro Trp Lys
                1               5                  10

CAC CCT GGT TCA CAA CCA AAG ACA GCA TGC ACG AAC TGT TAC TGC AAG         96
His Pro Gly Ser Gln Pro Lys Thr Ala Cys Thr Asn Cys Tyr Cys Lys
         15                  20                  25

AAA TGC TGT TTC CAC TGT CAG GTA TGC TTT ATT ACT AAG GCA CTT GGG        144
Lys Cys Cys Phe His Cys Gln Val Cys Phe Ile Thr Lys Ala Leu Gly
 30                  35                  40

ATT AGT TAC GGA CGT AAA AAA AGA CGT CAA AGG AGG CGT GCA CAC CAA        192
Ile Ser Tyr Gly Arg Lys Lys Arg Gln Arg Arg Arg Ala His Gln
 45                  50                  55                  60

AAT TCA CAA ACA CAC CAG GCA AGC TTG AGT AAA CAG CCG ACG AGT CAG        240
Asn Ser Gln Thr His Gln Ala Ser Leu Ser Lys Gln Pro Thr Ser Gln
                 65                  70                  75

AGT AGG GGC GAT CCT ACT GGG CCC AAA GAG TGACAGAATT CCGAG               285
Ser Arg Gly Asp Pro Thr Gly Pro Lys Glu
             80                  85
```

(2) INFORMATION FOR SEQ ID NO:24:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:24:

```
GTCGGAATTC ACATGGAACC TGTGGACCCA CGTTTGGAAC CATGGAAACA CCCTGGTTCA       60
```

(2) INFORMATION FOR SEQ ID NO:25:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:25:

ACAGCATTTC TTGCAGTAAC AGTTCGTGCA TGCTGTCTTT GGTTGTGAAC CAGGGTGTTT    60

(2) INFORMATION FOR SEQ ID NO:26:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:26:

TGCAAGAAAT GCTGTTTCCA CTGTCAGGTA TGCTTTATTA CTAAGGCACT TGGGATTAGT    60

(2) INFORMATION FOR SEQ ID NO:27:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:27:

ATTTTGGTGT GCACGCCTCC TTTGACGTCT TTTTTTACGT CCGTAACTAA TCCCAAGTGC    60

(2) INFORMATION FOR SEQ ID NO:28:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:28:

CGTGCACACC AAAATTCACA AACACACCAG GCAAGCTTGA GTAAACAGCC GACGAGTCAG    60

(2) INFORMATION FOR SEQ ID NO:29:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:29:

CTCGGAATTC TGTCACTCTT TGGGCCCAGT AGCATCGCCC CTACTCTGAC TCGTCGGCTG    60

(2) INFORMATION FOR SEQ ID NO:30:

(i) SEQUENCE CHARACTERISTICS:
            (A) LENGTH: 375 base pairs
            (B) TYPE: nucleic acid
            (C) STRANDEDNESS: double
            (D) TOPOLOGY: linear (iv) ANTI-SENSE: NO (ix) FEATURE:
            (A) NAME/KEY: CDS (B) LOCATION: 13..360

(xi) SEQUENCE DESCRIPTION: SEQ ID NO:30:

```
GACTGAATTC AT ATG GCT GGT CGT TCG GGT GAT TCG GAT GAG GAA TTG           48
              Met Ala Gly Arg Ser Gly Asp Ser Asp Glu Glu Leu
                1               5                  10

ATA CGT ACT GTG CGT TTG ATA AAA TTA TTG TAC CAG TCG AAT CCT CCG         96
Ile Arg Thr Val Arg Leu Ile Lys Leu Leu Tyr Gln Ser Asn Pro Pro
         15                  20                  25

CCT AAT CCT GAA GGT ACG AGG CAA GCT AGG CGT AAC CGT CGA CGG CGC        144
Pro Asn Pro Glu Gly Thr Arg Gln Ala Arg Arg Asn Arg Arg Arg Arg
 30                  35                  40

TGG CGT GAA CGT CAA CGT CAA ATA CAC AGC ATC TCA GAG AGA ATA TTA        192
Trp Arg Glu Arg Gln Arg Gln Ile His Ser Ile Ser Glu Arg Ile Leu
 45                  50                  55                  60

GGG ACA TAC TTA GGT AGG AGC GCC GAA CCA GTC CCA TTA CAA TTG CCT        240
Gly Thr Tyr Leu Gly Arg Ser Ala Glu Pro Val Pro Leu Gln Leu Pro
             65                  70                  75

CCT TTG GAA CGT TTG ACA TTA GAC TGC AAT GAA GAC TGC GGT ACA AGC        288
Pro Leu Glu Arg Leu Thr Leu Asp Cys Asn Glu Asp Cys Gly Thr Ser
         80                  85                  90

GGT ACC CAA GGT GTC GGT TCG CCA CAG ATC CTA GTC GAG AGC CCA ACT        336
Gly Thr Gln Gly Val Gly Ser Pro Gln Ile Leu Val Glu Ser Pro Thr
 95                  100                 105

GTT CTT GAA AGT GGT ACA AAG GAG TGATCGAATT CCGTC                       375
Val Leu Glu Ser Gly Thr Lys Glu
    110                 115
```

(2) INFORMATION FOR SEQ ID NO:31:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:31:

```
GACTGAATTC ATATGGCTGG TCGTTCGGGT GATTCGGATG AGGAATTGAT ACGTACTGTG      60

CGT                                                                   63
```

(2) INFORMATION FOR SEQ ID NO:32:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:32:

```
ACCTTCAGGA TTAGGCGGAG GATTCGACTG GTACAATAAT TTTATCAAAC GCACAGTACG      60

TAT                                                                   63
```

(2) INFORMATION FOR SEQ ID NO:33:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:33:

CCTAATCCTG AAGGTACGAG GCAAGCTAGG CGTAACCGTC GACGGCGCTG GCGTGAACGT    60

CAA                                                                 63

(2) INFORMATION FOR SEQ ID NO:34:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:34:

ACCTAAGTAT GTCCCTAATA TTCTCTCTGA GATGCTGTGT ATTTGACGTT GACGTTCACG    60

CCA                                                                 63

(2) INFORMATION FOR SEQ ID NO:35:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:35:

GGGACATACT TAGGTAGGAG CGCCGAACCA GTCCCATTAC AATTGCCTCC TTTGGAACGT    60

TTG                                                                 63

(2) INFORMATION FOR SEQ ID NO:36:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:36:

GACACCTTGG GTACCGCTTG TACCGCAGTC TTCATTGCAG TCTAATGTCA AACGTTCCAA    60

AGG                                                                 63

(2) INFORMATION FOR SEQ ID NO:37:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:37:

GGTACCCAAG GTGTCGGTTC GCCACAGATC CTAGTCGAGA GCCCAACTGT TCTTGAAAGT    60

GGT                                                                 63

(2) INFORMATION FOR SEQ ID NO:38:

```
        (i) SEQUENCE CHARACTERISTICS:
            (A) LENGTH: 39 base pairs
            (B) TYPE: nucleic acid
            (C) STRANDEDNESS: single
            (D) TOPOLOGY: linear (iv) ANTI-SENSE: NO (xi) SEQUENCE DESCRIPTION: SEQ ID NO:38:

GACGGAATTC GAGCACTCCT TTGTACCACT TTCAAGAAC                           39

(2) INFORMATION FOR SEQ ID NO:39:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (iii) HYPOTHETICAL: YES (iv) ANTI-SENSE: NO (xi) SEQUENCE DESCRIPTION: SEQ ID NO:39:

ACGGTACGTA A                                                        11

(2) INFORMATION FOR SEQ ID NO:40:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (iii) HYPOTHETICAL: YES (iv) ANTI-SENSE: YES (xi) SEQUENCE DESCRIPTION: SEQ ID NO:40:

TTACGTACCG T                                                        11

(2) INFORMATION FOR SEQ ID NO:41:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:41:

ACGGUACGUA A                                                        11

(2) INFORMATION FOR SEQ ID NO:42:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (iii) HYPOTHETICAL: YES (iv) ANTI-SENSE: YES (xi) SEQUENCE DESCRIPTION: SEQ ID NO:42:

UUACGUACCG U                                                        11
```

(2) INFORMATION FOR SEQ ID NO:43:

(i) SEQUENCE CHARACTERISTICS:
       (A) LENGTH: 213 base pairs
       (B) TYPE: nucleic acid
       (C) STRANDEDNESS: double
       (D) TOPOLOGY: linear (iii) HYPOTHETICAL: NO (iv) ANTI-SENSE: NO (vii) IMMEDIATE SOURCE:
       (A) LIBRARY: GenBank
       (B) CLONE: HXB2 LOCUS HIVHXB2CG, 9718 bp, VRL 25-SEP-1987

(viii) POSITION IN GENOME:
       (B) MAP POSITION: 5774-5986

(ix) FEATURE:
       (A) NAME/KEY:  beginning of tat-1 and rev-1 gene, two splice
           acceptor
           sites, Sal-I and EcoNI sites
       (B) LOCATION:  splice acceptors at 5776G/5777A and
           5975G/5976G, Sal-I at 5785 and EcoNI at 5966

(xi) SEQUENCE DESCRIPTION: SEQ ID NO:43:

CAGAATTGGG TGTCGACATA GCAGAATAGG CGTTACTCGA CAGAGGAGAG CAAGAAATGG     60

AGCCAGTAGA TCCTAGACTA GAGCCCTGGA AGCATCCAGG AAGTCAGCCT AAAACTGCTT    120

GTACCAATTG CTATTGTAAA AAGTGTTGCT TTCATTGCCA AGTTTGTTTC ATAACAAAAG    180

CCTTAGGCAT CTCCTATGGC AGGAAGAAGC GGA                                 213

(2) INFORMATION FOR SEQ ID NO:44:

(i) SEQUENCE CHARACTERISTICS:
       (A) LENGTH: 46 base pairs
       (B) TYPE: nucleic acid
       (C) STRANDEDNESS: single
       (D) TOPOLOGY: unknown (iii) HYPOTHETICAL: NO (iv) ANTI-SENSE: NO (x) PUBLICATION INFORMATION:
       (A) AUTHORS: 3 articles: Cech, Uhlenbeck OC, Forster et al.
       (C) JOURNAL:  respectively: Science, Nature(London), Cell
       (E) ISSUE: respectively: 236, 328, 49
       (F) PAGES: respectively: 1532-9, 596-600, 211-220
       (G) DATE: respectively 1987, 1987, 1987

(xi) SEQUENCE DESCRIPTION: SEQ ID NO:44:

GAAACNNNNN NGUHNNNNNN NNNNNNCUGA NNNNNNNNNN NNNNGA                    46

(2) INFORMATION FOR SEQ ID NO:45:

(i) SEQUENCE CHARACTERISTICS:
       (A) LENGTH: 213 base pairs
       (B) TYPE: nucleic acid
       (C) STRANDEDNESS: single
       (D) TOPOLOGY: linear (iii) HYPOTHETICAL: NO (iv) ANTI-SENSE: NO (vii) IMMEDIATE SOURCE:
       (A) LIBRARY: GenBank
       (B) CLONE: HXB2 LOCUS HIVHXB2CG, 9718 bp, VRL 25-SEP-1987

-continued

```
    (viii) POSITION IN GENOME:
          (B) MAP POSITION: 5774-5986

(xi) SEQUENCE DESCRIPTION: SEQ ID NO:45:

CAGAAUUGGG UGUCGACAUA GCAGAAUAGG CGUUACUCGA CAGAGGAGAG CAAGAAAUGG      60

AGCCAGUAGA UCCUAGACUA GAGCCCUGGA AGCAUCCAGG AAGUCAGCCU AAAACUGCUU     120

GUACCAAUUG CUAUUGUAAA AAGUGUUGCU UUCAUUGCCA AGUUUGUUUC AUAACAAAAG     180

CCUUAGGCAU CUCCUAUGGC AGGAAGAAGC GGA                                 213

(2) INFORMATION FOR SEQ ID NO:46:

(i) SEQUENCE CHARACTERISTICS:
          (A) LENGTH: 213 base pairs
          (B) TYPE: nucleic acid
          (C) STRANDEDNESS: double
          (D) TOPOLOGY: linear (iv) ANTI-SENSE: YES (xi) SEQUENCE DESCRIPTION: SEQ ID NO:46:

CAGAATTGGG TGTCGACATA GAGATGCCTA AGGCTTTTGT TATGAAACAA ACTTGGCAAT      60

GAAAGCAACA CTTTTTACAA TAGCAATTGG TACAAGCAGT TTTAGGCTGA CTTCCTGGAT     120

GCTTCCAGGG CTCTAGTCTA GGATCTACTG GCTCCATTTC TTGCTCTCCT CTGTCGAGTA     180

ACGCCTATTC TGCCTATGGC AGGAAGAAGC GGA                                 213

(2) INFORMATION FOR SEQ ID NO:47:

(i) SEQUENCE CHARACTERISTICS:
          (A) LENGTH: 213 base pairs
          (B) TYPE: nucleic acid
          (C) STRANDEDNESS: single
          (D) TOPOLOGY: linear (iii) HYPOTHETICAL: NO (iv) ANTI-SENSE: YES (vii) IMMEDIATE SOURCE:
          (A) LIBRARY: GenBank
          (B) CLONE: HXB2 LOCUS HIVHXB2CG, 9718 bp, VRL 25-SEP-1987

(viii) POSITION IN GENOME:
          (B) MAP POSITION: 5774-5986

(xi) SEQUENCE DESCRIPTION: SEQ ID NO:47:

CAGAAUUGGG UGUCGACAUA GAGAUGCCUA AGGCUUUUGU UAUGAAACAA ACUUGGCAAU      60

GAAAGCAACA CUUUUUACAA UAGCAAUUGG UACAAGCAGU UUUAGGCUGA CUUCCUGGAU     120

GCUUCCAGGG CUCUAGUCUA GGAUCUACUG GCUCCAUUUC UUGCUCUCCU CUGUCGAGUA     180

ACGCCUAUUC UGCCUAUGGC AGGAAGAAGC GGA                                 213

(2) INFORMATION FOR SEQ ID NO:48:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (iii) HYPOTHETICAL: NO (iv) ANTI-SENSE: NO (xi) SEQUENCE DESCRIPTION: SEQ ID NO:48:
```

```
CUGAUGAGGC CUGAUGGCCG AA                                              22

(2) INFORMATION FOR SEQ ID NO:49:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (iii) HYPOTHETICAL: NO (iv) ANTI-SENSE: NO (vii) IMMEDIATE SOURCE:
         (A) LIBRARY: GenBank
         (B) CLONE: HXB2 LOCUS HIVHXB2CG, 9718 bp, VRL 25-SEP-1987

(viii) POSITION IN GENOME:
         (B) MAP POSITION: 5962-5980

(xi) SEQUENCE DESCRIPTION: SEQ ID NO:49:

ATCTCCTATG GCAGGAAGA                                                  19

(2) INFORMATION FOR SEQ ID NO:50:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (iv) ANTI-SENSE: NO (xi) SEQUENCE DESCRIPTION: SEQ ID NO:50:

ATCTCCTAGG GCAGGAAGA                                                  19

(2) INFORMATION FOR SEQ ID NO:51:

(i) SEQUENCE CHARACTERISTICS:
         (A) LENGTH: 171 base pairs
         (B) TYPE: nucleic acid
         (C) STRANDEDNESS: double
         (D) TOPOLOGY: linear (iv) ANTI-SENSE: YES (xi) SEQUENCE DESCRIPTION: SEQ ID NO:51:

AGATGCCTAA GGCTTTTGTT ATGAAACAAA CTTGGCAATG AAAGCAACAC TTTTTACAAT      60

AGCAATTGGT ACAAGCAGTT TTAGGCTGAC TTCCTGGATG CTTCCAGGGC TCTAGTCTAG     120

GATCTACTGG CTCCATTTCT TGCTCTCCTC TGTCGAGTAA CGCCTATTCT G             171

(2) INFORMATION FOR SEQ ID NO:52:

(i) SEQUENCE CHARACTERISTICS:
         (A) LENGTH: 280 base pairs
         (B) TYPE: nucleic acid
         (C) STRANDEDNESS: double
         (D) TOPOLOGY: linear (iv) ANTI-SENSE: YES (xi) SEQUENCE DESCRIPTION: SEQ ID NO:52:

TGGGTGTCGA CATAGAGATG CCTAAGGCTT TGTTATGAA ACAAACTTGG CAATGAAAGC      60

AACACTTTTT ACAATAGCAA TTGGTACAAG CAGTTTTAGG CTGACTTCCT GGATGCTTCC    120

AGGGCTCTAG TCTAGGATCT ACTGGCTCCA TTTCTTGCTC TCCTCTGTCG AGTAACGCCT    180
```

| ATTCTGCCTA TGGCAGGAAG AAGCGGAGAC AGCGACGAAG AGCTCATCAG AACAGTCAGA | 240 |
| CTCATCAAGC TTCTCTATCA AAGCAGTAAG TAGTACATGT | 280 |

(2) INFORMATION FOR SEQ ID NO:53:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:53:

| CAGAAUUGGG UGUCGACAUA GAGAUGCCUA AGGCUUUUGU UAUGAAACAA ACUUGGCAAU | 60 |
| GAAAGCAACA CUUUUUACAA UAGCAAUUGG UACAAGCAGU UUUAGGCUCU GAUGAGGCCU | 120 |
| GAUGGCCGAA ACUUCCUGGA UGCUUCCAGG GCUCUAGUCU AGGAUCUACU GGCUCCAUUU | 180 |
| CUUGCUCUCC UCUGUCGAGU AACGCCUAUU CUGCCUAUGG CAGGAAGAAG CGGA | 234 |

(2) INFORMATION FOR SEQ ID NO:54:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (iv) ANTI-SENSE: NO (xi) SEQUENCE DESCRIPTION: SEQ ID NO:54:

| CAGAAUUGGG UGUCGACAUA GCAGAAUAGG CGUUACUCGA CAGAGGAGAG CAAGAAAUGG | 60 |
| AGCCAGUAGA UCCUAGACUA GAGCCCUGGA AGCAUCCAGG AAGUCAGCCU AAAACUGCUU | 120 |
| GUACCAAUUG CUAUUGUAAA AAGUGUUGCU UUCAUUGCCA AGUUUGUUUC AUAACAAAAG | 180 |
| CCUUAGGCAU CUCCUAUGGC AGGAAGAAGC GGA | 213 |

(2) INFORMATION FOR SEQ ID NO:55:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:55:

| CAGAATTGGG TGTCGACATA GAGATGCCTA AGGCTTTTGT TATGAAACAA ACTTGGCAAT | 60 |
| GAAAGCAACA CTTTTTACAA TAGCAATTGG TACAAGCAGT TTTAGGCTCT GATGAGGCCT | 120 |
| GATGGCCGAA ACTTCCTGGA TGCTTCCAGG GCTCTAGTCT AGGATCTACT GGCTCCATTT | 180 |
| CTTGCTCTCC TCTGTCGAGT AACGCCTATT CTGCCTATGG CAGGAAGAAG CGGA | 234 |

(2) INFORMATION FOR SEQ ID NO:56:

(i) SEQUENCE CHARACTERISTICS:
        (A) LENGTH: 276 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:56:

```
CAGAAUUGGG UGUCGACAUA GAGAUGCCUA AGGCUUUUGU UAUGAAACAA ACUUGGCAAU      60

GAAAGCAACA CUUUUCUGAU GAGGCCUGAU GGCCGAAACA AUAGCAAUUG GUACAAGCAG     120

UUUUAGGCUC UGAUGAGGCC UGAUGGCCGA AACUUCCUGG AUGCUUCCAG GGCUCUAGUC     180

UAGGAUCCUG AUGAGGCCUG AUGGCCGAAA CUGGCUCCAU UUCUUGCUCU CCUCUGUCGA     240

GUAACGCCUA UUCUGCCUAU GGCAGGAAGA AGCGGA                               276

(2) INFORMATION FOR SEQ ID NO:57:

(i) SEQUENCE CHARACTERISTICS:
        (A) LENGTH: 276 base pairs
        (B) TYPE: nucleic acid
        (C) STRANDEDNESS: double
        (D) TOPOLOGY: linear (iv) ANTI-SENSE: YES (xi) SEQUENCE DESCRIPTION: SEQ ID NO:57:

CAGAATTGGG TGTCGACATA GAGATGCCTA AGGCTTTTGT TATGAAACAA ACTTGGCAAT      60

GAAAGCAACA CTTTTCTGAT GAGGCCTGAT GGCCGAAACA ATAGCAATTG GTACAAGCAG     120

TTTTAGGCTC TGATGAGGCC TGATGGCCGA AACTTCCTGG ATGCTTCCAG GCTCTAGTC      180

TAGGATCCTG ATGAGGCCTG ATGGCCGAAA CTGGCTCCAT TTCTTGCTCT CCTCTGTCGA    240

GTAACGCCTA TTCTGCCTAT GGCAGGAAGA AGCGGA                               276

(2) INFORMATION FOR SEQ ID NO:58:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (iii) HYPOTHETICAL: NO (iv) ANTI-SENSE: NO (ix) FEATURE:
        (A) NAME/KEY: CDS
        (B) LOCATION: 1..42

(xi) SEQUENCE DESCRIPTION: SEQ ID NO:58:

GAG TCC GAG ATC TTC AGA CCT GGA GGA GGA GAT ATG AGG GAC               42
Glu Ser Glu Ile Phe Arg Pro Gly Gly Gly Asp Met Arg Asp
  1               5                  10

(2) INFORMATION FOR SEQ ID NO:59:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (iv) ANTI-SENSE: NO (ix) FEATURE:
        (A) NAME/KEY: CDS
        (B) LOCATION: 1..42

(xi) SEQUENCE DESCRIPTION: SEQ ID NO:59:

GAG TCC GAG ATC TTC AGA CCG GGA GGA GGA GAT ATG AGG GAC               42
Glu Ser Glu Ile Phe Arg Pro Gly Gly Gly Asp Met Arg Asp
  1               5                  10
```

(2) INFORMATION FOR SEQ ID NO:60:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (iii) HYPOTHETICAL: NO (iv) ANTI-SENSE: NO (vii) IMMEDIATE SOURCE:
        (A) LIBRARY: GenBank
        (B) CLONE: HXB2 LOCUS HIVHXB2CG, 9718 bp, VRL 25-SEP-1987

(viii) POSITION IN GENOME:
        (B) MAP POSITION: 789

(xi) SEQUENCE DESCRIPTION: SEQ ID NO:60:

ATGGGTGCGA GAGCGTCAGT ATTATGCGGG GGAGAATTAG ATCGATGGGA AAAA      54

(2) INFORMATION FOR SEQ ID NO:61:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (iii) HYPOTHETICAL: NO (iv) ANTI-SENSE: NO (vii) IMMEDIATE SOURCE:
        (A) LIBRARY: GenBank
        (B) CLONE: HXB2 LOCUS HIVHXB2CG, 9718 bp, VRL 25-SEP-1987

(viii) POSITION IN GENOME:
        (B) MAP POSITION: 5388/5389

(xi) SEQUENCE DESCRIPTION: SEQ ID NO:61:

AGATATAGCA CACAAGTAGA CCCTGAACTA GCAGACCAAC TAATTCATCT GTAT      54

(2) INFORMATION FOR SEQ ID NO:62:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (iii) HYPOTHETICAL: NO (iv) ANTI-SENSE: NO (xi) SEQUENCE DESCRIPTION: SEQ ID NO:62:

ATGGGTGCGA GAGCGTCGGT ATTATGCGGG GGAGAATTAG ATAAATGGGA AAAA      54

(2) INFORMATION FOR SEQ ID NO:63:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (iii) HYPOTHETICAL: NO (iv) ANTI-SENSE: NO (xi) SEQUENCE DESCRIPTION: SEQ ID NO:63:

AGATATAGCA CACAAGTAGA CCCTGACCTA GCAGACCAAC TAATTCATCT GTAT          54

(2) INFORMATION FOR SEQ ID NO:64:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (iii) HYPOTHETICAL: NO (iv) ANTI-SENSE: NO (vii) IMMEDIATE SOURCE:
        (A) LIBRARY: GenBank
        (B) CLONE: HXB2 LOCUS HIVHXB2CG, 9718 bp, VRL 25-SEP-1987

(viii) POSITION IN GENOME:
        (B) MAP POSITION: 5767-5794

(xi) SEQUENCE DESCRIPTION: SEQ ID NO:64:

CCATTTTCAG AATTGGGTGT CGACATAG          28

(2) INFORMATION FOR SEQ ID NO:65:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (iii) HYPOTHETICAL: NO (iv) ANTI-SENSE: NO (xi) SEQUENCE DESCRIPTION: SEQ ID NO:65:

CCATTTCAGA ATTGGGTGTC GACATAG          27

(2) INFORMATION FOR SEQ ID NO:66:

(i) SEQUENCE CHARACTERISTICS:
        (A) LENGTH: 310 base pairs
        (B) TYPE: nucleic acid
        (C) STRANDEDNESS: double
        (D) TOPOLOGY: linear (iii) HYPOTHETICAL: NO (iv) ANTI-SENSE: NO (vii) IMMEDIATE SOURCE:
        (A) LIBRARY: GenBank
        (B) CLONE: HXB2 LOCUS HIVHXB2CG, 9718 bp, VRL 25-SEP-1987

(viii) POSITION IN GENOME:
        (B) MAP POSITION: 5704-6044

(xi) SEQUENCE DESCRIPTION: SEQ ID NO:66:

ATAATAAGAA TTCTGCAACA ACTGCTGTTT ATCCATTTTC AGAATTGGGT GTCGACATAG          60

CAGAATAGGC GTTACTCGAC AGAGGAGAGC AAGAAATGGA GCCAGTAGAT CCTAGACTAG          120

AGCCCTGGAA GCATCCAGGA AGTCAGCCTA AAACTGCTTG TACCAATTGC TATTGTAAAA          180

AGTGTTGCTT TCATTGCCAA GTTTGTTTCA TAACAAAAGC CTTAGGCATC TCCTATGGCA          240

GGAAGAAGCG GAGACAGCGA CGAAGAGCTC ATCAGAACAG TCAGACTCAT CAAGCTTCTC          300

TATCAAAGCA          310

(2) INFORMATION FOR SEQ ID NO:67:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (iii) HYPOTHETICAL: NO (iv) ANTI-SENSE: NO (vii) IMMEDIATE SOURCE:
        (A) LIBRARY: GenBank
        (B) CLONE: HXB2 LOCUS HIVHXB2CG, 9718 bp, VRL 25-SEP-1987

(viii) POSITION IN GENOME:
        (B) MAP POSITION: 8377-8680

(xi) SEQUENCE DESCRIPTION: SEQ ID NO:67:

ACCCACCTCC CAACCCCGAG GGGACCCGAC AGGCCCGAAG GAATAGAAGA AGAAGGTGGA      60

GAGAGAGACA GAGACAGATC CATTCGATTA GTGAACGGAT CCTTGGCACT TATCTGGGAC     120

GATCTGCGGA GCCTGTGCCT CTTCAGCTAC CACCGCTTGA GAGACTTACT CTTGATTGTA     180

ACGAGGATTG TGGAACTTCT GGGACGCAGG GGGTGGGAAG CCCTCAAATA TTGGTGGAAT     240

CTCCTACAGT ATTGGAGTCA GGAACTAAAG AATAGTGCTG TTAGCTTGCT CAATGCCACA     300

GCC                                                                   303

(2) INFORMATION FOR SEQ ID NO:68:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (iii) HYPOTHETICAL: NO (iv) ANTI-SENSE: NO (ix) FEATURE:
        (A) NAME/KEY: CDS
        (B) LOCATION: 1..258

(xi) SEQUENCE DESCRIPTION: SEQ ID NO:68:

ATG GAG CCA GTA GAT CCT AGA CTA GAG CCC TGG AAG CAT CCA GGA AGT       48
Met Glu Pro Val Asp Pro Arg Leu Glu Pro Trp Lys His Pro Gly Ser
  1               5                  10                  15

CAG CCT AAA ACT GCT TGT ACC AAT TGC TAT TGT AAA AAG TGT TGC TTT       96
Gln Pro Lys Thr Ala Cys Thr Asn Cys Tyr Cys Lys Lys Cys Cys Phe
             20                  25                  30

CAT TGC CAA GTT TGT TTC ATA ACA AAA GCC TTA GGC ATC TCC TAT GGC      144
His Cys Gln Val Cys Phe Ile Thr Lys Ala Leu Gly Ile Ser Tyr Gly
         35                  40                  45

AGG AAG AAG CGG AGA CAG CGA CGA AGA GCT CAT CAG AAC AGT CAG ACT      192
Arg Lys Lys Arg Arg Gln Arg Arg Ala His Gln Asn Ser Gln Thr
     50                  55                  60

CAT CAA GCT TCT CTA TCA AAG CAA CCC ACC TCC CAA TCC CGA GGG GAC      240
His Gln Ala Ser Leu Ser Lys Gln Pro Thr Ser Gln Ser Arg Gly Asp
 65                  70                  75                  80

CCG ACA GGC CCG AAG GAA TAG                                          261
Pro Thr Gly Pro Lys Glu
                 85

(2) INFORMATION FOR SEQ ID NO:69:

(i) SEQUENCE CHARACTERISTICS:

(A) LENGTH: 261 base pairs
        (B) TYPE: nucleic acid
        (C) STRANDEDNESS: double
        (D) TOPOLOGY: linear (iv) ANTI-SENSE: NO (ix) FEATURE:
        (A) NAME/KEY: CDS
        (B) LOCATION: 1..258

(xi) SEQUENCE DESCRIPTION: SEQ ID NO:69:

```
ATG GAA CCT GTG GAC CCA CGT TTG GAA CCA TGG AAA CAC CCT GGT TCA      48
Met Glu Pro Val Asp Pro Arg Leu Glu Pro Trp Lys His Pro Gly Ser
 1               5                  10                  15

CAA CCA AAG ACA GCA TGC ACG AAC TGT TAC TGC AAG AAA TGC TGT TTC      96
Gln Pro Lys Thr Ala Cys Thr Asn Cys Tyr Cys Lys Lys Cys Cys Phe
            20                  25                  30

CAC TGT CAG GTA TGC TTT ATT ACT AAG GCA CTT GGG ATT AGT TAC GGA     144
His Cys Gln Val Cys Phe Ile Thr Lys Ala Leu Gly Ile Ser Tyr Gly
        35                  40                  45

CGT AAA AAA AGA CGT CAA AGG AGG CGT GCA CAC CAA AAT TCA CAA ACA     192
Arg Lys Lys Arg Arg Gln Arg Arg Ala His Gln Asn Ser Gln Thr
 50                  55                  60

CAC CAG GCA AGC TTG AGT AAA CAG CCG ACG AGT CAG AGT AGG GGC GAT     240
His Gln Ala Ser Leu Ser Lys Gln Pro Thr Ser Gln Ser Arg Gly Asp
 65                  70                  75                  80

CCT ACT GGG CCC AAA GAG TGA                                         261
Pro Thr Gly Pro Lys Glu
             85
```

(2) INFORMATION FOR SEQ ID NO:70:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (iii) HYPOTHETICAL: NO (iv) ANTI-SENSE: NO (ix) FEATURE:
        (A) NAME/KEY: CDS
        (B) LOCATION: 1..348

(xi) SEQUENCE DESCRIPTION: SEQ ID NO:70:

```
ATG GCA GGA AGA AGC GGA GAC AGC GAC GAA GAG CTC ATC AGA ACA GTC      48
Met Ala Gly Arg Ser Gly Asp Ser Asp Glu Glu Leu Ile Arg Thr Val
 1               5                  10                  15

AGA CTC ATC AAG CTT CTC TAT CAA AGC AAC CCA CCT CCC AAC CCC GAG      96
Arg Leu Ile Lys Leu Leu Tyr Gln Ser Asn Pro Pro Pro Asn Pro Glu
            20                  25                  30

GGG ACC CGA CAG GCC CGA AGG AAT AGA AGA AGA AGG TGG AGA GAG AGA     144
Gly Thr Arg Gln Ala Arg Arg Asn Arg Arg Arg Arg Trp Arg Glu Arg
        35                  40                  45

CAG AGA CAG ATC CAT TCG ATT AGT GAA CGG ATC CTT GGC ACT TAT CTG     192
Gln Arg Gln Ile His Ser Ile Ser Glu Arg Ile Leu Gly Thr Tyr Leu
 50                  55                  60

GGA CGA TCT GCG GAG CCT GTG CCT CTT CAG CTA CCA CCG CTT GAG AGA     240
Gly Arg Ser Ala Glu Pro Val Pro Leu Gln Leu Pro Pro Leu Glu Arg
 65                  70                  75                  80

CTT ACT CTT GAT TGT AAC GAG GAT TGT GGA ACT TCT GGG ACG CAG GGG     288
Leu Thr Leu Asp Cys Asn Glu Asp Cys Gly Thr Ser Gly Thr Gln Gly
             85                  90                  95
```

```
GTG GGA AGC CCT CAA ATA TTG GTG GAA TCT CCT ACA GTA TTG GAG TCA      336
Val Gly Ser Pro Gln Ile Leu Val Glu Ser Pro Thr Val Leu Glu Ser
            100                 105                 110

GGA ACT AAA GAA TAG                                                  351
Gly Thr Lys Glu
        115

(2) INFORMATION FOR SEQ ID NO:71:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (iii) HYPOTHETICAL: NO (iv) ANTI-SENSE: NO (ix) FEATURE:
        (A) NAME/KEY: CDS
        (B) LOCATION: 1..348

(xi) SEQUENCE DESCRIPTION: SEQ ID NO:71:

ATG GCT GGT CGT TCG GGT GAT TCG GAT GAG GAA TTG ATA CGT ACT GTG       48
Met Ala Gly Arg Ser Gly Asp Ser Asp Glu Glu Leu Ile Arg Thr Val
 1               5                  10                  15

CGT TTG ATA AAA TTA TTG TAC CAG TCG AAT CCT CCG CCT AAT CCT GAA       96
Arg Leu Ile Lys Leu Leu Tyr Gln Ser Asn Pro Pro Pro Asn Pro Glu
                20                  25                  30

GGT ACG AGG CAA GCT AGG CGT AAC CGT CGA CGG CGC TGG CGT GAA CGT      144
Gly Thr Arg Gln Ala Arg Arg Asn Arg Arg Arg Arg Trp Arg Glu Arg
            35                  40                  45

CAA CGT CAA ATA CAC AGC ATC TCA GAG AGA ATA TTA GGG ACA TAC TTA      192
Gln Arg Gln Ile His Ser Ile Ser Glu Arg Ile Leu Gly Thr Tyr Leu
 50                  55                  60

GGT AGG AGC GCC GAA CCA GTC CCA TTA CAA TTG CCT CCT TTG GAA CGT      240
Gly Arg Ser Ala Glu Pro Val Pro Leu Gln Leu Pro Pro Leu Glu Arg
 65                  70                  75                  80

TTG ACA TTA GAC TGC AAT GAA GAC TGC GGT ACA AGC GGT ACC CAA GGT      288
Leu Thr Leu Asp Cys Asn Glu Asp Cys Gly Thr Ser Gly Thr Gln Gly
                85                  90                  95

GTC GGT TCG CCA CAG ATC CTA GTC GAG AGC CCA ACT GTT CTT GAA AGT      336
Val Gly Ser Pro Gln Ile Leu Val Glu Ser Pro Thr Val Leu Glu Ser
            100                 105                 110

GGT ACA AAG GAG TGA                                                  351
Gly Thr Lys Glu
        115

(2) INFORMATION FOR SEQ ID NO:72:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (iv) ANTI-SENSE: NO (ix) FEATURE:
        (A) NAME/KEY: CDS
        (B) LOCATION: 93..350

(xi) SEQUENCE DESCRIPTION: SEQ ID NO:72:

ATAAGAATTC TGCAACAACT GCTGTTTATC CATTTTCAGA ATTGGGTGTC GACATAGCAG     60
```

```
AATAGGCGTT ACTCGACAGA GGAGAGCAAG AA ATG GAG CCA GTA GAT CCT AGA        113
                                    Met Glu Pro Val Asp Pro Arg
                                     1               5

CTA GAG CCC TGG AAG CAT CCA GGA AGT CAG CCT AAA ACT GCT TGT ACC        161
Leu Glu Pro Trp Lys His Pro Gly Ser Gln Pro Lys Thr Ala Cys Thr
        10                  15                  20

AAT TGC TAT TGT AAA AAG TGT TGC TTT CAT TGC CAA GTT TGT TTC ATA        209
Asn Cys Tyr Cys Lys Lys Cys Cys Phe His Cys Gln Val Cys Phe Ile
 25                  30                  35

ACA AAA GCC TTA GGC ATC TCC TAT GGC AGG AAG AAG CGG AGA CAG CGA        257
Thr Lys Ala Leu Gly Ile Ser Tyr Gly Arg Lys Lys Arg Arg Gln Arg
 40                  45                  50                  55

CGA AGA GCT CAT CAG AAC AGT CAG ACT CAT CAA GCT TCT CTA TCA AAG        305
Arg Arg Ala His Gln Asn Ser Gln Thr His Gln Ala Ser Leu Ser Lys
                 60                  65                  70

CAA CCC ACC TCC CAA CCC CGA GGG GAC CCG ACA GGC CCG AAG GAA            350
Gln Pro Thr Ser Gln Pro Arg Gly Asp Pro Thr Gly Pro Lys Glu
             75                  80                  85

TAGAAGAAGA AGGTGGAGAG AGAGACAGAG ACAGATCCAT TCGATTAGTG AACGGATCCT      410

TGGCACTTAT CTGGGACGAT CTGCGGAGCC TGTGCCTCTT CAGCTACCAC CGCTTGAGAG      470

ACTTACTCTT GATTGTAACG AGGATTGTGG AACTTCTGGG ACGCAGGGGG TGGGAAGCCC      530

TCAAATATTG GTGGAATCTC CTACAGTATT GGAGTCAGGA ACTAAAGAAT AGTGCTGTTA      590

GAATTCTCAA                                                             600

(2) INFORMATION FOR SEQ ID NO:73:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (iv) ANTI-SENSE: NO (ix) FEATURE:
        (A) NAME/KEY: CDS
        (B) LOCATION: 232..579

(xi) SEQUENCE DESCRIPTION: SEQ ID NO:73:

ATAAGAATTC TGCAACAACT GCTGTTTATC CATTTTCAGA ATTGGGTGTC GACATAGCAG       60

AATAGGCGTT ACTCGACAGA GGAGAGCAAG AAATGGAGCC AGTAGATCCT AGACTAGAGC      120

CCTGGAAGCA TCCAGGAAGT CAGCCTAAAA CTGCTTGTAC CAATTGCTAT TGTAAAAAGT      180

GTTGCTTTCA TTGCCAAGTT TGTTTCATAA CAAAAGCCTT AGGCATCTCC T ATG GCA       237
                                                          Met Ala
                                                           1

GGA AGA AGC GGA GAC AGC GAC GAA GAG CTC ATC AGA ACA GTC AGA CTC        285
Gly Arg Ser Gly Asp Ser Asp Glu Glu Leu Ile Arg Thr Val Arg Leu
          5                  10                  15

ATC AAG CTT CTC TAT CAA AGC AAC CCA CCT CCC AAC CCG AGG GGA CC         333
Ile Lys Leu Leu Tyr Gln Ser Asn Pro Pro Pro Asn Pro Glu Gly Thr
 20                  25                  30

CGA CAG GCC CGA AGG AAT AGA AGA AGA AGG TGG AGA GAG AGA CAG AGA        381
Arg Gln Ala Arg Arg Asn Arg Arg Arg Arg Trp Arg Glu Arg Gln Arg
 35                  40                  45                  50

CAG ATC CAT TCG ATT AGT GAA CGG ATC CTT GGC ACT TAT CTG GGA CGA        429
Gln Ile His Ser Ile Ser Glu Arg Ile Leu Gly Thr Tyr Leu Gly Arg
                 55                  60                  65

TCT GCG GAG CCT GTG CCT CTT CAG CTA CCA CCG CTT GAG AGA CTT ACT        477
Ser Ala Glu Pro Val Pro Leu Gln Leu Pro Pro Leu Glu Arg Leu Thr
```

-continued

```
                        70                    75                    80
CTT GAT TGT AAC GAG GAT TGT GGA ACT TCT GGG ACG CAG GGG GTG GGA              525
Leu Asp Cys Asn Glu Asp Cys Gly Thr Ser Gly Thr Gln Gly Val Gly
            85                    90                    95

AGC CCT CAA ATA TTG GTG GAA TCT CCT ACA GTA TTG GAG TCA GGA ACT              573
Ser Pro Gln Ile Leu Val Glu Ser Pro Thr Val Leu Glu Ser Gly Thr
    100                   105                   110

AAA GAA TAGTGCTGTT AGAATTCTCA A                                              600
Lys Glu
115
```

(2) INFORMATION FOR SEQ ID NO:74:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (iv) ANTI-SENSE: NO (xi) SEQUENCE DESCRIPTION: SEQ ID NO:74:

NNNNNCCTNN NNNAGGNNNN NNNNN                                                  25

(2) INFORMATION FOR SEQ ID NO:75:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (iv) ANTI-SENSE: NO (xi) SEQUENCE DESCRIPTION: SEQ ID NO:75:

NNNNNCCTNN NNNNAGGNNN NNNNNN                                                 26

(2) INFORMATION FOR SEQ ID NO:76:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:76:

GGTAAAGTCT TAACCCACAG CTGTATC                                                27

ANTISENSE VIRUSES AND ANTISENSE-RIBOZYME VIRUSES

FIELD OF THE INVENTION

This invention relates generally to artificial antisense viruses (ASV) and antisense-ribozyme viruses (ARV), and to use such viruses to inhibit the replication of natural viruses.

BACKGROUND OF THE INVENTION

Antisense technologies have been employed primarily to block gene expression. During the process of gene expression, the information encoded in a gene (DNA) is first transcribed into a messenger RNA (mRNA) that is in turn translated into a protein. The original idea behind antisense technology was to create a piece of polynucleotide (RNA or DNA) with a base sequence complementary to that of a particular messenger RNA. This antisense RNA would bind to the mRNA, preventing it from being translated into protein as shown below:

Oeller et al, Science 254:437 (1991) describe reversible inhibition of tomato fruit senescence by antisense RNA. The authors chose one of the other targets to control tomato fruit ripening. They introduced into tomato plants an antisense RNA expression vector to 1-aminocyclopropane-1-carboxylate (ACC) synthase, the rate-limiting enzyme in the biosynthetic pathway of ethylene which controls fruit ripening. The expression of the antisense RNA in the transgenic tomato plants inhibited tomato ripening and the biochemical changes associated with it, such as softening, color and aroma development. Administration of exogenous ethylene or propylene reversed the inhibitory effect. The authors noted that expression of antisense RNA to ACC synthase may ameliorate losses due to over-ripening of fruits and vegetables during transportation or because of lack of refrigeration.

Day A G et al. Proc Natl Acad Sci USA 88:6721–5, 1991, report the application of antisense RNA technology, in plants, to achieve resistance to infection by a geminivirus. The authors constructed transgenic tobacco plants carrying a genetic cassette including an antisense DNA sequence of the virally encoded AL1 gene of the geminivirus tomato

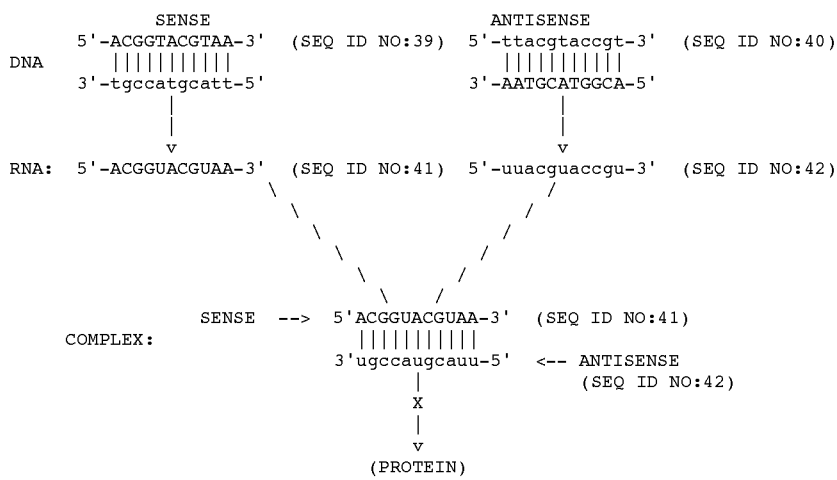

APPROACHES BY OTHER RESEARCHERS RELATED TO ANTISENSE STRATEGY

A. Antisense Expression Constructs

Genes are composed of two strands of DNA, only one of which is normally transcribed into mRNA. If the protein-coding portion of the gene is flipped over, the gene's regulatory sequence will cause the other—or "wrong"—strand to be transcribed, allowing a cell to produce antisense RNA. The antisense RNA produced by the flipped gene will bind and inactivate the RNA produced by the normal gene.

Izant J G & Weintraub H. Cell 36:1007–15 (1984) showed that the synthesis of the enzyme thymidine kinase (TK) could be blocked in mouse cells if a flipped version of the thymidine kinase gene was introduced into the cells along with the normal gene.

Two independent groups (Sheehy R E et al. Proc Natl Acad Sci USA 85:8805, 1988; Smith C J S et al. Nature 334:724, 1988; Smith C J S et al. Plant Mol Biol 14:369, 1990) created mush-resistant tomatoes by genetically engineering the plant to contain a flipped version of the gene for polygalacturonase, an enzyme that breaks down plant cell walls. As a result production of the enzyme was reduced up to 99% without directly disrupting the expression of other genes. Otherwise, the tomato plants appeared normal (Moffat A S. Science 253:510, 1991).

golden mosaic virus (TGMV). AL1 encodes a protein absolutely required for TGMV DNA replication. After infection of plants with TGMV, the frequency of symptom development was very significantly reduced in a number of antisense lines, and no DNA replication was seen in five of the six antisense lines studied, in contrast to controls.

Han L, Yun J S & Wagner T E. Proc Natl Acad Sci USA 88:4313–4317 1991, genetically engineered mice to express an antisense RNA to the Moloney murine leukemia virus (M-M$\mu$lV) proviral packaging sequences, which are needed to make infectious particles of the leukemia-causing virus. When these transgenic mice were infected with M-MuLV on the day of birth, none developed any symptoms of leukemia, although 31% of the control animals did.

The Wagner group's results caused molecular geneticist John Rossi of the city of Hope Medical Center in Duarte, Calif., to declare that "antisense is going to be a powerful antiretroviral tool." It might be possible, Wagner suggested, to genetically engineer lymphocytes, one of the major cell types infected by the AIDs virus, with antisense constructs that prevent the virus from replicating (Moffat A S. Science 253:510, 1991).

B. Synthetic Antisense RNAs or DNAs

Melton's group (Melton DA. Proc Natl Acad Sci USA 82:144, 1985; Rebagliati M R & Melton D A. Cell 48:614, 1987) showed that synthesis of specific proteins could be prevented in frog eggs simply by injecting them with synthetic antisense RNAs.

Calabretta's group (Szczylik C et al. Science 253:562–65, 1991) made a short, single-stranded antisense DNA, just 18 nucleotides long, that specifically recognizes the junction of the ABL hybrid gene resulted by "philadelphia chromosome translocation". The antisense construct stops the growth of the cancer cells but not that of the normal cells from which the cancer cells were derived.

ANTISENSE STRATEGY RELATING TO HIV-1

A. Antisense Oligonucleotides

Vickers, et al, Nucleic Acids Res., 25 19(12):3359–68 (1991) describe inhibition of HIV-LTR gene expression by oligonucleotides targeted to the TAR elements. A series of phosphodiester and phosphothioate antisense oligonucleotides were constructed which specifically bind to the HIV TAR element. The reason for using the phosphothioate analogues was based on the fact that these analogues are more resistant to degradation by DNase activities, enabling higher oligonucleotide concentration inside the cells.

Renneisen, et al, J. Biol. chem., 25 265(27):16337–42 (1990), describe inhibition of expression of human immunodeficiency virus-1 in vitro by antibody-targeted liposome containing antisense RNA to the env region. Treatment of HIV-1IIIB infected H9 cells with in vitro synthesized viral env region antisense RNA encapsulated in liposomes targeted by antibodies specific for the T-cell receptor molecule CD3 almost completely inhibited HIV-1 production. The viral env segment covered a part of exon II of HIV-1 tat gene. No anti-HIV activity could be detected with similarly targeted liposome-encapsulated sense env RNA or with pol RNA synthesized in either the sense or antisense orientations, or with env region antisense RNA free in solution, or encapsulated in liposomes in the absence of the targeting antibody. A semiquantitative evaluation revealed that 4000–7000 RNA molecules became cell-bound in targeted liposomes; the half-life of the intracellularly present hybridizable antisense env RNA was approximately 12 hours. Western blots showed that antisense env RNA suppressed tat gene expression by approximately 90% and gp160 production by 100%. These data were confirmed by immunoprecipitation studies. Northern blots (using an env probe) demonstrated the existence of all major HIV RNA species (9.3-, 4.3-, and 2.0-kb mRNA) in HIV-infected cells treated with antisense env RNA although at a reduced level. It was concluded that the antisense env RNA inhibited viral protein production at the translational level.

B. Antisense Expressing Constructs

Rhodes et al, J. Gen. Virol., 71(pt9):1965–74 (1990), describe inhibition of human immunodeficiency virus replication in cell culture by endogenously synthesized antisense RNA. Six regions from HIV-1IIIB were inserted into retroviral gene expressing vector in antisense orientation. Two of these expressed antisense RNAs were found to reduce significantly the replication of HIV-1IIIB in cell culture. The inhibitory antisense RNAs contain sequences complementary to the AUG initiation codon of the tat gene. Inhibition was substantial (over 70%) but transient. At least part of the inhibitory effect is at the posttranscriptional level.

Rhodes et al, AIDS, 5(2):145–51 (1991), describe inhibition of heterologous strains of HIV by antisense RNA. The longer (600 bases) of the two inhibitory antisense RNAs inhibits replication of HIV strains RF, MN and SF2 to at least as great an extent as it does the homologous strain IIIB. The shorter one (71 bases) does not inhibit the replication of the heterologous strains. The level of inhibition of HIV-1IIIB replication varied according to the cell line in which it was expressed, but in all cases was significant.

Rittner et al, Nucleic Acids Res., 19(7):1421–6 (1991) disclose identification and analysis of antisense RNA target regions of the human immunodeficiency virus type 1. Antisense RNA, transcribed intracellularly from constitutive expression cassettes, inhibits the replication of HIV-1 as demonstrated by a quantitative microinjection assay in human SW480 cells. Infectious proviral HIV-1 DNA was co-microinjected together with a fivefold molar excess of plasmid expressing antisense RNA complementary to a set of ten different HIV-1 target regions. The most inhibitory antisense RNA expression plasmid were targeted against a 1 kb region with the gag open reading frame and against a 562 base region containing the coding sequences for the regulatory viral proteins tat and rev.

OBJECTS OF THE INVENTION

It is an object of the invention to provide novel compounds and methods of treating and preventing viral infections including HIV infections.

It is an object of the invention to provide therapeutic agents for the treatment and prevention of AIDS having:

(1) the ability to target HIV;

(2) the power to inactivate (disable or eliminate) HIV;

(3) the specificity to act only on HIV;

(4) the potential to protect the cells against HIV;

(5) a long in vivo life.

It is an object of the invention to provide a method of producing antisense viruses.

It is an object of the invention to to provide a method of producing antisense-ribozyme viruses.

SUMMARY OF THE INVENTION

The present invention provides an antisense virus comprising a viral coat sufficiently duplicative of a naturally occurring virus viral coat to allow the infectivity of the naturally occurring virus, and nucleic acid including an antisense fragment which is antisense to a section of a gene encoding a transactivating protein required for the naturally occurring virus to replicate. The antisense fragment encodes antisense RNA capable of binding and inactivating mRNA encoded by the gene encoding a transactivating protein.

The invention further provides a process for the production of an antisense virus. The process comprises the steps of a) growing under suitable nutrient conditions procaryotic or eucaryotic host cells transfected in a manner allowing expression of said antisense virus, with:

i) a first DNA sequence including structural genes of a naturally occurring virus, and an antisense fragment which is antisense to a section of a gene encoding a transactivating protein required for the naturally occurring virus to replicate, and ii) a second DNA sequence encoding the transactivating protein, and b) isolating the antisense virus.

Also comprehended by the invention is a method of treating or preventing a viral infection comprising administering to an infected animal a therapeutically effective amount of an antisense virus.

Also provided is an antisense-ribozyme virus comprising a viral coat sufficiently duplicative of a naturally occurring virus viral coat to allow the infectivity of the naturally occurring virus, and nucleic acid including an antisense fragment which is antisense to a section of a gene encoding a transactivating protein required for the naturally occurring virus to replicate. The antisense fragment encodes antisense RNA capable of binding and inactivating mRNA encoded by the gene encoding a transactivating protein. The antisense fragment also encodes at least one ribozyme capable of cleaving the mRNA.

The invention further provides a process for the production of an antisense ribozyme virus. The steps include a) growing under suitable nutrient conditions procaryotic or eucaryotic host cells transfected in a manner allowing expression of the antisense ribozyme virus, with:

i) a first DNA sequence including structural genes of a naturally occurring virus, and an antisense fragment which is antisense to a section of a gene encoding a transactivating protein required for the naturally occurring virus to replicate. The antisense fragment encodes antisense RNA capable of binding mRNA encoded by the gene encoding a transactivating protein. The antisense fragment also encodes at least one ribozyme capable of cleaving the mRNA, and ii) a second DNA sequence encoding the transactivating protein, and b) isolating the antisense ribozyme virus.

Also included in the invention is a method of treating or preventing a viral infection comprising administering to an infected animal a therapeutically effective amount of an antisense-ribozyme virus.

The invention also provides a method of connecting a first DNA segment to a second DNA segment, when the first DNA segment and the second DNA segment are separated by a length of DNA or located on different molecules. The method comprises carrying out polymerase chain reaction using the DNA segments as templates, and using a primer A complementary to the 5' end of the first DNA segment, a primer B complementary to the 3' end of the second DNA segment, and a bridging primer comprising DNA complementary to the 3' end of the first DNA segment as its 5' half, and DNA complementary to the 5' end of the second DNA segment as its 3' half, as primers.

BRIEF DESCRIPTION OF THE DRAWINGS

FIG. 1 shows pX (short for pHXB2gptX). Three arrows point to three EcoNI sites. When sites #2 and #3 are eliminated, pX becomes pXE.

FIG. 2 shows the genomic structure of HIV-I. Each of the nine known genes of HIV-1 are shown, and their recognized primary functions summarized. The 5' and 3' long terminal repeats (LTRs) containing regulatory sequences recognized by various host transcription factors are also depicted, and the positions of the Tat and Rev RNA response elements (TAR (transactivation response) element and Rev response element) are indicated.

FIG. 3 shows a schematic diagram of the HIV-1 Virion. Each of the virion proteins making up the envelope ($gp12^{env}$ and $gp41^{env}$) and nucleocapsid ($p24^{gag}$, $p17^{gag}$, $p9^{gag}$, and $p7^{gag}$ is identified. In addition, the diploid RNA genome is shown associated with reverse transcriptase, an RNA-dependent DNA polymerase.

FIG. 4 is a diagram of pXE, pXE-a, and pXE-ar.

FIG. 5 shows the plasmid structure of SFneo.

FIG. 6 shows the genetic organizations of HIV-1, HIV-2 and SIV.

FIG. 7 is a diagram of SFneo-tat(+) and SFneo-tat(−).

DETAILED DESCRIPTION OF THE INVENTION

The subject invention relates to antisense viruses (ASV) and antisense ribozyme viruses, their synthesis, and their use in treating and preventing viral infections.

Antisense viruses are artificial viruses carrying antisense nucleotide sequences to their natural counterparts. Antisense RNAs expressed by the antisense viruses bind to the mRNAs expressed by the naturally occurring viruses and prevent the mRNAs from being translated into proteins, thereby preventing the naturally occurring virus from replicating. The antisense viruses maintain the infectivity of the naturally occurring viruses, allowing antisense RNAs to reach the mRNAs of the natural viruses. Antisense virus strategy provides a new therapy for viral, including retroviral diseases.

The antisense virus of the invention comprises the viral coat (i.e., the envelope and optionally the capsid in the case of enveloped viruses, and the capsid in the case of viruses without an external envelope) sufficiently duplicative of a naturally occurring viral coat to give the antisense virus the infectivity of the naturally occurring virus, and nucleic acid including an antisense fragment which is antisense to a section of a gene encoding a transactivating protein required for said naturally occurring virus to replicate. The antisense fragment encodes antisense RNA which is capable of binding and inactivating mRNA encoded by the gene encoding a transactivating protein. Typically, the viral coat of the antisense virus is identical to the corresponding naturally occurring virus. The nucleic acid of the antisense virus typically contains all the structural genes of the naturally occurring virus. Further, nucleic acid typically includes all of the regulatory genes of the naturally occurring virus except the gene encoding the transactivating protein. Advantageously, the nucleic acid of the antisense virus is the same as the nucleic acid of the corresponding virus with the exception of the antisense fragment (which replaces a section of a gene). Since the antisense virus does not contain a gene required for replication of the virus, the antisense virus is replication defective. The antisense fragment is part or all of the gene encoding the protein required for replication, turned antisense. The length of the antisense fragment must be sufficient to permit the antisense RNA transcribed from the antisense fragment to bind and inactivate the mRNA encoded by the gene encoding the required protein of the naturally occurring virus, thus thwarting replication of the naturally occurring virus. Thus, the antisense fragment is part or all of the target gene turned antisense. As used herein, the term "section of a gene" refers to part or all of the gene(s) encoding the transactivating protein(s) required for the naturally occurring virus to replicate.

The antisense virus of the subject application is made for use in treating or preventing disease caused by a wide variety of naturally occurring viruses. Antisense viruses is made to treat or prevent animal or plant viral infections. Further, antisense viruses are made to render inactive DNA as well as RNA viruses. Further, the antisense virus of the invention is used to treat or prevent infections caused by retroviruses.

Since the antisense virus of the subject invention is replication defective, a special host cell is required to produce the antisense virus in vitro. The antisense virus is replication defective since it does not contain a gene encoding a protein required for replication. In order for the host cell to be able to construct an antisense virus, it must contain a gene encoding the protein which the antisense virus requires. This protein must be a transactivating protein since it is supplied by a source other than the nucleic acid of the antisense virus. In order to avoid the antisense RNA encoded by the antisense fragment from binding the mRNA transfected from the complemental gene, the complemental gene sequence is typically "diversified" such that the antisense RNA will not bind the mRNA transcribed from the complemental gene. The amino acid sequence of the protein produced by the complemental gene, however, is the same as the corresponding protein of the naturally occurring virus.

In order to construct the cell line which produces the antisense virus, the complemental gene can be transfected into the host cell before, at the same time, or after transfection of the host cell with the gene encoding the antisense virus.

The subject invention also relates to antisense-ribozyme viruses (ARV) which are the same as antisense viruses except one or more ribozyme catalyst sequences have been incorporated into the antisense sequence(s). The antisense-ribozyme viruses are structured such that the binding of the antisense RNA to a particular mRNA will meet the requirements for the formation of specific structure enabling ribozymes to cleave the particular mRNA at predetermined positions. The ability of ribozymes to cleave RNA plus the binding specificity of antisense RNA give antisense-ribozyme viruses the ability to eliminate the natural viruses.

Antisense viruses and/or antisense-ribozyme viruses are often referred to collectively herein as "antisense/ribozyme viruses" or "ASV/ARV".

Although antisense viruses and/or antisense-ribozyme viruses to HIV-1, HIV-2 (human immunodeficiency viruses type 1 and 2) and SIV (simian immunodeficiency virus) are exemplified herein, the strategy is applicable to other viruses.

Definitions

ANTISENSE/RIBOZYME HIV-1 CLONES

A. Full-Length Proviral Molecular Clones and Antisense/Ribozyme Proviral Molecular Clones:

pX: Short for pHXB2gptX. HXB2 is a functional HIV-1 molecular clone which has been widely employed in many kinds of experiments all over the world. The plasmid construct of pX is shown in FIG. 1.

Figure 2:
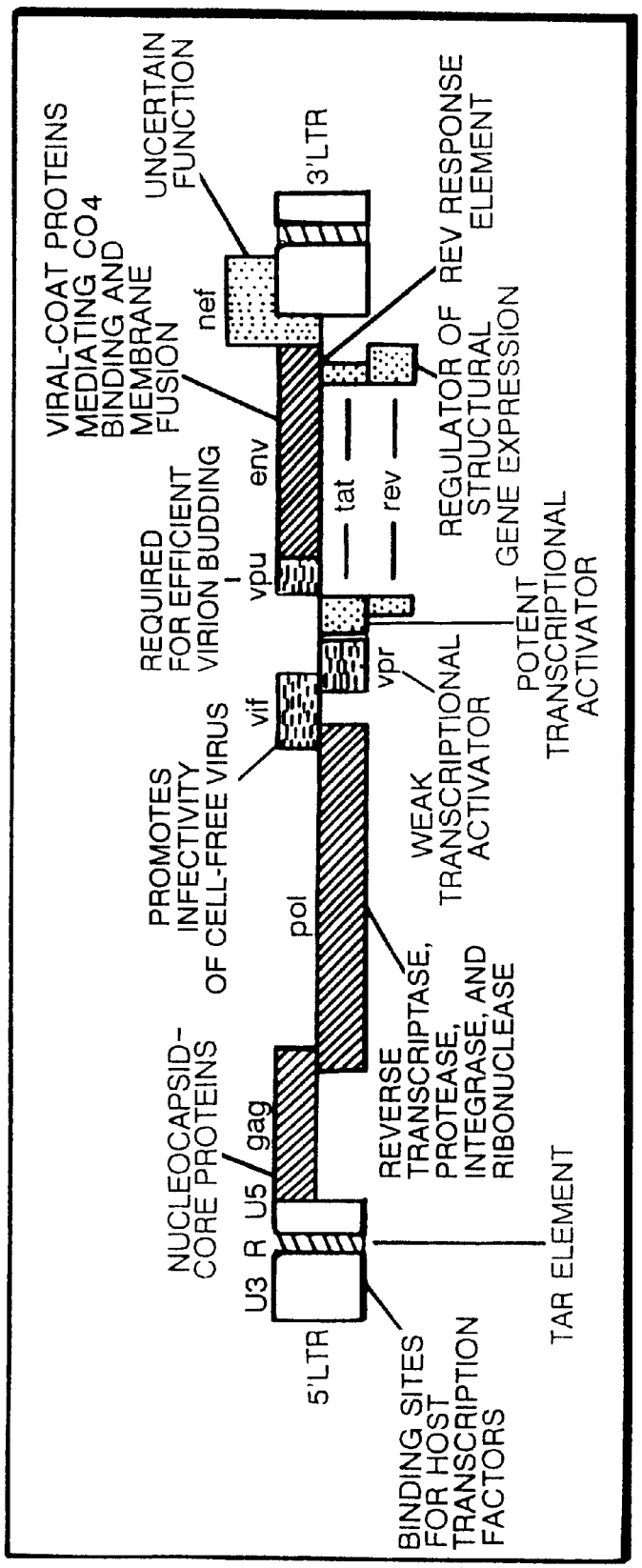
Figure 3:
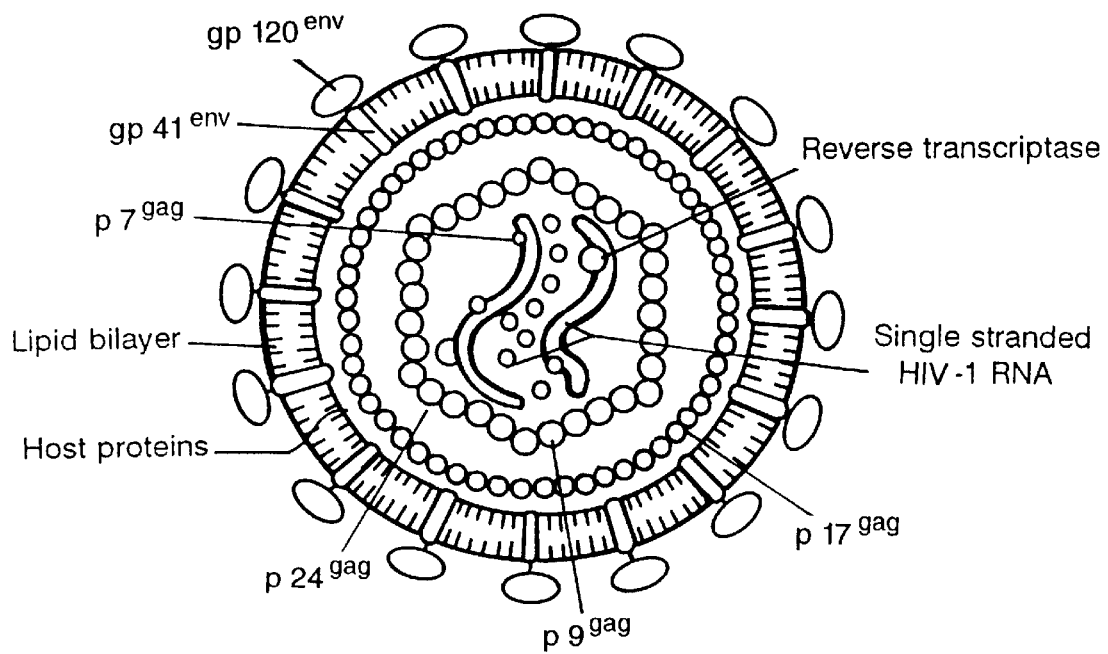

The genomic structure of HIV-1 is shown in FIG. 2. A schematic diagram of the HIV-1 virion is shown in FIG. 3.

The genetic organization of parental pX (HIV-1IIIB) is shown below. Only those restriction enzyme sites to be used during the construction procedures are shown.

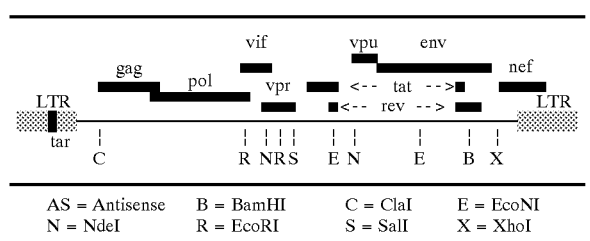

pNL: Short for pHIVNL4-3. An infectious recombinant HIV-1 clone that contains DNA from HIV isolates NY5 (5' half) and BRU (3' half). The site of recombination is the unique EcoRI site at nt 5743–5748. The vpr coding region of pNL is 18 amino acid residues longer than that of pX, due to a single "T" base deletion at nt 5770. The genetic organization of pNL is almost the same as pX, but the vpr is longer, and the ClaI site and the first EcoRI site are missing.

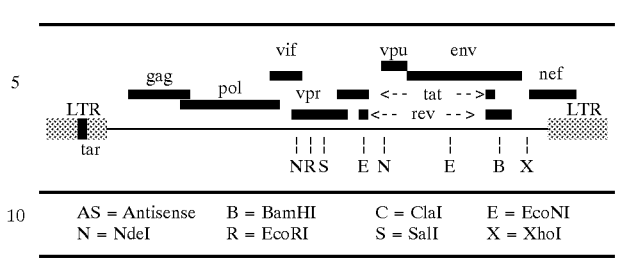

pXE: Modified from pX to facilitate the construction of antisense/ribozyme clones. A "T" to "G" point mutation has been introduced at nt 7633 in order to abolish the second EcoNI restriction site within the proviral sequence. The EcoNI site outside the proviral sequence has also been removed by polymerase fill-in and religation. pXE is considered the same as pX, but has only one EcoNI cleavage site at nt 5966 in the whole clone. The point-mutation introduced does not change the protein sequences.

Genetic organization of pXE is as follows (see also FIG. 4). Note the second EcoNI site has been deleted. The deletion, however, did not change the genetic organization.

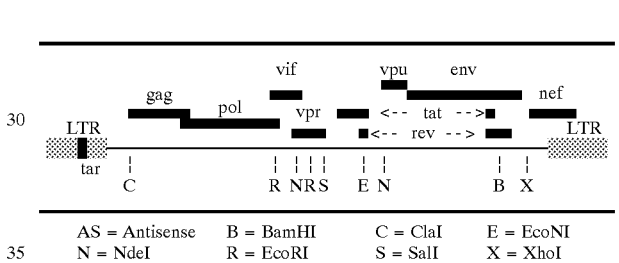

pXE-a: A DNA fragment of 171 base pairs, from nt 5795 to nt 5965, covering 45 amino acid codons of the N-terminus of the TAT protein, has been turned antisense. Consequently, the production of the whole TAT protein would be eliminated.

Genetic organization of antisense clone pXE-a is as follows (see also FIG. 4). The sequence between SalI and EcoNI sites has been turned antisense. As a consequence of this inversion, the tat gene is destroyed and the whole clone becomes replication defective.

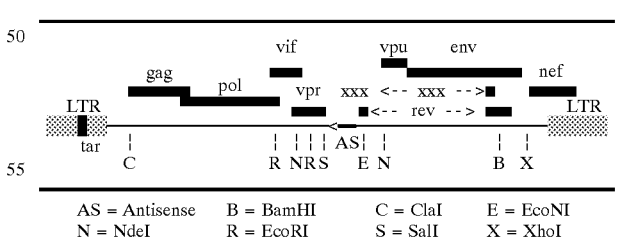

pXE-b: Same as pXE-a plus the nt 5970 "T" has been mutated to "G". As the consequence of this point-mutation, the initiation codon of rev is erased as is the whole REV protein.

Genetic organization of antisense clone pXE-b is as follows. The sequence between SalI and EcoNI sites has been turned antisense. Consequently, the tat gene is destroyed and the whole clone becomes replication defec tive. Additionally, the initiation codon of rev gene has been mutated and the rev gene too is eliminated.

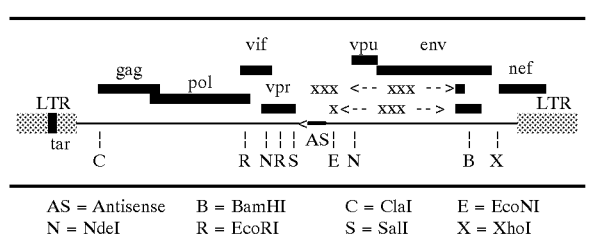

| AS = Antisense | B = BamHI | C = ClaI | E = EcoNI |
| N = NdeI | R = EcoRI | S = SalI | X = XhoI | pXE-ar: A ribozyme catalytic domain has been incorporated into the antisense sequence of pXE-a, thus adding the RNA cleavage activity to the antisense clone.

Figure 4:
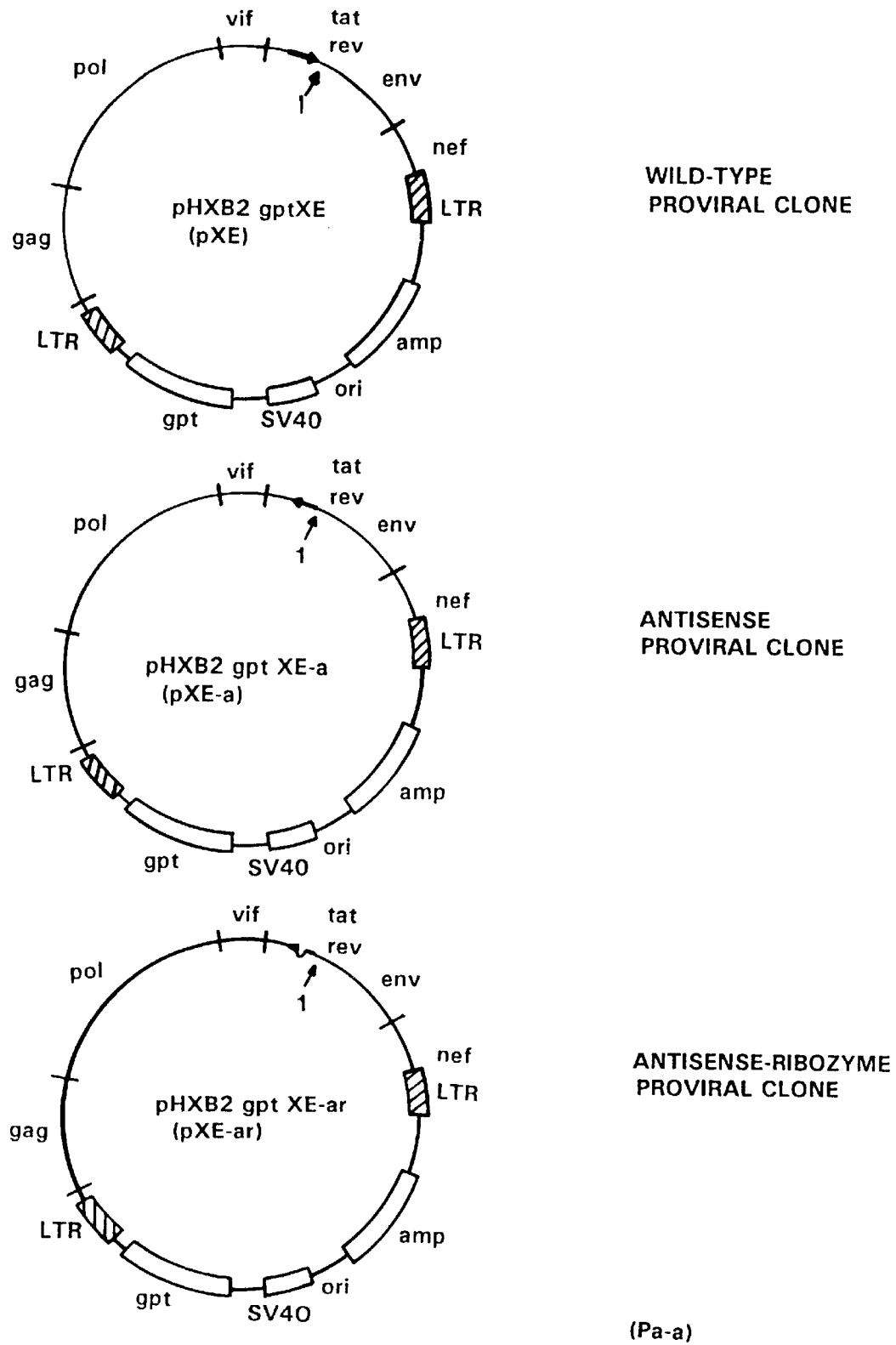

Genetic organization of antisense clone pXE-ar is similar to pXE-a (see FIG. 4). Note the position of the ribozyme.

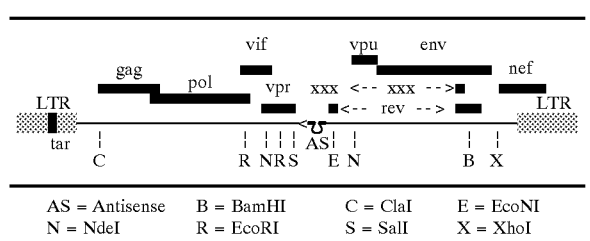

| AS = Antisense | B = BamHI | C = ClaI | E = EcoNI |
| N = NdeI | R = EcoRI | S = SalI | X = XhoI | pXE-br: A ribozyme catalytic domain has been incorporated into the antisense sequence of pXE-b, thus adding the RNA cleavage activity to the antisense clone.

Genetic organization of antisense clone pXE-br is similar to pXE-b. Note the position of the ribozyme.

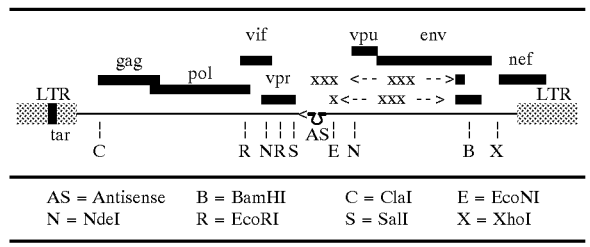

| AS = Antisense | B = BamHI | C = ClaI | E = EcoNI |
| N = NdeI | R = EcoRI | S = SalI | X = XhoI |

B. HIV-1 Subclones:

pX-N: Made from pX. An NdeI fragment of 1281 bps, from 5121 to 6402, has been removed from pX and religated. Included in the removed fragment, among other things, are the unique NcoI-5674, SalI-5785 and a EcoNI-5966. pX-N contains 2 other EcoNI sites, one at nt 7631 and the other outside the proviral sequences.

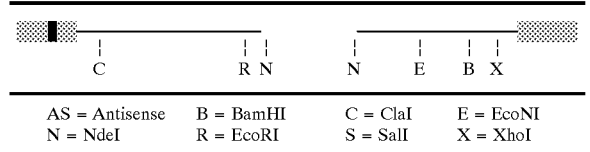

| AS = Antisense | B = BamHI | C = ClaI | E = EcoNI |
| N = NdeI | R = EcoRI | S = SalI | X = XhoI | pX-N-E: Made from pX-N with the two EcoNI sites eliminated. The EcoNI-7631 has been point-mutated, and the outside EcoNI has been enzymatically erased.

pX-E2: The fragment of ClaI(829)-BamHI(8474) from pX has replaced the corresponding fragment of pX-N-E, thus putting back the 1281-bp NdeI fragment. Also put back are the EcoNI sites at nt 5966 and nt 7631.

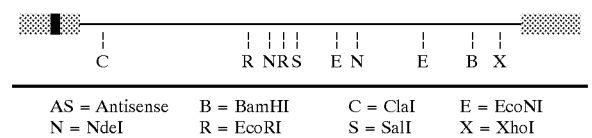

| AS = Antisense | B = BamHI | C = ClaI | E = EcoNI |
| N = NdeI | R = EcoRI | S = SalI | X = XhoI | pXE: The EcoNI site at nt 7631 has been point-mutated so the whole clone carries a unique EcoNI site at nt 5966. See also "Full-Length Molecular Clones or Mutants" above.

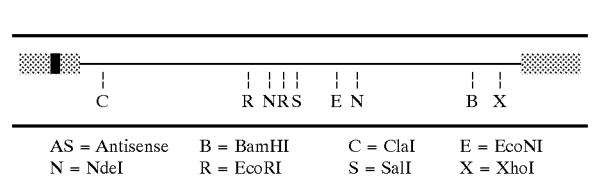

| AS = Antisense | B = BamHI | C = ClaI | E = EcoNI |
| N = NdeI | R = EcoRI | S = SalI | X = XhoI |

C: Gene-Expression Vector Clones:

pX-CS: A truncated HIV-1 clone made from pX and used as tat-expression vector. Removed from this clone are 4484 bps, from nt 836 to nt 5319 including most part of gag, all of pol and 5' half of vif open reading frames. The vpr, tat, rev, env, and nef genes and two LTRs are intact.

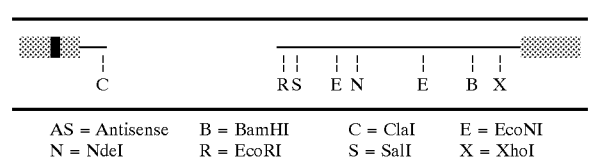

| AS = Antisense | B = BamHI | C = ClaI | E = EcoNI |
| N = NdeI | R = EcoRI | S = SalI | X = XhoI | pX-CSneo: A 1146-bp neo(r) cassette containing an XhoI-SalI fragment has been inserted into the unique XhoI site in pX-CS. This clone has been endowed with neomycin resistance, but the insertion disrupts the nef gene.

pX-neo: Made from pX-CSneo. The SalI(5785)-XhoI (8896) (3111 bps) fragment, covering tat, rev and env coding regions, has been deleted from pX-CSneo. Essentially, pX-neo contains 2 HIV-1 LTRs with a neomycin resistant gene in between. This clone is used as neo(r)-only control.

Figure 5:
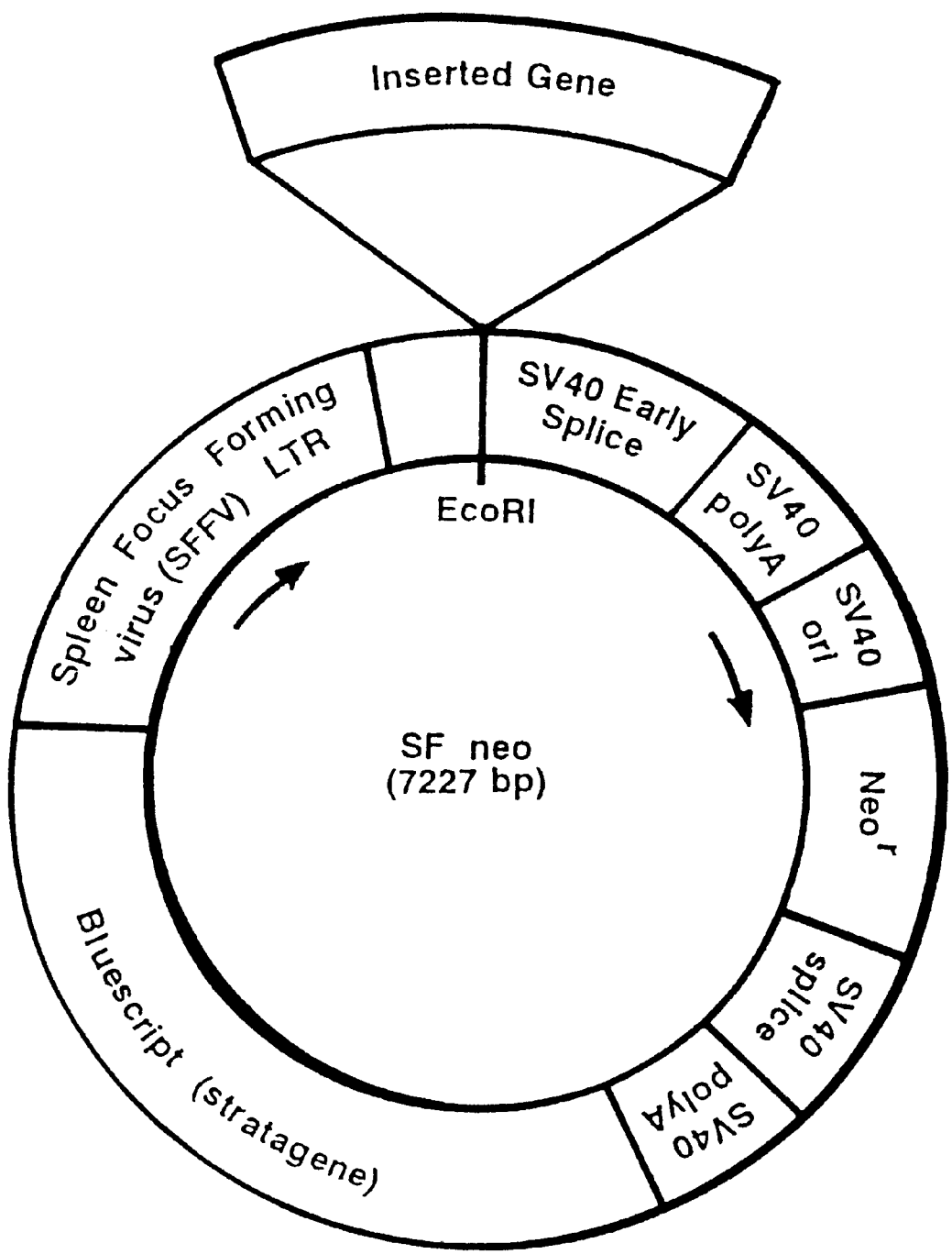
Figure 6:
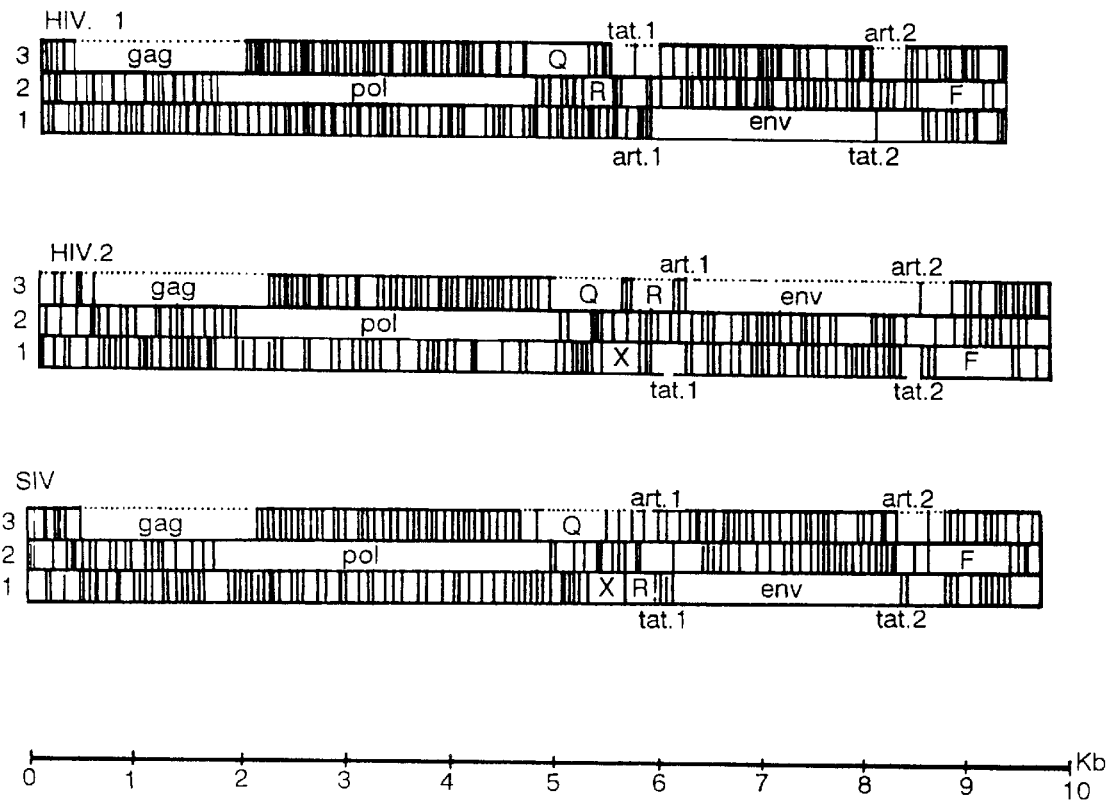

SFneo: Retroviral gene expression vector which employs Spleen Focus Forming Virus (SFFV) LTR promotor to drive the expression of the gene to be inserted into the unique EcoRI site. This clone is used also as neo(r)-only control. The plasmid structure is shown in FIG. 5.

SFneo-t/r(+): Tat as well as rev reading frames in continuation has been inserted in right orientation into the EcoRI site of SFneo. This clone expresses sense tat and rev mRNA.

SFneo-t/r(−): Tat as well as rev reading frames in continuation has been inserted in wrong orientation into the EcoRI site of SFneo which employs Spleen Focus Forming Virus (SFFV) LTR promotor to drive the expression of the inserted gene. This clone expresses antisense tat and antisense rev mRNA.

SFneo-tat(+): Inserted in right orientation into SFneo vector at EcoRI site the chemically synthesized nucleotide sequence which is different from the natural nucleotide sequence. This clone expresses sense mRNA which is translated into TAT protein with amino acid sequence identical to that of the natural HIV-1.

SFneo-tat(−): Inserted in wrong orientation into SFneo vector at EcoRI site the chemically synthesized nucleotide sequence which is different from the natural nucleotide sequence. This clone expresses antisense RNA.

ANTISENSE VIRUSES

An antisense virus (ASV) is an artificial virus that expresses antisense RNA to one or more genes of its natural counterpart. An antisense virus is generally replication defective, necessitating an antisense virus production system in order to produce large quantities of antisense viruses for therapeutic and preventive applications. The antisense virus production system comprises three components:

(1) an antisense proviral molecular clone;
(2) a complemental gene expression vector;
(3) an antisense virus producer cell line (host cells).

An antisense-ribozyme virus production system uses the same components (2) and (3) combined with an antisense-ribozyme proviral molecular clone (discussed below).

The function and establishment of each component of the antisense virus production system will be exemplified in detail for an antisense virus for HIV-1. Similar systems for other human viruses such as HIV-2 and SIV are easily developed by a person skilled in the art because of the similarity of genetic organizations between HIV-1, HIV-2 and SIV. The genetic organizations of HIV-1, HIV-2 and SIV are shown in FIG. 6. Similar systems for other types of viruses can also be developed.

HIV-1 Antisense Proviral Clones

An HIV-1 antisense proviral molecular clone is made from a functional (infectious) HIV-1 molecular clone. It retains all of the natural HIV-1 structures and machinery except a part (or parts) of the genome has been turned antisense by sequence inversion. The antisense proviral clone is basically an intact molecular clone but the sequence inversion inactivates some functionally critical gene(s) and renders the whole clone replication-defective. However, the antisense proviral clone is constructed such that the function (s) of the inversion-inactivated gene(s) can be complemented by gene product(s) provided by another source or sources than the antisense clone itself. In other words, replication of the antisense clone depends on gene product (s) from source(s) other than the antisense clone itself.

In the presence of the gene product(s) provided by a "complemental gene expression vector" for functional complementation, the antisense proviral clone makes virus particles (antisense viruses) in the antisense virus producer cell line. The constant presence of gene product(s) is achieved by engineering the antisense virus producer cell line to express the protein(s) constitutively before, during or after the antisense proviral clone is transferred into the cells. With this antisense virus production system the antisense viruses are made in quantity in vitro.

The antisense virus is infectious and has the same "targeting" or "homing" specificity as the naturally occurring (wild type) virus. The antisense HIV-1 virus is able to attach to and enter CD4(+) cells, mediated by its normal envelope proteins (gp120 and gp41) just as the natural virus. Once inside the cells, the viral nucleocapsid reverse-transcribes its RNA genome into DNA, then integrates the viral DNA into the host genome, just as the natural virus does. But the antisense virus is non-replicative, hence non-pathogenic, in the absence of the gene product(s) that the antisense virus is missing. In the case where the antisense virus enters a healthy cell where no viral protein is being synthesized for functional complementation, the antisense virus will not replicate.

In the case where the antisense virus enters a cell which has already been infected by natural virus(es), the antisense virus will compete for survival (replication) with the natural virus(es) for the gene product(s) provided only by the latter. Once replicating, the antisense transcript (antisense RNA) will bind the natural transcript. The binding will shut off the natural viral protein synthesis; and vice versa. The consequence will be the inhibition, and eventually eradication, of the natural viruses and the antisense viruses.

If the antisense virus enters a cell which becomes infected later by a natural HIV-1 virus, the dormant antisense provirus (having integrated into the human genome) is re-activated by the gene product(s) encoded by the natural virus. Its transcription produces antisense RNA which shuts off the natural virus.

If the cell never becomes infected by any natural HIV-1 virus, the antisense provirus will remain dormant and eventually be eliminated with the natural death of the cell. Potentially, the integrated antisense provirus, though unable to make virus without gene product(s) provided from other source(s), will divide with the cell, thus "arming" each daughter cell with one copy of the antisense proviral DNA.

Construction of Antisense HIV-1 Proviral Clones

The antisense HIV-1 proviral molecular clones are constructed with well-known functional (infectious) molecular clones, e.g., HIV-1IIIB and HIV-1NL4-3. The antisense RNA, once transcribed, will carry the same sequences (only some area in antisense orientation) as the wild type mRNA. The sense and antisense RNA sequences form complexes, a basic requisite for the antisense strategy to work.

In case an antisense clone made from an existing molecular clone does not work well with a particular patient's viruses because of sequence heterogeneity, an individualized antisense clone is made, using as a template the very virus strain infecting the particular patient. An antisense clone made in this way has exactly the same sequence (only in antisense orientation) as, and be able to form perfect duplexes with, that of the HIV-1 strain hosted by the patient (described further below).

Choosing Gene(s) for Inversion in HIV-1

An antisense clone is made by inverting part or all of one or more genes of the naturally occurring virus to be neutralized. To be eligible for the inversion, the gene(s) must be indispensable for the replication of the virus, but must not be the structural genes. Structural genes, i.e., in the case of HIV: gag, pol, and env, are necessary for the assembly of infectious virus particles. Infectious virus particles are employed as vehicles to deliver the antisense sequences effectively and specifically to the locations where the naturally infecting viruses reside. It is important for the antisense virus to preserve the natural devices and to retain the same "targeting" or "homing" function as that of the naturally occurring virus.

The rev gene encodes a 19-kd phosphoprotein which is essential for the replication of HIV-1. The Rev protein appears to exert its regulatory activity at a posttranscriptional level by activating the cytoplasmic expression of the unspliced and singly spliced forms of HIV-1 RNA that encode the products of the gag, pol, and env genes. In the absence of Rev, these incompletely spliced viral mRNAs remain sequestered in the nucleus, where they are either degraded or completely spliced. Apparently, Rev positively regulates the formation of virus particles. Since the rev gene overlaps with tat, it is impossible to turn rev antisense without also affecting tat. Thus, the complemental gene expression vector would have to express both rev and tat. Another consideration is that there is a splice junction site at the beginning of rev gene. If the splice junction sequence is turned over, the splicing may be lost, or placed at the wrong location, which would potentially impair the formation of infectious virus particles.

An antisense proviral clone can be made that knocks out the function of the rev gene while keeping the sequence basically unchanged. This goal is achieved by changing the "T" in rev initiation codon (position 5970) into a "G". The single base substitution will (1) abolish the rev gene product; (2) preserve the splice junction site; (3) preserve the unique EcoNI site which is critical in reconstructing antisense clone(s); and (4) create a new restriction enzyme site for AvrII, facilitating recombinant clone screening.

Advantageously, the tat gene is turned antisense. TAT corresponds to an 86-amino-acid nuclear protein that is essential for the replication of HIV-1. TAT potently transactivates the expression of all viral genes. The TAT protein appears to contain three primary structural domains, including a proline-rich N-terminus, a cysteine-rich central portion, and a positively charged distal segment. The cysteine-rich domain (located between amino acids number 21–37 of the protein) probably mediates dimerization of the this trans-activator, whereas the positively charged distal segment is responsible for both RNA binding and nuclear-nucleolar localization. Thus far, no clear function has been ascribed to the proline-rich domain (located at the first 18 amino acids). TAT acts through an RNA stem-loop structure termed the "transactivation response element (TAR)", located at the beginning of all HIV-1 mRNAs. The preponderance of evidence suggests that it acts primarily at the level of transcription initiation, elongation, or both. TAT protein is trans-acting, therefore the TAT function abolished in the antisense clone can be easily compensated by introducing into the cultured cells a TAT-expressing cassette. The TAT protein expressed by this cassette will regulate the replication of antisense HIV-1 whose tat gene has been flipped over and rendered functionless.

Below is a description of a region of the tat gene being turned antisense.

Analyzing the Selected Area for Inversion in the TAT GENE

The original sequences between positions 5774 to 5986 in the HIV-1 molecular clone HXB2 are as follows [numbering according to GenBank, LOCUS HIVHXB2CG, 9718 bp, VRL 25-SEP-1987. DEFINITION: Human immunodeficiency virus type 1 (HXB2), complete genome; HIV1/HTLV-III/LAV reference genome. ACCESSION K03455]. Notice the coding sequences for the end part of vpr (which is different between clone pNL4-3 and HXB2), the beginning of tat-1 and rev-1, the two splice acceptor (sa) sites at positions 5776G/5777A and 5975G/5976G, the unique restriction enzyme sites of Sal-I and EcoNI (positions 5785 and 5966 respectively, both shown underlined. In the subject application, all restriction enzyme sites are indicated by the first base of the enzymes' recognition sequences). EcoNI is unique in plasmid clone pXE but not pX, as detailed later. The area written in bold-type [nucleotides (nt) 5795–5965] is to be turned antisense by sequence inversion.

```
5774   HXB2VPR<--|   5795                               |-->TAT    (SEQ ID NO:43)
| \/sa           |   |                                  |
CAGAATTGGGTGTCGACATAGCAGAATAGGCGTTACTCGACAGAGGAGAGCAAGAAATGGAGCCA
 Q  N  W  V  S  T  *
  R  I  G  C  R  H  S  R  I  G  V  T  R  Q  R  R  A  R  N  G  A
                                                         M  E  P

NLVPR<-|
       |
GTAGATCCTAGACTAGAGCCCTGGAAGCATCCAGGAAGTCAGCCTAAAACTGCTTGTACCAATTG

S  R  S  *
 V  D  P  R  L  E  P  W  K  H  P  G  S  Q  P  K  T  A  C  T  N  C
                                                          5965
                                                             |
CTATTGTAAAAAGTGTTGCTTTCATTGCCAAGTTTGTTTCATAACAAAAGCCTTAGGCATCTCCT

Y  C  K  K  C  C  F  H  C  Q  V  C  F  I  T  K  A  L  G  I  S
|-->REV       5986
|     \/sa       |
ATGGCAGGAAGAAGCGGA-3'
 M  A  G  R  S  G

Y  G  R  K  K  R
```

Three- and one-letter codes for amino acids:

| Amino Acid | Three-letter Code | One-letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |

| | | |
|---|---|---|
| | -continued | |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The inversion involves a total of 171 base pairs (bps). The sequence involvement for HIV1 was decided according to the following considerations. The sequence involvement for other viruses is also decided according to the following considerations.

First, the inversion advantageously should cover as much tat coding sequence as possible, especially the initiation codon (ATG) and the functionally important cysteine codons, in order for the antisense RNA expressed by the antisense viruses to bind as effectively to the natural viral tat mRNA as possible. The wide coverage also minimizes the possibility that the antisense proviral clones remain self-functioning.

Secondly, the inversion should cover as little other gene coding sequences and RNA processing signals as possible, especially the rev gene and splice junctions, in order for the antisense viruses to retain as much other gene functions as possible. The involvement with fewer genes minimizes the complexity for gene complementation by the complemental gene expression vectors.

Thirdly, the inversion should be between, but as close as possible to, two unique restriction enzyme sites in order for the construction of antisense clones to be convenient and easy. The two unique restriction enzyme sites can be either naturally existing or recombinantly created. In the case of antisense HIV-1 proviral clones, the chosen unique restriction sites are SalI and EcoNI, both of which occur only once in the whole plasmid pXE. The inversion is right before the EcoNI site but 4 bps after SalI site only to spare the vpr stop codon (TAG).

The sequences involved are 100% homologous between HIV-1 clones HXB2 and NL4-3. The coding regions, however, are different. In HXB2, the sequence consists of 35-bp non-encoding area located between vpr and tat after the stop codon of vpr and before the initiation codon of tat). Of note is that the vpr in this clone is believed to have been truncated and rendered functionless. The inverted 171 bps sequence further consists of 136-bp in the tat-1 open reading frame where the first 45 amino acids are encoded, including all seven cysteine residues in TAT protein. As a result of the inversion, the following 27 amino acids of TAT-1 (#46-72) are also eliminated because of the frame-shift and the loss of initiation codon. In total, the 72-amino-acid TAT-1 protein is not made. In clone NL4-3, the coding for tat-1 is the same as HXB2, but the carboxyl terminus of vpr extends 55 bps into the inverted region, including a 20-bp overlap with tat-1. Vpr in clone NL4-3 is believed to be intact and functional. The two splice junction sites [splice donor (sd) and splice accepter (sa) are often collectively referred to as splice junctions] immediately before and after the area are not affected by the inversion. The inverted area, after transcribing into mRNA, is able to bind and block the natural HIV-1 mRNA specifically and effectively.

An antisense virus proviral molecular clone is constructed from a functional proviral molecular clone of a naturally occurring virus by inverting ("turning antisense") a section (i.e., part or all) of one or more genes. The inverted section of a selected gene is referred to as the "antisense fragment" herein. To be eligible for selection, the naturally occurring gene must meet two prerequisites. First, this gene must be required for the naturally occurring virus to replicate; and second, the gene must encode a protein product which is transactivating. Other genes are usually not affected during the antisense proviral molecular clone construction. In choosing the sequence of a gene to be inverted, special attention is paid to the gene involved and to its relationship to neighboring genes.

The sequence inversion can be accomplished by conventional recombinant technologies. A new strategy, however, has been developed to construct any antisense virus proviral molecular clone easily and precisely. Recombinant polymerase chain reaction (r-PCR or PCR) technology is employed. The PCR technology is known to those skilled in the art. See U.S. Pat. Nos. 4,683,195 and 4,983,728 hereby incorporated by reference. The strategy of the subject invention (applicable to other viruses as well as HIV1) comprises the steps of:

1) Inserting DNA encoding a naturally occurring virus into a DNA cloning vector. Molecular cloning vectors such as plasmids (including phagemids), bacterial phage lambda and cosmids, are useful as cloning vectors.

2) Selecting a section of the viral DNA to be inverted. The selected section of the viral DNA is part or all of a gene that encodes a transactivating protein product which is required for the naturally occurring virus to replicate. The selected section of the viral DNA is flanked by a unique restriction enzyme site A at its 5' end and by another unique restriction enzyme site B at its 3' end. The unique restriction enzyme sites A and B are either naturally existing or recombinantly created;

3) Carrying out a polymerase chain reaction, using the selected section of the viral DNA as the template, and two specially designed "antisense primers" that target the selected section (in practice, the whole vector containing the whole proviral genome is typically used as the template—there is no need to isolate the selected section in view of the primers used). Antisense Primer 1 comprises at its 3' half a portion of DNA complementary to the 5' end of the selected section of the viral DNA, and at its 5' half a portion of DNA containing the unique restriction enzyme site B. Antisense Primer 2 comprises at its 3' half a portion of DNA complementary to the 3' end of the selected section of the viral DNA, and at its 5' half a portion of DNA containing the unique restriction enzyme site A. The PCR amplification product (the "antisense fragment"), when aligned with the naturally occurring section of the viral DNA, is antisense to the latter between the two unique restriction enzyme sites A and B;

4) Digesting the vector containing the naturally occurring viral DNA with restriction enzymes A and B to release the selected section of DNA;

5) Digesting the PCR amplification product with restriction enzymes A and B to release the antisense fragment;

6) Ligating the antisense section of DNA into the vector in place of the selected sense section of DNA; and 7) Isolating antisense virus proviral molecular clones by standard procedures of transforming appropriate strains of cells such as *E. coli* followed by colony screening.

See also Example 1.

Construction of Antisense HIV-2 Proviral Clones

Methods similar to those used above with HIV-1 are employed to construct antisense HIV-2 proviral clone(s). The construction starts with an infectious HIV-2 plasmid clone named pSE (Hu W et al. Virol. 173:624–630, 1989). A similar PCR strategy is applied to turn over the fragment between nt 5793 and nt 6062 totaling 270 bp in length (numbering according to Guyader M et al. Nature 326:662–669, 1987). This area covers the 3' portion of vpr and 5' portion of tat-1. Because HIV-2 VPR is dispensable for replication and cytopathogenicity (Dedera et al., J. Virol., 63:3205–3208, 1989), only TAT function has to be provided for the production of antisense HIV-2 viruses.

Construction of Antisense SIV Proviral Clones

Similarly, the construction of antisense SIV proviral clone(s) starts with full-length infectious SIVmac plasmid clone p239F (Kestler, et al. Science 248:1109–1112, 1990) or pK102 (Niederman et al. J. Virol. 65:3538–3546, 1991). Similar PCR strategies are utilized to turn over the fragment between nt 5751 and nt 5988, totaling 238 bp in length (numbering according to Chakrabarti et al. Nature 328:543–547, 1987). This area also covers the 3' portion of vpr and 5' portion of tat-1. Because SIV VPR is probably dispensable for replication and cytopathogenicity, only TAT function has to be provided for the production of antisense SIV viruses.

Construction of Antisense Proviral Clones of Other Retroviruses

The construction strategies for antisense proviral clones presented herein apply to all retroviruses. The genes which can be turned antisense, partially or wholly, include all those with transactivation activity. Examples are as follows:

Tax and rex genes of human T-lymphotropic viruses (HTLV-1 and HTLV-2) and of bovine leukemia virus, S gene of Visna Virus, S1 and/or S2 genes of Equine Infectious Anemia Virus (EIAV)

(see S J O'Brien ed. Genetic Maps, locus maps of complex genomes, 5th edition, book 1, viruses, CSH, 1990).

For the oncogene-containing oncoviruses (acutely transforming viruses, ATVs), the oncogenes contained, partially or wholly, are selected to be turned antisense.

Construction of Antisense Clones of Other Viruses

The antisense virus strategies also apply to viruses which contain DNA (not RNA) in their virions, provided that the virus at issue has one or more genes whose translation products are transactivating hence whose inactivation by sequence inversion can be compensated by gene products provided by a gene-expression vector (complemental expression vector), and that a cell culture system is available for making an antisense virus producer cell line. Examples of these viruses and the genes which can be turned antisense are:

X gene of hepatitis B virus,
E1A genes of adenoviruses,
E2 genes of papillomaviruses,
T genes of simian virus 40 and of polyomaviruses, and
genes encoding alpha proteins of herpes viruses (see S J O'Brien ed. Genetic Maps, locus maps of complex genomes, 5th edition, book 1, viruses, CSH, 1990).

ANTISENSE-RIBOZYME VIRUSES

Antisense-ribozyme viruses are the same as antisense viruses but include one or more ribozymes in the antisense sequence(s) which cleave mRNA of the naturally occurring target virus.

The sequence inversion in the aforementioned HIV-1 antisense clones involved 171 base pairs. The sequence included 3' vpr (with pNL) and 5' tat, where it covers the initiation methionine codon and all seven cysteine codons of tat gene. It is possible to form stable complexes between the antisense RNA and the tat mRNA to block the latter from being translated into TAT protein. However, the formation of RNA complexes does not mean the destruction of the RNAs. On the contrary, the complex formation may provide protection to the tat mRNA against degradation in vivo. Ribozyme catalytic sequences incorporated into the antisense RNAs, however, are able to devitalize the bound mRNA molecules by cleaving them into pieces. The combination of antisense strategy with the ribozyme strategy magnifies the antiviral capability of the artificial viruses.

Ribozymes are RNA molecules that catalyze RNA cleavage [Cech, Science 236, 1532–9 (1987); Uhlenbeck O C., Nature (London) 328, 596–600 (1987) ; Forster et al, Cell 49, 211–220 (1987)], i.e., ribozymes are RNA that cut RNA. The simplest of the catalytic motifs of ribozyme is the autocleavage domain of certain plant pathogens (viroids) and viral satellite RNAs (virusoids) called the hammerhead (Forster et al, Cell 49, 211–220 1987). Some other forms from the continuously expanding list of ribozymes are those associated with the self-splicing large ribosomal RNA intron of Tetrahymena, the M1 RNA component of the *Escherichia coli* RNAse P enzyme, and another type of self-cleavage domains of plant viroid and virusoid RNA, the "hairpin" (Rossi J J et al. AIDS Research and Human Retroviruses 8:183–9, 1992). The hammerhead consists of three stems and a catalytic center, all containing 13 conserved nucleotides:

```
                                               (SEQ ID NO:44)
5'GAAACNNNNNNGUHNNNNNNNNNNNNNCUGANNNNNNNNNNNNNNGA3'

3'5'
Catylyst Strand --> N-N <-- Substrate Strand
                    N-N
                    N-N
                    C-G
                    A-U      Cleavage Site
                   A      X /
                   A         NNNNNN3'
            N      G         NNNNNN5'
         N    NNNNN       C
         N    NNNNN       U
            N     A     G
                G   A
                  N
```

Ribozymes, like protein enzymes, require specific structures for their catalytic activity. Natural catalytic centers may be formed by contiguous regions on the RNA or by regions separated by a large number of nucleotides. Cleavage by hammerhead ribozyme occurs 3' to the GUX triplet where X can be C, U, or A, generating 2', 3'-cyclic phosphate and 5' hydroxyl termini. The essential constituents of the hammerhead can be on separate molecules, with one strand serving as a catalyst and the other as a substrate. RNA sequences containing only the conserved cleavage domain (GUX) can serve as compatible substrates (Sarver, et al, Science 247, 1222–5 1990). Ribozymes have been attempted, with successes to various extent, as potential therapeutic agents for acquired immunodeficiency syndrome (AIDS) against gag (Sarver, et al. ibid), integrase (Sioud et al, Proc Natl Acad Sci USA 88, 7303–7, 1991); vif (Lorentzen et al, Virus Genes 5, 17–23, 1991); and other sequences (Goodchild et al, Arch Biochem Biophys 284, 386–91, 1991). Ribozymes cleavage activity can be directed to cut very specifically pre-determined sequences on RNA molecules, both in cell-free system and within the cells, by the flanking RNA sequences which are antisense to the ribozyme's target, i.e., a ribozyme relies on antisense sequences to locate its positions of cutting. The antisense sequence binds to the mRNA and the ribozyme cuts the mRNA.

Construction of Antisense-Ribozyme HIV-1 Proviral Clones

The addition of RNA cleavage activity of ribozymes to increase the antisense virus's ability to neutralize a naturally occurring virus was accomplished by incorporating one or more of the 22-nucleotide-long catalytic domains, containing the consensus sequence, into the antisense sequences. The ribozyme(s) will cut the tat mRNA at 3' to the triplets GUX (X=A, C or U) which occur eight times in the area that has been turned antisense. While three of the GUX have actually been chosen, any one of them is potentially a target site for ribozyme cleavage. The designing procedure is illustrated as follows:

The original sequences between nt 5775 and 5986 of pX are as below. The bold-type area is where the inversion occurs.

```
5774    HXB2VPR<--|    5795                                    |-->TAT    (SEQ ID NO:43)
|  \/sa           |    |                                       |
CAGAATTGGGTGTCGACATAGCAGAATAGGCGTTACTCGACAGAGGAGAGCAAGAAATGGAGCCA
Q   N   W   V   S   T   *
    R   I   G   C   R   H   S   R   I   G   V   T   R   Q   R   R   A   R   N   G   A
                                                                            M   E   P

NLVPR<-|
       |
GTAGATCCTAGACTAGAGCCCTGGAAGCATCCAGGAAGTCAGCCTAAAACTGCTTGTACCAATTG

S   R   S   *
    V   D   P   R   L   E   P   W   K   H   P   G   S   Q   P   K   T   A   C   T   N   C
                                                                                    5965
                                                                                    |
CTATTGTAAAAAGTGTTGCTTTCATTGCCAAGTTTGTTTCATAACAAAAGCCTTAGGCATCTCCT

Y   C   K   K   C   C   F   H   C   Q   V   C   F   I   T   K   A   L   G   I   S
|-->REV           5986
|      \/sa       |
ATGGCAGGAAGAAGCGGA-3'
  M   A   G   R   S   G

Y   G   R   K   K   R

Below is the sense version of the double-stranded DNA sequence:

5774    HXB2VPR<--|                                                        (SEQ ID NO:43)
|  \/sa           |
CAGAATTGGGTGTCGACATAGCAGAATAGGCGTTACTCGACAGAGGAGAGCAAGAAATGGAGCCA
gtcttaacccacagctgtatcgtcttatccgcaatgagctgtctcctctcgttctttacctcggt
           Sal -I GTAGATCCTAGACTAGAGCCCTGGAAGCATCCAGGAAGTCAGCCTAAAACTGCTTGTACCAATTG
catctaggatctgatctcgggaccttcgtaggtccttcagtcggattttgacgaacatggttaac CTATTGTAAAAAGTGTTGCTTTCATTGCCAAGTTTGTTTCATAACAAAAGCCTTAGGCATCTCCT
gataacatttttcacaacgaaagtaacggttcaaacaaagtattgttttcggaatccgtagagga
                                                                E c
|-->REV           5986
|      \/sa       |
ATGGCAGGAAGAAGCGGA-3'
taccgtccttcttcgcct-5'
  o - N I
```

Below is the sense version of the RNA sequence, with all GTX underlined.

```
CAGAAUUGGGUGUCGACAUAGCAGAAUAGGCGUUACUCGACAGAGGAGAGCAAGAAAUGGAGCCA    (SEQ ID NO:45)

GUAGAUCCUAGACUAGAGCCCUGGAAGCAUCCAGGAAGUCAGCCUAAAACUGCUUGUACCAAUUG
```

-continued
CUAUUGUAAAAAGUGUUGCUUUCAUUGCCAAGUUUGUUUCAUAACAAAAGCCUUAGGCAUCUCCU

AUGGCAGGAAGAAGCGGA-3'

Below is the antisense version of the DNA sequence in antisense proviral clone pXE-a:

```
5774   HXB2VPR<--|                                                    (SEQ ID NO:46)
|   \/sa         |
CAGAATTGGGTGTCGACATAGagatgcctaaggcttttgttatgaaacaaacttggcaatgaaag
gtcttaacccacagctgtatcTCTACGGATTCCGAAAACAATACTTTGTTTGAACCGTTACTTTC
             Sal -I
caacacttttttacaatagcaattggtacaagcagttttaggctgacttcctggatgcttccaggg
GTTGTGAAAAATGTTATCGTTAACCATGTTCGTCAAAATCCGACTGAAGGACCTACGAAGGTCCC ctctagtctaggatctactggctccatttcttgctctcctctgtcgagtaacgcctattctgCCT
GAGATCAGATCCTAGATGACCGAGGTAAAGAACGAGAGGAGACAGCTCATTGCGGATAAGACgga
                                                                  E c
|-->REV        5986
|     \/sa        |
ATGGCAGGAAGAAGCGGA-3'
taccgtccttcttcgcct-5'
  o - N I
``` and below is the antisense version of the RNA sequence:

CAGAAUUGGGUGUCGACAUAGAGAUGCCUAAGGCUUUUGUUAUGAAACAAACUUGGCAAUGAAAG  (SEQ ID NO:47)

CAACACUUUUUACAAUAGCAAUUGGUACAAGCAGUUUUAGGCUGACUUCCUGGAUGCUUCCAGGG

CUCUAGUCUAGGAUCUACUGGCUCCAUUUCUUGCUCUCCUCUGUCGAGUAACGCCUAUUCUGCCU

AUGGCAGGAAGAAGCGGA-3'

When the antisense RNA encounters the natural (sense) tat mRNA, it will bind the natural (sense) tat mRNA and block the translation of tat mRNA into TAT protein.

```
                               *     *
CAGAAUUGGGUGUCGACAUAGAGAUGCCUAAGGCUUUUGUUAUGAAACAAACUUGGCAAUGAAAG  (SEQ ID NO:47)
                     |||||||||||||||||||||||||||||||||||||||||||||
AGGCGAAGAAGGACGGUAUCCUCUACGGAUUCCGAAAACAAUACUUUGUUUGAACCGUUACUUUC  (SEQ ID NO:45)

*         *              *                *
CAACACUUUUUACAAUAGCAAUUGGUACAAGCAGUUUUAGGCUGACUUCCUGGAUGCUUCCAGGG
||||||||||||||||||||||||||||||||||||||||||||||||||||||||||||||||
GUUGUGAAAAAUGUUAUCGUUAACCAUGUUCGUCAAAAUCCGACUGAAGGACCUACGAAGGUCCC

*                                   *
CUCUAGUCUAGGAUCUACUGGCUCCAUUUCUUGCUCUCCUCUGUCGAGUAACGCCUAUUCUGCCU
||||||||||||||||||||||||||||||||||||||||||||||||||||||||||||||||
GAGAUCAGAUCCUAGAUGACCGAGGUAAAGAACGAGAGGAGACAGCUCAUUGCGGAUAAGACGAU
```

AUGGCAGGAAGAAGCGGA-3'

ACAGCUGUGGGUUAAGAC-5'

Upper Line: Antisense RNA sequence, written 5'- - - >3';
Lower line: Natural mRNA sequence, written 3'- - - >5', with all potential ribozyme cleavage sites underlined. A 22-base catalytic domain, 5'-CUGAUGAGGCCUGAUGGCCGAA-3' (SEQ ID NO:48), or in the secondary structure form of

```
        G A       U
```

-continued
```
     U     GGCC     G
     A     CCGG     A
     G      G       U
            U   A
             C A
``` can be fixed into the antisense sequence to replace any one or more of the nucleotides indicated by a "*" on top. The ribozyme will thus be targeted to cut the sense RNA 3' to the triplet "GTX" where "X" stands for "A", "G" or "U".

See Example 3 for a detailed description of construction of ribozyme proviral clones.

Construction of Antisense-Ribozyme HIV-2 Proviral Clones

A ribozyme catalytic sequence can also be incorporated into the HIV-2 antisense clone to cleave (GUU) the tat mRNA at any one or more positions of 5883–5885 (GUC), 6011–6013 (GUA), 6032–6034 (GUC), and 6041–6043 (GUU). These are the four GUX positions in the area to be turned antisense (nt 5793–6062).

Construction of Antisense-Ribozyme SIV Proviral Clones

A similar ribozyme sequence can also be implanted to the antisense SIV proviral clone(s) to target mRNA at positions 5767–5769 (GUA) or/and positions 6063–6065 (GUU). The 5767–5769 GUA triplet is 18 bases before the tat initiation codon. The cleavage, however, deprives the tat mRNA of leading sequence necessary for its translation into protein. The 6063–6065 GUU sequence is at SIV tat amino acids 59–60.

Construction of Antisense-Ribozyme Viral Clones of Other Viruses

The same or similar ribozyme sequences can also be fixed into other antisense viral clones wherever a "GUX" triplet is present in the sense mRNA sequences.

COMPARISONS OF NATURAL, ANTISENSE AND ANTISENSE-RIBOZYME HIV-1 MOLECULAR CLONES

A. Natural (Wild Type) HIV-1 Clones (pXE or pX or pNL4-3)

1. Contain intact LTRs, gag, pol, env, vif, vpr, tat, rev, vpu, nef genes.
2. Replication competent: produce normal virions.
3. Infectious: virions carry on their envelope membranes normal gp120 and gp41. Gp120 is capable of attaching to CD4 molecules (act as receptors for the viruses) and introducing the virion contents into the cells.
4. Pathogenic: viral components are synthesized, virions assembled and exported, resulting in the death of host cells.
5. Cause Illness: mainly because of CD4(+) lymphocyte depletion and subsequent opportunistic infections and tumors.

B. Antisense HIV-1 Molecular Clones (pXE-a & pXE-b)

1. Contain intact LTRs, gag, pol, env, vif, vpr, vpu genes. A portion of tat-1 gene is inverted. Rev is either intact (pXE-a) or abraded (pXE-b).
2. Replication impaired, but can be complemented by transactivating factor tat (and rev for pXE-b). In the existence of tat (and rev) protein to provide necessary regulation, replication capability is restored, though may not necessarily be complete. Virus particles can be formed which are otherwise normal except carrying inverted tat-1 sequence (and the mutated rev initiation codon).
3. The assembled virions are infectious in that they can bind to CD4 molecules, can be taken up by CD4(+) cells, be reverse-transcribed into double-stranded DNA, be transported to the cell nucleus, and be integrated into the cellular genome. In the event that the cells are activated and dividing, the integrated proviral sequences will also be copied into each daughter cell along with the cellular DNA. In the absence of the essential tat (and rev) protein(s), however, the proviral sequences cannot produce virus particles.
4. These replication-impaired HIV-1 derivatives are non-pathogenic.
5. They cannot make people ill.
6. In the presence of tat (and rev) protein(s), provided either by expression vectors or by naturally infecting HIV-1 viruses, the inert provirus can be re-activated; the provirus can be transcribed into mRNA and translated into proteins with the exception of tat and, in some cases, vpr and rev.
7. The expressed antisense tat RNA can bind and inactivate the natural sense tat mRNA, consequently inactivating the natural viruses.

C. Antisense-Ribozyme HIV-1 Molecular Clones (pXE-ar, pXE-br)

1. Contain intact LTRs, gag, pol, env, vif, vpr, vpu genes. A portion containing tat-1 is inverted and one or more ribozyme catalytic domains have been inserted in such portion. The rev gene is either intact (pXE-ar) or inactivated (pXE-br).
2. Replication impaired, but can be complemented by transactivation factor, tat (and rev for pXE-br). In the existence of tat (and rev) protein to provide necessary regulation, replication capability are restored, though may not necessarily be complete. Virus particles can be formed which are otherwise normal except carrying inverted tat-1 sequence and one or more ribozyme catalytic domains (with mutated rev initiation codon in pXE-br).
3. The assembled virions are infectious in that they can bind to CD4 molecules, can be taken up by CD4(+) cells, be reverse-transcribed into double-stranded DNA, be transported to the cell nucleus, and be integrated into the cellular genomes. In the event that the cells are activated and dividing, the integrated proviral sequences will also be copied into each daughter cell. In the absence of the essential tat (and rev) protein(s), however, the proviral sequences cannot produce the virus particles.
4. Non-pathogenic.
5. They cannot make people ill.
6. In the presence of tat (and rev) protein(s), provided either by expression vectors or by naturally infecting HIV-1 viruses, the inert provirus can be re-activated; the provirus can be transcribed into mRNA and translated into proteins with the exception of tat and, in some cases, vpr and rev.
7. The expressed antisense tat RNA can bind and inactivate the natural sense tat mRNA. Moreover, the tat mRNA is cut into pieces by the incorporated ribozymes. Consequently the natural viruses is eliminated.

Antisense/Ribozyme Clone Functionality Tests

1. The natural HIV-1 clone, pX or pXE, when transfected alone, produces viruses which replicate rapidly as indicated by RT (reverse transcriptase) activity, viral protein detection, syncytium formation, and cell killing—positive control.
2. The antisense/ribozyme recombinant clone(s), when transfected alone, do not produce virus, as indicated by background RT activity, no syncytium formation, normal cell growth.
3. An antisense/ribozyme clone produces viruses if co-transfected with a positive TAT-expression clone, or if transfected into cells constitutively expressing TAT protein, as indicated by raised RT activity, viral protein detection, possible syncytium formation, possible cell killing.
4. Supernatant from cultures co-transfected with an antisense/ribozyme clone and a TAT-expressing clone contains virus particles (EM visible, RT activity, p24 ELISA, etc.).
5. Virus particles contained in the co-transfected supernatant can be taken up by CD4(+) cells.

If the cells contain TAT, new viruses are produced as indicated by RT, p24, and cytopathagenesis.

If the cells do not contain TAT, they will grow normally, even though the antisense/ribozyme proviral sequences might have integrated into the cellular DNA.

6. An antisense/ribozyme recombinant clone co-transfected with a natural clone results in a period of time during which both clones are replicating as indicated by a considerable rise of RT activity, viral protein detection, syncytium formation, even cell killing. After that period of time, however, RT drops gradually, syncytia disappear, and cells grow normally.

7. If both supernatants from natural clone-transfected culture and antisense/ribozyme recombinant clone-transfected culture is used to infect normal CD4+ cells, infection occurs and production of virus occurs briefly, then the cells gradually return to normal with the viruses eliminated.

8. Virus particles can be purified from cell cultures co-transfected with a antisense/ribozyme proviral clone and a TAT-expression clone.

9. Introduction of purified antisense/ribozyme viruses into cell cultures producing natural viruses results in gradual decrease and eventual cessation of natural virus as well as antisense/ribozyme virus production.

10. When purified antisense/ribozyme virus particles are administered to patients infected with HIV-1, virus production decreases gradually and eventually ceases.

Individualization of Antisense/Ribozyme Viruses

Individualization of an antisense/ribozyme virus is achieved with an individualized antisense/ribozyme proviral clone. An individualized antisense/ribozyme proviral clone is constructed by replacing a selected section of a gene of an existing functional proviral clone with an individualized antisense/ribozyme fragment. This individualized antisense/ribozyme fragment is synthesized in a single PCR reaction, using as the template the nucleic acid specimen from a particular patient which contains integrated or unintegrated viral sequences. The antisense/ribozyme primers are the same as detailed above. The PCR products are used to replace the corresponding section of a gene in the existing proviral molecular clone. The resultant recombinant clone has an individualized antisense/ribozyme fragment which, when expressed into RNA forms a perfect duplex with (and in the case of an antisense ribozyme virus—cleaves the mRNA of) the particular virus strain infecting the particular patient. With individualization of antisense/ribozyme virus, it is only necessary to individualize the antisense/ribozyme fragment. The other components of the viral genome are those of any existing functional virus clone available.

Individualization for treatment is a distinct advantage of the subject invention. Mutation permits the AIDS virus to escape and finally destroy the human immune system. Individualization of antisense/ribozyme viruses is an effective way to neutralize the mutating AIDS viruses.

The individualization method discussed are applicable to HIV-1, HIV-2 and SIV viruses as well as other viruses (as discussed above).

Complemental Gene Expression Vectors

The antisense/ribozyme molecular clones, as mentioned above, cannot replicate on their own. In the case of HIV, when the antisense/ribozyme clones are transfected into cells, the cells do not make viruses because the clones are missing the tat (and rev) gene function(s). For the cells to be able to make viruses, the cells must provide tat (and rev) gene protein(s) which are necessary for, but are not produced by, the antisense/ribozyme clones. Gene-expression molecular clones have therefore been designed to provide tat, optionally rev and vpr, functions which are missing from the antisense/ribozyme clones because of sequence inversion. pX and pNL are used for the construction of gene-expression clones.

One of three following methods is employed.

The first method is to truncate major genes of HIV-1 except tat, rev and vpr (which overlap with each other). In practice the coding region for env is also kept intact along with the long terminal repeats (LTRs). The truncated clone, when introduced into cells, expresses tat and rev which trans-activate the antisense/ribozyme clones. Env and vpr proteins also are expressed which can help the antisense/ribozyme virus assembly.

The second method is to insert the tat (and rev as well) coding sequences into gene expression vectors driven by promoters from sources other than HIV-1.

The third option is to insert chemically synthesized tat-coding DNA sequence into one of the many gene expression vectors commercially available. Many gene-expression vectors are commercially available for expressing a cloned gene in mammalian cells. Such gene-expression vectors are described in detail in at least two laboratory manuals (Sambrook J, Fritsch E F & Maniatis T. Molecular Cloning, a laboratory manual, second edition, Cold Spring Harbor Laboratory Press, 1989, chapter 16; Kriegler M. Gene transfer and expression, a laboratory manual, Stockton press, 1990, chapter 2). The choice of a vector is based on the gene to be expressed and the host cells in which the gene will be expressed. For expressing HIV-1 TAT (and REV) proteins in CD4+ cell lines of human origin, for example, a retrovirus long terminal repeat (LTR)-driven gene-expression vector can be used (Rosen C A et al. 1986. J Virol 57:379–384; Vickers T et al. 1991. Nucleic Acids Res 19:3359–68; Rhodes A & James W. 1991. AIDS 5:145–51). An advantage of using HIV-1 LTR-driven gene-expression vectors to express HIV-1 TAT protein (Guyader M et al. 1987. Nature 326:662–9) is the reciprocal augmentation of the transcriptional activation and the gene-expression product. Other promoters which have been used to express HIV genes are SV40 regulatory sequences (Arya S K et al. 1985. Science 229:69–73; Dillon P J et al. 1991. J Virol 65:4490–3), Drosophila hsp70 promoter (Schweinfest C W et al. 1988. Gene 71:207–10), SR-a (Mallon R et al. 1990. J Virol 64:6282–5).

For selecting only the expression-vector-containing cells, neomycin resistance gene expression cassettes are inserted into the expression vectors. With the inclusion of antibiotic G418 in the culture medium, only those cells transfected with Neo(r) gene (together with HIV-1 tat and other genes) survive, assuring that every cell in the culture has the capability to support the making of antisense/ribozyme viruses.

All principles and methodologies presented for constructing the gene expression vector clones apply to HIV-2, SIV and other viruses as well as to HIV-1. Examples of construction of these vectors are shown in the Examples 5–7 below.

Antisense/Ribozyme Virus Producer Cell Lines

Transfection of either an antisense/ribozyme proviral clone or a tat-expression vector alone into cells does not result in the production of antisense/ribozyme virus. It is necessary to introduce both the antisense/ribozyme proviral clone and the tat-expression vector into the same cell in order for the antisense/ribozyme virus particles to be made. Practically, a tat-expression vector can be transfected into a cell line (Jurkat for example), selected by including G418 in the culture medium, tested for the production of tat and other proteins, then kept in cell culture or frozen for later transfection of the antisense/ribozyme proviral clones. It has been shown that the Jurkat cell line can be stably transfected with a plasmid that constitutively expresses antisense tat RNA even after eight months in cell cultures (KostR et al, Clin Res; 38(2):278A, 1990). It can be expected that the same cell line will also be able to be stably transfected with a plasmid that constitutively expresses sense tat RNA (mRNA) and protein.

Advantageously, the antisense/ribozyme virus producer cell lines for HIVs are CD4+ and of human origin. CD4 positivity ensures that, once the cell line has been engineered to constitutively express TAT (and/or other) protein, the antisense/ribozyme virions released from one cell will be capable of infecting other cells in the culture, enabling quick production of large quantities of antisense/ribozyme virus stocks. Human origin of the producer cell lines minimizes the possibility of provoking adverse immunoreactions by the antisense/ribozyme inocula. Advantageously, the above mentioned Jurkat, a CD4+ lymphoid cell line frequently utilized to express HIV-1 genes (Venkatesh L K et al. PNAS 87:8746–50,1990; Maitra R K et al. Virology 182:522–33, 1991), will be a good choice as an antisense/ribozyme virus producer cell line. Other CD4+ lymphoid cell lines such as H9, HUT78, MT4, CEM, MOLT4, and monocyte/macrophage cell lines such as U937, THP-1, AND GCT, frequently used in HIV-1 transfection experiments (Aldovini A & Feinberg M B. 1990. Transfection of molecularly cloned HIV genomes. in Techniques in HIV Research, A. Aldovini & B C Walker, eds, Stockton Press, pp147–175), are useful for HIV-1 antisense/ribozyme virus producer cell lines. Some adherent cell lines, that are normally not susceptible to infection yet capable of expressing HIV genes and producing virus upon transfection, are regularly employed in studies of HIV gene regulation (ibid). The HeLa cell lines, for example, either CD4-negative (Mallon R et al. J Virol. 64:6282–5,1990) or better CD4-positive, HeLaCD4 and HeLaT4+ (Schroder H C et al. FASEB J 4:3124–30, 1990) can be used for HIV-1 antisense/ribozyme virus producer cell lines. The 293 human embryonic kidney cell line, which supports high levels of expression of HIV trans-activation (Jakobovits A et al. EMBO J 9:1165–70, 1990), is another good host cell line.

For producer antisense/ribozyme virions for other viruses, other cell lines are chosen according to considerations known to those skilled in the art.

Cell line transfected with one of the HIV-1 tat-expression vectors are cultured in medium supplemented with antibiotic G418, and the surviving cells are tested for the production of HIV-1 proteins.

pX-CSneo transfected cells express vpr, tat, rev, and env proteins; while pX-neo transfected cells express no viral proteins.

SFneo-t/r(+) transfected cells express tat protein, and possibly rev protein; while SFneo-t/r(−) or SFneo transfected cells produce no HIV-1 protein.

SFneo-tat(+) transfected cells express tat protein only; while SFneo-tat(−) or SFneo transfected cells produce no HIV-1 protein at all.

If TAT activity is detected (by CAT assay), the transfected cells are propagated. Part of the cells are frozen. Another part are passed through long-term culture to test the stability of TAT gene expression. Cells stably expressing TAT and other proteins are used as antisense/ribozyme virus producer cells and are transfected with HIV-1 antisense/ribozyme clones. The doubly transfected cells are assayed for the production of HIV-1 viruses (antisense/ribozyme viruses). P24 ELISA, RT activity and electronic microscopy are employed to detect the presence of the viruses.

If the cells are producing the viruses, the conditioned medium (containing virus particles), optionally concentrated, is used to infect CD4(+) cells (H9, Molt-3, CEM, U937, etc.) and the production of progeny viruses is assayed.

When a cell line is transfected with an HIV-2 or SIV TAT-expression vector, it becomes an antisense/ribozyme virus producer cell line for HIV-2 or SIV.

Compositions of the Invention

Also comprehended by the invention are pharmaceutical compositions comprising therapeutically effective amounts of products of the invention together with suitable diluents, preservatives, solubilizers, emulsifiers, adjuvants and/or carriers useful in antiviral therapy. A "therapeutically effective amount" as used herein refers to that amount which provides a therapeutic effect for a given condition and administration regimen. Where a product of the subject invention is used as a prophylactic medicine, a therapeutically effective amount is that amount which prevents infection.

The compositions of the invention are liquids, gels, ointments, or lyophilized or otherwise dried formulations and include diluents of various buffer content (e.g., Tris-HCl., acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc. or into liposomes, microemulsions, micelles, unilamellar or multilamellar vesicles, erythrocyte ghosts, spheroplasts, skin patches, or other known methods of releasing or packaging pharmaceuticals. Such compositions will influence the physical state, solubility, stability, rate of in vivo release, and rate of in vivo clearance of the antisense and/or antisense-ribozyme viruses. The choice of composition will depend on the physical and chemical properties of the antisense and/or antisense-ribozyme viruses. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitory factors or permeation enhancers for various routes of administration, including parenteral, pulmonary, nasal, topical (skin or mucosal) and oral.

The invention also comprises compositions including one or more additional antiviral factors such as 3'-azidodeoxythymidine (AZT) or dideoxycytidine (ddC). The administration of antisense and/or antisense-ribozyme viruses with other antiviral agents, is temporally spaced or given together. The route of administration may be intravenous, intraperitoneal sub-cutaneous, intramuscular, topical, oral or nasal.

Antisense and/or antisense-ribozyme viruses of the invention may be "labelled" by association with a detectable marker substance (e.g., radiolabeled, enzyme labelled, or biotinylated).

The following examples are offered to more fully illustrate the invention, but are not to be construed as limiting the scope thereof.

THE EXAMPLES

Example 1

PCR STRATEGY FOR ANTISENSE CONSTRUCTION

A PCR strategy was developed to accomplish the sequence inversion (flip-over). For ease in understanding, the amino acid sequences encoded by the DNA is not shown and the complementary DNA strand (negative strand, antisense strand, written in small characters) is shown for the DNA sequence of the tat gene to be inverted:

```
CAGAATTGGGTGTCGACATAGCAGAATAGGCGTTACTCGACAGAGGAGAGCAAGAAATGGAGCCA    (SEQ ID NO:43)
gtcttaacccacagctgtatcgtcttatccgcaatgagctgtctcctctcgttctttacctcggt
          Sal -I GTAGATCCTAGACTAGAGCCCTGGAAGCATCCAGGAAGTCAGCCTAAAACTGCTTGTACCAATTG
catctaggatctgatctcgggaccttcgtaggtccttcagtcggattttgacgaacatggttaac CTATTGTAAAAAGTGTTGCTTTCATTGCCAAGTTTGTTTCATAACAAAAGCCTTAGGCATCTCCT
gataacattttcacaacgaaagtaacggttcaaacaaagtattgttttcggaatccgtagagga ATGGCAGGAAGAAGCGGA-3'
taccgtccttcttcgcct-5'
Eco-NI
```

A special design for the primers (antisense primers) is essential for the recombinant PCR strategy to be successful and convenient. Basically, each antisense primer comprises two parts which are separated in the natural DNA sequence: an annealing sequence corresponding to one end of the 171-bp fragment to be turned over and a 15-base tail from the other side immediately beyond the area to be inverted. The 5' antisense primer is to anneal to the negative strand at the beginning of the sequence to be inverted, but it has a 15-base tail whose sequence corresponds to the 15 bases right after the sequence to be inverted where the unique EcoNI site is located. On the other hand, the 3' antisense primer is to anneal to the positive strand at the end of the sequence to be inverted, but it has a 15-base tail whose sequence corresponds to the 15 bases right before the sequence to be inverted where the unique SalI site is located. In the primers shown below, capital letters represent sequence from positive (sense) strand and small letters are used for the negative (antisense) strand.

```
                      E c o - N I                                                    (SEQ ID NO:43)
                   tcttcctgccatagg
                              CAGAATAGGCGTTACTCGACAGAG
CAGAATTGGGTGTCGACATAGCAGAATAGGCGTTACTCGACAGAGGAGAGCAAGAAATGGAGCCA
gtcttaacccacagctgtatcgtcttatccgcaatgagctgtctcctctcgttctttacctcggt
          Sal -I GTAGATCCTAGACTAGAGCCCTGGAAGCATCCAGGAAGTCAGCCTAAAACTGCTTGTACCAATTG
catctaggatctgatctcgggaccttcgtaggtccttcagtcggattttgacgaacatggttaac E c
CTATTGTAAAAAGTGTTGCTTTCATTGCCAAGTTTGTTTCATAACAAAAGCCTTAGGCATCTCCT
gataacattttcacaacgaaagtaacggttcaaacaaagtattgttttcggaatccgtagagga
                                                gtattgttttcggaatccgtaga
                                                                    GAT o - N I
ATGGCAGGAAGAAGCGGA-3'
taccgtccttcttcgcct-5'

ACAGCTGTGGGT
 Sal -I
```

Primers for flip-over PCR are as follows. The numbering is of the natural proviral sequences.

```
Trev 5795, 5' antisense primer:
          REV<---|
        EcoNI    |
```

```
                             -continued
    TCT TCC TGC CAT AGG CAG AAT AGG CGT TAC TCG ACA GAG  (SEQ ID NO:1)
    -------------------|------------------------------>
    TAILrev(5980-5966)    Annealing sequence(5795-5818)
```

SEQ ID NO:1

TCTTCCTGCC ATAGGCAGAA TAGGCGTTAC TCGACAGAG                39

```
    Tvpr 5965, 3' antisense primer:
                              5960 5952
         VPR<---|              |    |
         Sal-I  |              S a u - I
    TGG GTG TCG ACA TAG AGA TGC CTA AGG CTT TTG TTA TG  (SEQ ID NO:2)
    -------------------|------------------------------>
    TAILvpr(5780-5794)    Annealing sequence(5965-5943)
```

SEQ ID NO:2

TGGGTGTCGA CATAGAGATG CCTAAGGCTT TTGTTATG                 38

The PCR procedure can be illustrated as follows.

Original positive strand of pX, written from 5' to 3', (SSS) and (EEE) respectively stand for SalI site and EcoNI site on positive strand.

```
++++++++SSS++++++++++++++++++++++++++++EEE++++++++
```

Original negative (antisense) strand of pX, written from 3' to 5', (sss) and (eee) respectively stand for SalI site and EcoNI site on negative strand.

```
++++++++sss++++++++++++++++++++++++++++eee++++++++
```

5' antisense primer, whose annealing part is of positive strand while whose tail is of negative strand with EcoNI (eee) site.

```
                              ---eee+++++++++>
```

3' antisense primer, whose annealing part is of negative strand while whose tail is of positive strand with SalI (SSS) site.

```
                              <---------SSS+++
```

Align the antisense primers with both strands of the original pX which is to be utilized as template in the recombinant PCR reactions.

```
            ---eee+++++++++>
++++++++SSS+++++++++++++++++++++++++++++++++++++++++++++++EEE++++++++
--------sss-----------------------------------------eee--------
```

The PCR procedure can be illustrated as follows.

```
++++++++SSS+++++++++++++++++++++++++++++++++++++++++++++++EEE++++++++
--------sss-----------------------------------------eee--------
                          | PCR
                          | Denaturation
                          v
++++++++SSS+++++++++++++++++++++++++++++++++++++++++++++++EEE++++++++

--------sss-----------------------------------------eee--------
                          | PCR
                          | Annealing
                          v
++++++++SSS+++++++++++++++++++++++++++++++++++++++++++++++EEE++++++++
                                              <---------SSS+++

---eee+++++++++>
--------sss-----------------------------------------eee--------
                          | PCR
                          | Extension
                          v
++++++++SSS+++++++++++++++++++++++++++++++++++++++++++++++EEE++++++++
--------sss---------------------------<---------SSS+++

---eee+++++++++>+++++++++++++++++++++++++++++++++EEE++++++++
--------sss-----------------------------------------eee--------
                          | PCR
```

```
                         -continued
                         | Second Cycle
                         v
++++++++++SSS++++++++++++++++++++++++++++++++++++++++++++EEE++++++++
--------sss----------------------------------<---------SSS+++

---eee++++++++++>++++++++++++++++++++++++++++++++++++++sss---
--------SSS----------------------------------<---------SSS+++

---eee++++++++++>+++++++++++++++++++++++++++++++++++EEE++++
    +++EEE-----------------------------------<---------SSS+++

---eee++++++++++>++++++++++++++++++++++++++++++++++++EEE++++++++
--------sss----------------------------------------------eee--------
                         | PCR
                         | Third Cycle
                         v
++++++++++SSS++++++++++++++++++++++++++++++++++++++++++++EEE+++++++
--------sss----------------------------------<---------SSS+++

---eee++++++++++>++++++++++++++++++++++++++++++++++++++sss---
--------sss----------------------------------<---------SSS+++

---eee++++++++++>++++++++++++++++++++++++++++++++++++++sss---
    +++EEE-----------------------------------<---------SSS+++

--------SSS----------------------------------<---------SSS+++

---eee++++++++++>+++++++++++++++++++++++++++++++++++EEE++++++++
    +++EEE-----------------------------------<---------SSS+++

---eee++++++++++>++++++++++++++++++++++++++++++++++++++sss---
    +++EEE-----------------------------------<---------SSS+++

---eee++++++++++>+++++++++++++++++++++++++++++++++++EEE++++++++
    +++EEE-----------------------------------<---------SSS+++

---eee++++++++++>+++++++++++++++++++++++++++++++++++EEE++++++++
--------sss----------------------------------------------eee--------
                         | PCR
                         | 35 cycles
                         | The majority of the fragments
                         | will be
                         v
    ---eee++++++++++>++++++++++++++++++++++++++++++++++++++sss---
    +++EEE-----------------------------------<---------SSS+++
                                                              40
```

To align this fragment with the original strands in term of the restriction sites SalI and EcoNI, it will be necessary to turn the PCR fragment around.

```
    Original strands:

++++++++++SSS++++++++++++++++++++++++++++++++++++++++++++EEE++++++++
--------sss----------------------------------------------eee--------

PCR inverted fragment:

+++SSS---------->--------------------------------EEE+++
    ---sss++++++++++++++++++++++++++++++++++<++++++++++++++eee---
```

The actual sequence of the PCR inverted fragment (antisense fragment):

```
5'-TGGGTGTCGACATAGagatgcctaaggcttttgttatgaaacaaacttggcaatgaaag  (SEQ ID NO:3)
3'-acccacagctgtatcTCTACGGATTCCGAAAACAATACTTTGTTTGAACCGTTACTTTC
        Sal -I caacactttttacaatagcaattggtacaagcagttttaggctgacttcctggatgcttccaggg
GTTGTGAAAAATGTTATCGTTAACCATGTTCGTCAAAATCCGACTGAAGGACCTACGAAGGTCCC E c
```

```
                                        -continued
ctctagtctaggatctactggctccatttcttgctctcctctgtcgagtaacgcctattctgCCT
GAGATCAGATCCTAGATGACCGAGGTAAAGAACGAGAGGAGACAGCTCATTGCGGATAAGACgga o - N I
  ATGGCAGGAAGA-3'
  taccgtccttct-5'

SEQ ID NO:3 (ANTISENSE FRAGMENT)

TGGGTGTCGA CATAGAGATG CCTAAGGCTT TTGTTATGAA ACAAACTTGG           50

CAATGAAAGC AACACTTTTT ACAATAGCAA TTGGTACAAG CAGTTTTAGG          100

CTGACTTCCT GGATGCTTCC AGGGCTCTAG TCTAGGATCT ACTGGCTCCA          150

TTTCTTGCTC TCCTCTGTCG AGTAACGCCT ATTCTGCCTA TGGCAGGAAG A        201
```

Antisense molecular clones are made by "swapping" the original SalI-EcoNI fragment on pXE with the PCR-made SalI-EcoNI fragment.

```
       Original strands:

++++++++SSS+++++++++++++++++++++++++++++++++++++++++++++++EEE++++++++
--------sss-------------------------------------------eee--------

PCR inverted fragment:

+++SSS---------->----------------------------EEE+++
    ---sss+++++++++++++++++++++++++++++++++<+++++++++++++eee---
                             | Restriction digestion
                             | with SalI & EcoNI
                             | simultaneously
                             v
++++++++S SS++++++++++++++++++++++++++++++++++++++++++++E EE+++++++
--------ss s------------------------------------------ee e-------

++++++++S SS++++++++++++++++++++++++++++++++++++++++++++E EE+++++++
--------ss s------------------------------------------ee e-------
                             | Ligation with
                             | T4 DNA ligase
                             | (Note the bold-type fragments
                             |  will be ligated together.)
                             v
++++++++SSS---------->----------------------------EEE++++++++
--------sss+++++++++++++++++++++++++++++++++<+++++++++++++eee--------
```

In the antisense proviral clone, the sequence between nt 5774 and 5986 will become as follows. Note in the flipped-over bold-type area the negative (antisense) strand has been linked to the original positive (sense) strand.

During transcription where the positive strand of the double-stranded DNA is transcribed into RNA, the above shown sequence will be transcribed into antisense RNA against natural tat mRNA.

```
5774   HXB2VPR<--|
|  \/sa          |
CAGAATTGGGTGTCGACATAGagatgcctaaggcttttgttatgaaacaaacttggcaatgaaag  (SEQ ID NO:46)
gtcttaacccacagctgtatcTCTACGGATTCCGAAAACAATACTTTGTTTGAACCGTTACTTTC
         Sal -I caacacttttacaatagcaattggtacaagcagttttaggctgacttcctggatgcttccaggg
GTTGTGAAAAATGTTATCGTTAACCATGTTCGTCAAAATCCGACTGAAGGACCTACGAAGGTCCC ctctagtctaggatctactggctccatttcttgctctcctctgtcgagtaacgcctattctgCCT
GAGATCAGATCCTAGATGACCGAGGTAAAGAACGAGAGGAGACAGCTCATTGCGGATAAGACgga
                                                              E c

|-->REV        5986
|     \/sa       |
ATGGCAGGAAGAAGCGGA-3'
taccgtccttcttcgcct-5'
  o - N I
```

```
CAGAAUUGGGUGUCGACAUAGAGAUGCCUAAGGCUUUUGUUAUGAAACAAACUUGGCAAUGAAAG   (SEQ ID NO:47)

CAACACUUUUUACAAUAGCAAUUGGUACAAGCAGUUUUAGGCUGACUUCCUGGAUGCUUCCAGGG

CUCUAGUCUAGGAUCUACUGGCUCCAUUUCUUGCUCUCCUCUGUCGAGUAACGCCUAUUCUGCCU

AUGGCAGGAAGAAGCGGA-3'
```

The antisense RNA will bind complementarily to the natural (sense) tat mRNA and block the translation of tat mRNA into TAT protein.

```
CAGAAUUGGGUGUCGACAUAGAGAUGCCUAAGGCUUUUGUUAUGAAACAAACUUGGCAAUGAAAG   (SEQ ID NO:47)
                     ||||||||||||||||||||||||||||||||||||||||||||
AGGCGAAGAAGGACGGUAUCCUCUACGGAUUCCGAAAACAAUACUUUGUUUGAACCGUUACUUUC

CAACACUUUUUACAAUAGCAAUUGGUACAAGCAGUUUUAGGCUGACUUCCUGGAUGCUUCCAGGG
|||||||||||||||||||||||||||||||||||||||||||||||||||||||||||||||||
GUUGUGAAAAAUGUUAUCGUUAACCAUGUUCGUCAAAAUCCGACUGAAGGACCUACGAAGGUCCC

CUCUAGUCUAGGAUCUACUGGCUCCAUUUCUUGCUCUCCUCUGUCGAGUAACGCCUAUUCUGCCU
|||||||||||||||||||||||||||||||||||||||||||||||||||||||||||||||||
GAGAUCAGAUCCUAGAUGACCGAGGUAAAGAACGAGAGGAGACAGCUCAUUGCGGAUAAGACGAU

AUGGCAGGAAGAAGCGGA-3'

ACAGCUGUGGGUUAAGAC-5'

Upper Line: Antisense RNA sequence, written 5'-->3';
    Lower line: Natural  mRNA sequence, written 3'-->5'.
```

By binding together, the natural mRNA and the antisense RNA block each other from being translated into proteins, resulting in the depletion of tat protein, and subsequently all viral proteins, for the natural as well as the antisense HIV-1 viruses.

For eliminating the rev gene at the same time, the rev initiation codon was changed into a non-initiation one:

```
                        5962               5980
                         |                  |
Original sequence        ATCTCCTATGGCAGGAAGA-3'   (SEQ ID NO:49)
EcoNI recognition            CCTNNNNNAGG
Rev initiation codon             ATG
Changed to                       AGG
Rev(-) sequence          ATCTCCTAGGGCAGGAAGA-3'   (SEQ ID NO:50)
New AvrII site               CCTAGG
```

Primers for flip-over PCR are as follows. The numbering is of the natural sequences.

Trev(-) 5795 (name), 5' antisense primer

```
            REV<---|
        EcoNI      |
    TCT TCC TGC CCT AGG CAG AAT AGG CGT TAC TCG ACA GAG           (SEQ ID NO:4)
    ------------------|----------------------------->
    TAILrev-(5890-5966)  Annealing sequence(5795-5818)

SEQ ID NO:4

TCTTCCTGCC CTAGGCAGAA TAGGCGTTAC TCGACAGAG                        39
```

Tvpr 5965, 3'antisense primer, SEQ ID NO:2 as aforementioned.

```
                      5960 5952
```

```
                                           -continued
     VPR<---|             |         |
     Sal-I   |             S  a  u - I
     TGG GTG TCG ACA TAG AGA TGC CTA AGG CTT TTG TTA TG       (SEQ ID NO:2)
     ------------------|---------------------------->
     TAILvpr(5780-5794)  Annealing sequence(5965-5943)
```

The PCR procedure used was exactly the same as aforementioned. The actual sequence of the PCR inverted fragment (antisense fragment) using primers Trev(-) 5795 and Tvpr 5965 is as follows.

extracted with phenol-chloroform-isoamyl alcohol (25:24:1), precipitated with alcohol and resuspended in 20 μl of TE solution (10 mM Tris-HCl, pH 7.5 and 1 mM EDTA). The purified PCR product was then mixed with plasmid

```
5'-TGGGTGTCGACATAGagatgcctaaggcttttgttatgaaacaaacttggcaatgaaag   (SEQ ID NO:5)
3'-acccacagctgtatcTCTACGGATTCCGAAAACAATACTTTGTTTGAACCGTTACTTTC
       Sal -I caacacttttttacaatagcaattggtacaagcagttttaggctgacttcctggatgcttccaggg
GTTGTGAAAAATGTTATCGTTAACCATGTTCGTCAAAATCCGACTGAAGGACCTACGAAGGTCCC E   c
ctctagtctaggatctactggctccatttcttgctctcctctgtcgagtaacgcctattctgCCT
GAGATCAGATCCTAGATGACCGAGGTAAAGAACGAGAGGAGACAGCTCATTGCGGATAAGACgga
    o - N I
AGGGCAGGAAGA-3'
tcccgtccttct-5'
```

SEQ ID NO:5 [REV(-) ANTISENSE FRAGMENT]

| | | | | | |
|---|---|---|---|---|---|
| TGGGTGTCGA | CATAGAGATG | CCTAAGGCTT | TGGTTATGAA | ACAAACTTGG | 50 |
| CAATGAAAGC | AACACTTTTT | ACAATAGCAA | TTGGTACAAG | CAGTTTTAGG | 100 |
| CTGACTTCCT | GGATGCTTCC | AGGGCTCTAG | TCTAGGATCT | ACTGGCTCCA | 150 |
| TTTCTTGCTC | TCCTCTGTCG | AGTAACGCCT | ATTCTGCCTA | GGGCAGGAAG A | 201 |

Note that SEQ ID NO:5 is only a single base pair different from SEQ ID NO:3, i.e., the base at position 191 is a "T" in SEQ ID NO:3 but a "G" in SEQ ID NO:5.

Rev(-) antisense molecular clones can be made by replacing the original SalI-EcoNI fragment on pXE with the SalI-EcoNI fragment on SEQ ID NO:5.

The flip-over PCR system consisted of:

| | | |
|---|---|---|
| pX, 1 μg/ml | | 2 μl |
| Reaction buffer, 10x | | 5 μl |
| Tris-HCl, pH 8.3 | 500 mM | |
| KCl | 500 mM | |
| MgCl2 | 20 mM | |
| Gelatine | 0.05% | |
| dNTP, 2.5 mM each | | 3 μl |
| Primer Tvpr 5965, 60 μg/ml | | 2 μl |
| Primer Trev 5795, 60 μg/ml (or Trev[-]5795) | | 2 μl |
| AmpliTaq DNA polymerase, 5 u/μl (from Perkin Elmer Cetus) | | 0.2 μl |
| Double distilled water | | 35.8 μl |
| | | 50.0 μl |

The samples, with proper controls, were run on a DNA Thermal Cycler (Perkin Elmer Cetus) for 35 cycles each consisting of 94° C. for 20 seconds, 60° C. for 20 seconds and 74° C. for 30 seconds.

10 μl of each PCR product was run on agarose gel (NuSieve 3:1, FMC). The correct size of the PCR product is 201 base pairs, which was confirmed by agarose gel electrophoresis.

Each inverted PCR product (antisense fragment) was DNA of pXE and digested with both restriction enzymes SalI and EcoNI:

| | | |
|---|---|---|
| Inverted PCR product, extracted | | 5 μl |
| pXE, 500 μg/ml | | 2 μl |
| Reaction buffer, 10x | | 5 μl |
| Tris-acetate, pH 7.9 | 20 mM | |
| Magnesium acetate | 10 mM | |
| Potassium acetate | 50 mM | |
| DTT | 1 mM | |
| EcoNI, 15 u/μl, NEB | | 1 μl |
| Sal I, 10 u/μl, NEB | | 1 μl |
| Double distilled water | | 37 μl |
| | | 50 μl |

Incubation was at 37° C. for at least 3 hours.

Ten microliter of the digest was run on agarose gel to make sure that the digestion had been satisfactory. The digest was heat-inactivated at 65° C. for 10 minutes and used directly for ligation:

| | |
|---|---|
| Above digest, undiluted | 4 μl |
| Ligase reaction buffer, 5x | 4 μl |
| T4 DNA ligase, 1 u/μl, BRL | 1 μl |
| Double distilled water | 11 μl |
| | 20 μl |

Incubation was at 15° C. for at least 3 hours.

The PCR-derived SalI—EcoNI fragment, containing the inverted sequence and outnumbering the plasmid-derived SalI -EcoNI fragment, competitively inserted itself into the SalI and EcoNI sites of the plasmid molecule.

One microliter of the 10-fold dilution of the ligation was used to transform 20 μl of competent HB101 *E. Coli* cells according to the instruction of the manufacturer (BRL). Briefly, 1 μl of the diluted ligation was gently mixed with the cells in a 1.5 ml microcentrifuge tube. After placing in ice for 30 minutes, the cells were heat shocked at 42° C. for 45 seconds then quickly returned to ice for two more minutes. 180 μl of S.O.C. Solution (2% tryptone, 0.5% yeast extract, 10 mM NaCl, 2.5 mM KCl, 10 mM MgCl2, 10 mM MgSO4, 20 mM glucose) was added and mixed, then the tube was incubated at 37° C. with constant agitation for 1 hour. The cells were spread on LB agar plate supplemented with ampicillin to the final concentration of 50 μg/ml. The plate was incubated at 37° C. overnight. Colonies were picked into 2 ml LB medium supplemented with ampicillin (LBamp) in the final concentration of 50 μg/ml. The bacterial cultures were placed at 37° C. shaker-incubator overnight.

The bacteria were harvested and miniplasmid DNA extracted according to Sambrook, Fritsch and Maniatis (Molecular Cloning, a laboratory manual, second edition, Cold Spring Harbor Laboratory Press, 1989) with minor modifications as necessary. Briefly, 1.5 ml of each overnight culture was pipetted into a microcentrifuge tube and spun in tabletop microcentrifuge for 1 minute. The pellet was completely dispersed in 100 μl of Solution I (50 mM glucose, 25 mM Tris-HCl pH 8.0, 10 mM EDTA pH 8.0). After adding 200 μl of freshly prepared Solution II (0.2 N NaOH, 1% SDS), the tube was inverted several times to mix. 150 μl of cold Solution III (5 M potassium acetate 60 ml, glacial acetic acid 11.5 ml, H2O 28.5 ml) was added and the tube vortexed briefly. The tube was then microcentrifuged for 2 minutes, the supernatant transferred to a new tube and extracted once with phenol:chloroform:isoamylalcohol (25:24:1). Plasmid DNA was precipitated with 1 ml of 100% ethanol, washed once with 75% ethanol, air-dried and resuspended in 30 μl of TE solution (10 mM Tris-HCl pH 7.5, 1 mM EDTA).

Example 2

SCREENING FOR ANTISENSE MOLECULAR CLONES

Miniplasmids were screened for the antisense molecular clones primarily by restriction endonuclease digestion followed by agarose gel electrophoreses. The clone constructed with Trev(+) primer was named pXE-a, and the clone constructed with Trev(−) primer was named pXE-b.

Comparing the original with the antisense proviral molecular clones, the Sau-1 (Bsu36I) restriction enzyme site at the original position 5954 has been moved to position 5800 in the antisense clone. The different positions of this Sau-I site in the natural versus antisense clone is employed for easy screening for the antisense clones.

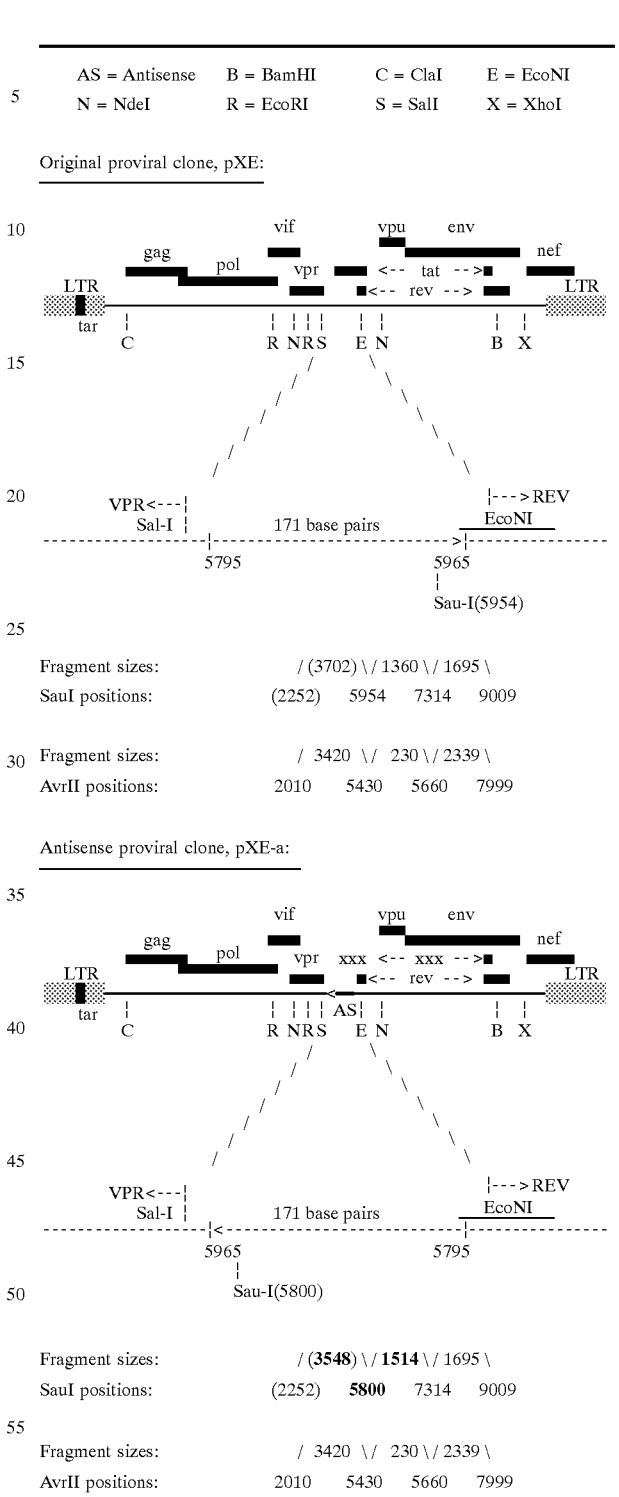

Antisense proviral clone, pXE-b:

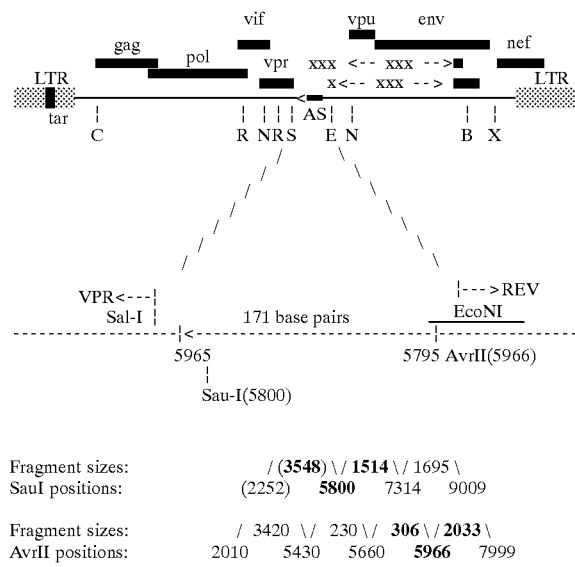

| Fragment sizes: | /(3548)\ | /1514\ | /1695\ | |
|---|---|---|---|---|
| SauI positions: | (2252) | 5800 | 7314 | 9009 |

| Fragment sizes: | /3420\ | /230\ | /306\ | /2033\ | |
|---|---|---|---|---|---|
| AvrII positions: | 2010 | 5430 | 5660 | 5966 | 7999 |

Restriction Digestion Patterns of Molecular HIV-1 (HXB2) Full-Length Clones and Major Subclones If the exact size of a particular fragment (band) is known, it is indicated by the exact number in bp (base pairs); If the exact size is not known, the estimated size is indicated by kb (kilobase). Bold-type are major clones or bands of interest for the particular restriction enzyme digestion.

| X = pX | E = pXE | Ea = pXE-a | Eb = pXE-b |
|---|---|---|---|
| Ear = pXE-ar | Ebr = pXE-br | N = pX-N | NE = pX-N-E |
| E2 = pX-E2 | E = pXE | XCS = pX-CS | |

Bsu36I (SauI)

| | X | E | Ea | Eb | Ear | Ebr | N | NE | E2 | E | XCS |
|---|---|---|---|---|---|---|---|---|---|---|---|
| 13.0kb | — | — | — | — | — | — | — | — | — | — | — |
| 8.5kb | | | | | | | | | | | — |
| 1695bp | — | — | — | — | — | — | — | — | — | — | — |
| 1514bp | | | | | —* | —* | | | | | |
| 1360bp | — | — | | | | | | | — | — | — |
| 0.7kb | — | — | — | — | — | — | — | — | — | — | — |

*This band is 21 base pairs larger than 1514 in pXE-ar and pXE-br because of the inclusion of the ribozyme catalytic sequence.

Bsu36I (SauI) is an excellent choice for distinguishing antisense/ribozyme proviral clones from the wild type clones (either pX or pXE). The 1360-base-pair wild type band changes to 1514 base pairs in antisense clones and to 1535 in antisense-monoribozyme clones. For the antisense-bi- and tri-ribozyme clones (not listed in the chart), this band will become 1556 (1514+21×2) and 1577 base pairs (1514+ 21×3). When samples are run side by side, the distinction between wild type clones and antisense/ribozyme clones is unmistakably obvious.

Note: The restriction sites are cited from GeneBank. The SauI site at nt 2252 is missing in pX as is in pXE. Missing with the site is the 3702-bp band.

Restriction digestion patterns of molecular HIV-1 (HXB2) full-length clones and major subclones.

AvrII

| | X | E | Ea | Eb | Ear | Ebr | N | NE | E2 | E | XCS |
|---|---|---|---|---|---|---|---|---|---|---|---|
| 3420bp | — | — | | | — | — | ? | ? | — | — | ? |
| 2339bp | — | — | | — | | | ? | ? | — | — | ? |
| 2033bp | | | — | — | | | | | | | |
| 306bp | | | — | — | | | | | | | |
| 230bp | — | — | — | — | — | — | ? | ? | — | — | — |

These restriction site reorganizations were confirmed by individual or combined enzyme digestion followed by agarose gel electrophoreses.

Armed with 171-base antisense RNA targeted to the essential tat gene of HIV-1 while still carrying all information of HIV-1, the antisense proviral clones pXE-a and pXE-b will make artificial antisense viruses which will neutralize the natural HIV-1 viruses.

Open Reading Frames in the Inverted Sequence

Analyzing the inverted 171 base pairs, two open reading frames (ORFs) were found with methionine initiation codon of 12 and 25 amino acids in length respectively. Global screening of PC/gene data bases has found no match, even allowing up to eight mismatches. The binding by natural mRNA blocks the formation of these putative proteins, just as it blocks the natural mRNA.

Open reading frames with methionine initiation codons:

```
5'-AGATGCCTAAGGCTTTTGTTATGAAACAAACTTGGCAATGAAAG  (SEQ ID NO:51)
     M  K                                  M  K

M  P  K  A  F  V  M  K  E  T  W  Q  *
   CAACACTTTTTACAATAGCAATTGGTACAAGCAGTTTTAGGCTGACTTCCTGGATGCTTCCAGGG
   A  T  L  F  T  I  A  I  G  T  S  S  F  R  L  T  S  W  M  L  P  G

CTCTAGTCTAGGATCTACTGGCTCCATTTCTTGCTCTCCTCTGTCGAGTAACGCCTATTCTG-3'
   L  *
```

The tat coding region in relation to the antisense area is shown in the sequence below. Bold-type represents inverted sequence. Nucleotide sequence in small characters is extension sequence beyond the PCR product.

```
5'-TGGGTGTCGACATAG=AGATGCCTAAGGCTTTTGTTATGAAACAAACTTGGCAATGAAAG  (SEQ ID NO:52)
TAT aa sequence:    <--I--G--L--A--K--T--I--F--C--V--Q--C--H--F-
"New protein"                                                  M  K "New protein"       M  P  K  A  F  V  M  K  E  T  W  Q  *
CAACACTTTTTACAATAGCAATTGGTACAAGCAGTTTTAGGCTGACTTCCTGGATGCTTCCAGGG
C--C--K--K--C--Y--C--N--T--C--A--T--K--P--Q--S--G--P--H--K--W--P-
 A  T  L  F  T  I  A  I  G  T  S  S  F  R  L  T  S  W  M  L  P  G CTCTAGTCTAGGATCTACTGGCTCCATTTCTTGCTCTCCTCTGTCGAGTAACGCCTATTCTG=CC
-E--L--R--P--D--V--P--E--M
 L  *

TATGGCAGGAAGAagcggagacagcgacgaagagctcatcagaacagtcagactcatcaagcttc
   M  A  G  R  S  G  D  S  D  E  E  L  I  R  T  V  R  L  I  K  L
   |-->rev protein (unchanged)

\/sd
tctatcaaagcagtaagtagtacatgt-3'
 L  Y  Q  S  S  K  *
```

Example 3

ANTISENSE-(MONO)RIBOZYME PROVIRAL CLONES

The 22-nucleotide-long catalytic domain was fixed into the antisense sequences to replace a "G", and thus was directed to cut the sense RNA at GUC which occurs once on tat mRNA:

```
CAGAAUUGGGUGUCGACAUAGAGAUGCCUAAGGCUUUUGUUAUGAAACAAACUUGGCAAUGAAAG  (SEQ ID NO:53)
                     ||||||||||||||||||||||||||||||||||||||||||||
AGGCGAAGAAGGACGGUAUCCUCUACGGAUUCCGAAAACAAUACUUUGUUUGAACCGUUACUUUC  (SEQ ID NO:54)

G A       U
                                  U     GGCC     G
                                  A     CCGG     A
                                  G    G     U
                                   U  A
                                    C A
CAACACUUUUUACAAUAGCAAUUGGUACAAGCAGUUUUAGGCA ACUUCCUGGAUGCUUCCAGGG
||||||||||||||||||||||||||||||||||||||||||| |||||||||||||||||||||
GUUGUGAAAAAUGUUAUCGUUAACCAUGUUCGUCAAAAUCCGACUGAAGGACCUACGAAGGUCCC

CUCUAGUCUAGGAUCUACUGGCUCCAUUUCUUGCUCUCCUCUGUCGAGUAACGCCUAUUCUGCCU
||||||||||||||||||||||||||||||||||||||||||||||||||||||||||||||||
GAGAUCAGAUCCUAGAUGACCGAGGUAAAGAACGAGAGGAGACAGCUCAUUGCGGAUAAGACGAU

AUGGCAGGAAGAAGCGGA-3'

ACAGCUGUGGGUUAAGAC-5'
```

Upper Line: Antisense RNA sequence, written 5'--->3', with one ribozyme catalytic domain incorporated.

Lower line: Natural mRNA sequence, written 3'--->5', with all potential ribozyme cleavage sites underlined.

The antisense RNA sequences with the incorporated ribozyme domain are written into DNA with complementary sequences added.

```
(5774)
|
CAGAATTGGGTGTCGACATAGAGATGCCTAAGGCTTTTGTTATGAAACAAACTTGGCAATGAAAG  (SEQ ID NO:55)
||||||||||||||||||||||||||||||||||||||||||||||||||||||||||||||||
GTCTTAACCCACAGCTGTATCTCTACGGATTCCGAAAACAATACTTTGTTTGAACCGTTACTTTC

|<---- Ribozyme ---->|
CAACACTTTTTACAATAGCAATTGGTACAAGCAGTTTTAGGCTCTGATGAGGCCTGATGGCCGAA
||||||||||||||||||||||||||||||||||||||||||||||||||||||||||||||||
```

-continued
```
GTTGTGAAAAATGTTATCGTTAACCATGTTCGTCAAAATCCGAGACTACTCCGGACTACCGGCTT ACTTCCTGGATGCTTCCAGGGCTCTAGTCTAGGATCTACTGGCTCCATTTCTTGCTCTCCTCTGT
||||||||||||||||||||||||||||||||||||||||||||||||||||||||||||||||
TGAAGGACCTACGAAGGTCCCGAGATCAGATCCTAGATGACCGAGGTAAAGAACGAGAGGAGACA (5896)
                                  |
CGAGTAACGCCTATTCTGCCTATGGCAGGAAGAAGCGGA-3'
|||||||||||||||||||||||||||||||||||||||
GCTCATTGCGGATAAGACGGATACCGTCCTTCTTCGCCT-5'
```

PCR technology was utilized to incorporate the ribozyme catalytic domain. To accomplish this, three primers were designed which correspond to the positions shown below.

```
5774   |------------- Tvpr 5965 ------------>|
       |    TGGGTGTCGACATAGAGATGCCTAAGGCTTTTGTTATG (SEQ ID NO:2)
CAGAATTGGGTGTCGACATAGAGATGCCTAAGGCTTTTGTTATGAAACAAACTTGGCAATGAAAG  (SEQ ID NO:55)
||||||||||||||||||||||||||||||||||||||||||||||||||||||||||||||||
GTCTTAACCCACAGCTGTATCTCTACGGATTCCGAAAACAATACTTTGTTTGAACCGTTACTTTC

|<---- Ribozyme ---->|
CAACACTTTTTACAATAGCAATTGGTACAAGCAGTTTTAGGCTCTGATGAGGCCTGATGGCCGAA
||||||||||||||||||||||||||||||||||||||||||||||||||||||||||||||||
GTTGTGAAAAATGTTATCGTTAACCATGTTCGTCAAAATCCGAGACTACTCCGGACTACCGGCTT
                                CATGTTCGTCAAAATCCGAGACTACTCCGGACTACCGGCTT
                                |<----------------- Pribo 5859-RB-5897 --

ACTTCCTGGATGCTTCCAGGGCTCTAGTCTAGGATCTACTGGCTCCATTTCTTGCTCTCCTCTGT
||||||||||||||||||||||||||||||||||||||||||||||||||||||||||||||||
TGAAGGACCTACGAAGGTCCCGAGATCAGATCCTAGATGACCGAGGTAAAGAACGAGAGGAGACA
TGAAGGACCTACGAAGGTC (SEQ ID NO:6)                       GAGACA
------------------|                                     |<----
                                (5986)
                                  |
CGAGTAACGCCTATTCTGCCTATGGCAGGAAGAAGCGGA-3'
|||||||||||||||||||||||||||||||||||||||
GCTCATTGCGGATAAGACGGATACCGTCCTTCTTCGCCT-5'
GCTCATTGCGGATAAGACGGATACCGTCCTTCT (SEQ ID NO:1)
-----Trev 5795 -----------------|
```

Primers "Tvpr 5965" and "Trev 5795" are actually SEQ ID NO:2 and SEQ ID NO:1 as aforementioned for antisense PCR. Therefore, only one more primer (Pribo) was needed to make the antisense-ribozyme proviral clone.

Pribo 5859-RB-5897, numbering is of the wild type sequences:

```
       CTGGAAGCATCCAGGAAGTTTCGGCCATCAGGCCTCATCAGAGCCTAAAACTGCTTGTAC
|                   ||<---- Ribozyme ---->||                    |
5859                5877                   5879                 5897
```

SEQ ID NO:6

CTGGAAGCAT CCAGGAAGTT TCGGCCATCA GGCCTCATCA GAGCCTAAAA                50

CTGCTTGTAC                                                           60

The following graphs illustrate how the Pribo primer inserts the ribozyme sequence into the PCR products. All three primers were put into the PCR system, with Pribo at a concentration about one tenth the concentration of either of the two end primers. pX was chosen as template. All full length clones, i.e., pXE, pXE2, pXE-a, pXE-b and pNL are all eligible for being templates and will result in the same PCR product, with the Pribo primer inserted its sequence into some of the amplified DNA fragments.

Original template sequence and primers:

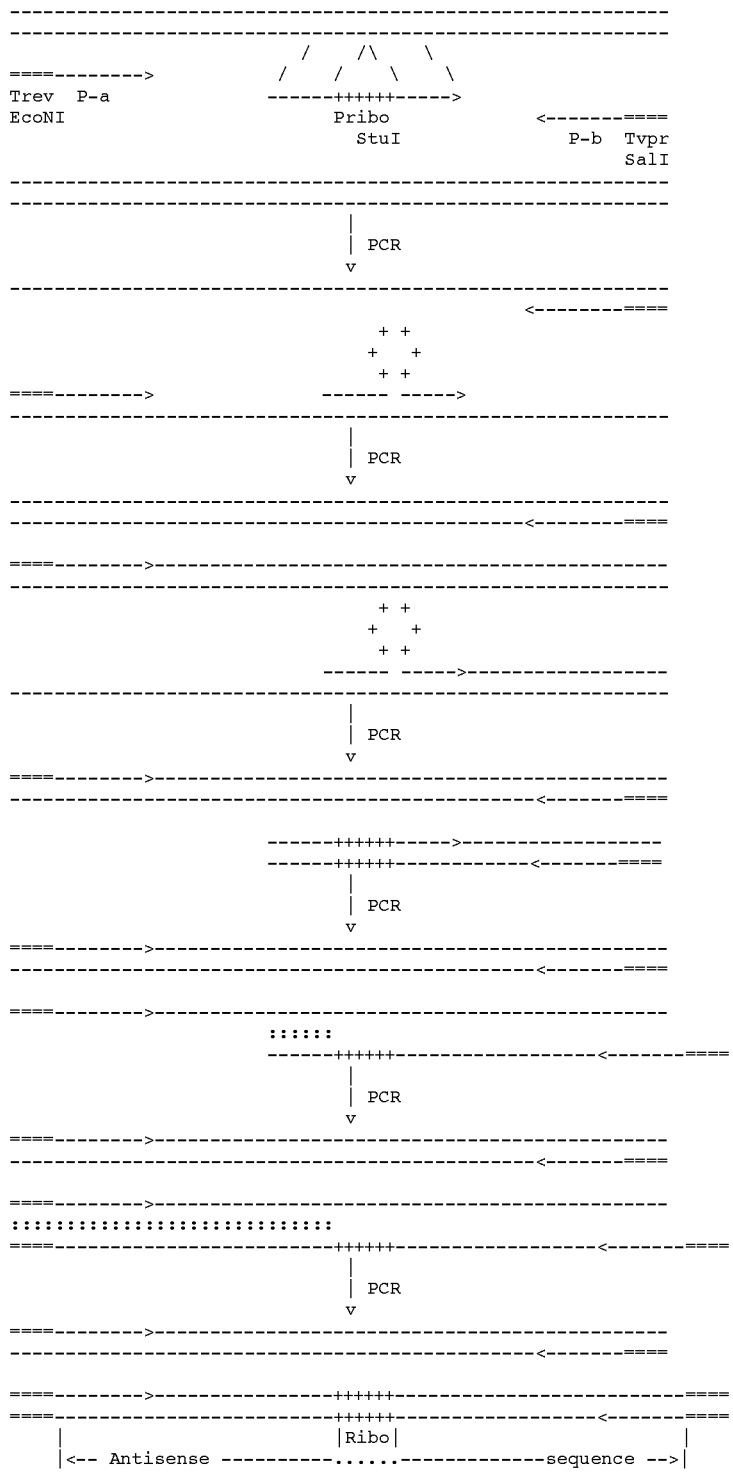
PCR product without ribozyme sequence is 201 bps, while that containing ribozyme sequence would be 222 bps as follows.
```
        Sal -I
5'-TGGGTGTCGACATAGAGATGCCTAAGGCTTTTGTTATGAAACAAACTTGGCAATGAAAG  (SEQ ID NO:7)
```

```
                       -continued
3'-ACCCACAGCTGTATCTCTACGGATTCCGAAAACAATACTTTGTTTGAACCGTTACTTTC Stu -I
CAACACTTTTTACAATAGCAATTGGTACAAGCAGTTTTAGGCTCTGATGAGGCCTGATGGCCGAA
GTTGTGAAAAATGTTATCGTTAACCATGTTCGTCAAAATCCGAGACTACTCCGGACTACCGGCTT
                                          |<---- Ribozyme ---->|

ACTTCCTGGATGCTTCCAGGGCTCTAGTCTAGGATCTACTGGCTCCATTTCTTGCTCTCCTCTGT
TGAAGGACCTACGAAGGTCCCGAGATCAGATCCTAGATGACCGAGGTAAAGAACGAGAGGAGACA

E c o - N I
CGAGTAACGCCTATTCTGCCTATGGCAGGAAGA-3'
GCTCATTGCGGATAAGACGGATACCGTCCTTCT-5'
```

SEQ ID NO:7

TGGGTGTCGA CATAGAGATG CCTAAGGCTT TTGTTATGAA ACAAACTTGG        50

CAATGAAAGC AACACTTTTT ACAATAGCAA TTGGTACAAG CAGTTTTAGG       100

CTCTGATGAG GCCTGATGGC CGAAACTTCC TGGATGCTTC CAGGGCTCTA       150

GTCTAGGATC TACTGGCTCC ATTTCTTGCT CTCCTCTGTC GAGTAACGCC       200

TATTCTGCCT ATGGCAGGAA GA                                     222

Where primer Trev(−), SEQ ID NO:4, is used instead of primer Trev(+), SEQ ID NO:1, the fragment will be 1 bp different, i.e., nt 212 "T" will be a "G":

SEQ ID NO:8
TGGGTGTCGA CATAGAGATG CCTAAGGCTT TTGTTATGAA ACAAACTTGG    50

CAATGAAAGC AACACTTTTT ACAATAGCAA TTGGTACAAG CAGTTTTAGG   100

CTCTGATGAG GCCTGATGGC CGAAACTTCC TGGATGCTTC CAGGGCTCTA   150

GTCTAGGATC TACTGGCTCC ATTTCTTGCT CTCCTCTGTC GAGTAACGCC   200

TATTCTGCCT AGGGCAGGAA GA                                 222 pXE together with "antisense-ribozyme PCR" product were digested with SalI and EcoNI simultaneously then self-ligated. The ligation was used to transform competent HB101 cells as detailed in the Examples. Miniplasmids were screened by digesting with StuI restriction enzyme (see below).

The genomic organization of the rev(+) antisense-(mono) ribozyme clone, pXE-ar(2):

[figure: genomic organization of pXE-ar(2) showing LTR, tar, gag, pol, vif, vpr, vpu, env, rev, nef, LTR with StuI sites at 484 and 964]

And the genomic organization of the rev(−) antisense-(mono)ribozyme clone, pXE-br(2)

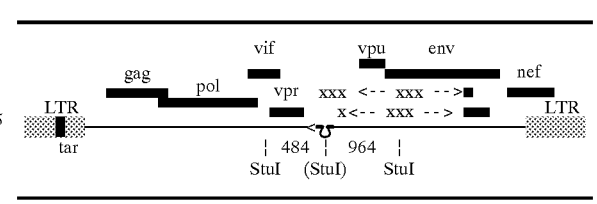

ANTISENSE-(MONO-, BI- or TRI-)RIBOZYME HIV-1 PROVIRAL CLONES

To guarantee at least one cleavage would occur to the sense tat mRNA even when there are mutations, multiple ribozymes targeted to different areas were arranged into the antisense sequences. Besides the "GUC" chosen, as mentioned above, two "GUA" triplets also were chosen as ribozyme targets. Potentially, four "GUU" and another "GUA" can also be chosen as targets if desired. The three sites chosen with their incorporated 22-base ribozyme catalytic domains are as follows. At the site of incorporation, the ribozyme sequence replaces a "G", or "U" of the antisense RNA.

```
CAGAAUUGGGUGUCGACAUAGAGAUGCCUAAGGCUUUUGUUAUGAAACAAACUUGGCAAUGAAAG    (SEQ ID NO:56)
                     ||||||||||||||||||||||||||||||||||||||||||||
AGGCGAAGAAGGACGGUAUCCUCUACGGAUUCCGAAAACAAUACUUUGUUUGAACCGUUACUUUC

G A     U                         G A     U
           U     GGCC   G                     U     GGCC   G
           A (1) CCGG   A                     A (2) CCGG   A
           G    G     U                       G    G     U
             U A                                U A
             C A                                C A
CAACACUUUU ACAAUAGCAAUUGGUACAAGCAGUUUUAGGCU ACUUCCUGGAUGCUUCCAGGG
||||||||||  |||||||||||||||||||||||||||||||   |||||||||||||||||||
GUUGUGAAAAAUGUUAUCGUUAACCAUGUUCGUCAAAAUCCGACUGAAGGACCUACGAAGGUCCC

G A     U
           U     GGCC   G
           A (3) CCGG   A
           G    G     U
             U A
             C A
CUCUAGUCUAGGAUC ACUGGCUCCAUUUCUUGCUCUCCUCUGUCGAGUAACGCCUAUUCUGCCU
|||||||||||||||  ||||||||||||||||||||||||||||||||||||||||||||||||
GAGAUCAGAUCCUAGAUGACCGAGGUAAAGAACGAGAGGAGACAGCUCAUUGCGGAUAAGACGAU

AUGGCAGGAAGAAGCGGA-3'

ACAGCUGUGGGUUAAGAC-5'

Upper       Antisense RNA sequence, written 5'-->3', with
Line:
            3 ribozyme catalytic domains incorporated.

Lower       Natural mRNA sequence, written 3'-->5', with
line:
            all potential ribozyme cleavage sites
            underlined.
```

Below, the antisense strand is written into DNA with complementary sequences. Note the ribozyme sequences. The first base pair corresponds to the wild type nt 5774 and the last 5986.

```
5774
|           Sal -I                                                   (SEQ ID NO:57)
CAGAATTGGGTGTCGACATAGAGATGCCTAAGGCTTTTGTTATGAAACAAACTTGGCAATGAAAG
GTCTTAACCCACAGCTGTATCTCTACGGATTCCGAAAACAATACTTTGTTTGAACCGTTACTTTC

Stu -I
CAACACTTTTCTGATGAGGCCTGATGGCCGAAACAATAGCAATTGGTACAAGCAGTTTTAGGCTC
GTTGTGAAAAGACTACTCCGGACTACCGGCTTTGTTATCGTTAACCATGTTCGTCAAAATCCGAG
          |<--- Ribozyme 1 --->|                                 |

Stu -I                                         BamH-I       St
TGATGAGGCCTGATGGCCGAAACTTCCTGGATGCTTCCAGGGCTCTAGTCTAGGATCCTGATGAG
ACTACTCCGGACTACCGGCTTTGAAGGACCTACGAAGGTCCCGAGATCAGATCCTAGGACTACTC
<--- Ribozyme 2 --->|                                    |<-- Riu -I                                                  E c o
GCCTGATGGCCGAAACTGGCTCCATTTCTTGCTCTCCTCTGTCGAGTAACGCCTATTCTGCCTAT
CGGACTACCGGCTTTGACCGAGGTAAAGAACGAGAGGAGACAGCTCATTGCGGATAAGACGGATA
bozyme 3 --->|

(5986)
 - N I          |
GGCAGGAAGAAGCGGA-3'
CCGTCCTTCTTCGCCT-5'
```

Primers needed to synthesize the DNA sequences are shown at the corresponding regions on the fragment to be made.

```
5774                             0--->
|    TGGGTGTCGACATAGAGATGCCTAAGGCTTTTGTTATG              CAATGAAAG
CAGAATTGGGTGTCGACATAGAGATGCCTAAGGCTTTTGTTATGAAACAAACTTGGCAATGAAAG
GTCTTAACCCACAGCTGTATCTCTACGGATTCCGAAAACAATACTTTGTTTGAACCGTTACTTTC

1--->
CAACACTTTTCTGATGAGGCCTGATGGCCGAAACAATAGCAATTGGTACAA
CAACACTTTTCTGATGAGGCCTGATGGCCGAAACAATAGCAATTGGTACAAGCAGTTTTAGGCTC
GTTGTGAAAAGACTACTCCGGACTACCGGCTTTGTTATCGTTAACCATGTTCGTCAAAATCCGAG
                                          CATGTTCGTCAAAATCCGAG
                                          <---2

AGGGCTCTAGTCTAGGATCCTGATGAG
TGATGAGGCCTGATGGCCGAAACTTCCTGGATGCTTCCAGGGCTCTAGTCTAGGATCCTGATGAG
ACTACTCCGGACTACCGGCTTTGAAGGACCTACGAAGGTCCCGAGATCAGATCCTAGGACTACTC
ACTACTCCGGACTACCGGCTTTGAAGGACCTACGAAGGTC

3--->
GCCTGATGGCCGAAACTGGCTCCATTTCTTGCT
GCCTGATGGCCGAAACTGGCTCCATTTCTTGCTCTCCTCTGTCGAGTAACGCCTATTCTGCCTAT
CGGACTACCGGCTTTGACCGAGGTAAAGAACGAGAGGAGACAGCTCATTGCGGATAAGACGGATA
                                GAGACAGCTCATTGCGGATAAGACGGATA
                                <---4>

(5986)
             |
GGCAGGAAGAAGCGGA-3'
CCGTCCTTCTTCGCCT-5'
CCGTCCTTCT
```

Primers needed to construct the above fragment are as follow (all written from 5' to 3', nucleotide position numbering is of wild type HXB2 sequences):

(0) Tvpr 5965

```
         .  .  .  .  .  .  .  .  .  .  .
       TGGGTGTCGACATAGAGATGCCTAAGGCTTTTGTTATG
       |              /\                     |
       5780      5794  5965                5943
```

SEQ ID NO:2 as depicted previously.

(1) Pribo 5930-RB-5892

```
         .  .  .  .  .  .  .  .  .  .  .  .  .  .  .  .
       CAATGAAAGCAACACTTTTCTGATGAGGCCTGATGGCCTAAACAATAGCAATTGGTACAA
       |              ||<---- Ribozyme ---->||            |
       5930           5912                 5910          5892
```

SEQ ID NO:9

CAATGAAAGC AACACTTTTC TGATGAGGCC TGATGGCCTA AACAATAGCA         50

ATTGGTACAA                                                    60

(2) Pribo 5859-RB-5897

```
         .  .  .  .  .  .  .  .  .  .  .  .  .  .  .  .
       CTGGAAGCATCCAGGAAGTTTCGGCCATCAGGCCTCATCAGAGCCTAAAACTGCTTGTAC
       |              ||<---- Ribozyme ---->||            |
       5859           5877                 5879          5897
```
SEQ ID NO:6 as depicted previouly for antisense-(mono)ribozyme fragment pXE-ar(2) & pXE-br(2).

(3) Pribo 5860-RB-5822

```
         .  .  .  .  .  .  .  .  .  .  .  .  .  .  .  .
       AGGGCTCTAGTCTAGGATCCTGATGAGGCCTGATGGCCGAAACTGGCTCCATTTCTTGCT
       |              ||<---- Ribozyme ---->||            |
       5860           5842                 5840          5822
```

SEQ ID NO:10

AGGGCTCTAG TCTAGGATCC TGATGAGGCC TGATGGCCGA AACTGGCTC         50

CATTTCTTGCT (4) Trev 5795

```
        .  .  .  .  .  .  .  .  .  .  .  .
        TCTTCCTGCCATAGGCAGAATAGGCGTTACTCGACAGAG
        |          /\                         |
        5980      5966 5795                 5818
```

SEQ ID NO:1 as depicted previously.

Ribozymes 1, 2 & 3, occurring alone[(1), (2), (3)] or in combinations [(1,2), (1,3), (2,3) (1,2,3)], were incorporated into the antisense sequence by a single PCR reaction.

| PCR system for REV(+) antisense-mono-, bi- or tri-ribozyme fragments: | | |
|---|---|---|
| pX, 1 ug/ml | | 2 µl |
| Reaction buffer, 10x | | 5 µl |
| Tris-HCl, pH 8.3 | 500 mM | |
| KCl | 500 mM | |
| MgCl2 | 20 mM | |
| Gelatine | 0.05% | |
| dNTP, 2.5 mM each | | 3 µl |
| (0)Tvpr 5965, 60 ug/ml | | 2 µl |
| (1)Pribo 5930-RB-5891, 6 ug/ml | | 2 µl |
| (2)Pribo 5859-RB-5897, 6 ug/ml | | 2 µl |
| (3)Pribo 5860-RB-5822, 6 ug/ml | | 2 µl |
| (4)Trev(+) 5795, 60 ug/ml | | 2 µl |
| Taq DNA polymerase, 5 u/µl (from Perkin Elmer Cetus) | | 0.2 µl |
| Double distilled water to | | 29.8 µl |

| Members of ribozymes incorporated | / | 1 | 2 | 3 | 1,2 | 1,3 | 2,3 | 1,2,3 |
|---|---|---|---|---|---|---|---|---|
| Total ribozyme copy incorporated | 0 | 1 | 1 | 1 | 2 | 2 | 2 | 3 |
| Size of PCR fragments (bp) | 201 | 222 | 222 | 222 | 243 | 243 | 243 | 264 |

Thermal cycling was for 50 cycles, each consisting of 94 degree C. for 20 seconds, 60 degree C. for 30 seconds and 74 degree C. for 30 seconds.

All three Pribo primers were present in the PCR system. Each Pribo primer, by chance, inserted its sequence (carrying one member of the ribozymes) into the PCR amplification product, which was a mixture of antisense-ribozyme fragments with 0, 1, 2 or 3 ribozyme domains incorporated in a random fashion.

The synthesized fragment, using primer Trev(+) 5795, SEQ ID NO:1, with all three members of ribozyme incorporated is 264-bp:

```
        TGGGTGTCGACATAGAGATGCCTAAGGCTTTTGTTATGAAACAAACTTGGCAATGAAAG    (SEQ ID NO:11)
        ACCCACAGCTGTATCTCTACGGATTCCGAAAACAATACTTTGTTTGAACCGTTACTTTC

Stu -I
        CAACACTTTTCTGATGAGGCCTGATGGCCGAAACAATAGCAATTGGTACAAGCAGTTTTAGGCTC
        GTTGTGAAAAGACTACTCCGGACTACCGGCTTTGTTATCGTTAACCATGTTCGTCAAAATCCGAG
                     |<--- Ribozyme --->|                                   |

Stu -I                                          BamH-I       St
        TGATGAGGCCTGATGGCCGAAACTTCCTGGATGCTTCCAGGGCTCTAGTCTAGGATCCTGATGAG
        ACTACTCCGGACTACCGGCTTTGAAGGACCTACGAAGGTCCCGAGATCAGATCCTAGGACTACTC
        <--- Ribozyme 2 --->|                                |<-- Riu -I                                                       E c o
        GCCTGATGGCCGAAACTGGCTCCATTTCTTGCTCTCCTCTGTCGAGTAACGCCTATTCTGCCTAT
        CGGACTACCGGCTTTGACCGAGGTAAAGAACGAGAGGAGACAGCTCATTGCGGATAAGACGGATA
        bozyme 3 --->|

.N - I
        GGCAGGAACA
        CCGTCCTTCT
```

```
                                                                       SEQ ID NO:11
        TGGGTGTCGA CATAGAGATG CCTAAGGCTT TTGTTATGAA ACAAACTTGG      50

CAATGAAAGC AACACTTTTC TGATGAGGCC TGATGGCCGA AACAATAGCA     100

ATTGGTACAA GCAGTTTTAG GCTCTGATGA GGCCTGATGG CCGAAACTTC     150

CTGGATGCTT CCAGGGCTCT AGTCTAGGAT CCTGATGAGG CCTGATGGCC     200

GAAACTGGCT CCATTTCTTG CTCTCCTCTG TCGAGTAACG CCTATTCTGC     250

CTATGGCAGG AAGA                                            264
```

Where primer Trev(-) 5795, SEQ ID NO:4, is used to replace primer Trev 5795, SEQ ID NO:1, in the above PCR system with everything else remaining the same, the fragment will be one base pair different, i.e., nt 254 "IT" will be a "G".

```
                                                SEQ ID NO:12

TGGGTGTCGA CATAGAGATG CCTAAGGCTT TTGTTATGAA ACAAACTTGG  50

CAATGAAAGC AACACTTTTC TGATGAGGCC TGATGGCCGA AACAATAGCA 100

ATTGGTACAA GCAGTTTTAG GCTCTGATGA GGCCTGATGG CCGAAACTTC 150

CTGGATGCTT CCAGGGCTCT AGTCTAGGAT CCTGATGAGG CCTGATGGCC 200

GAAACTGGCT CCATTTCTTG CTCTCCTCTG TCGAGTAACG CCTATTCTGC 250

CTAGGGCAGG AAGA                                        264
```

PCR fragments with any two ribozymes incorporated would be 243-bp long. Those with any one ribozyme would be 222-bp, and those without ribozyme would be 201-bp.

PCR products, together with plasmid pXE, were digested with SalI plus EcoNI then self-ligated. The ligations were used to transform competent HB101 cells as detailed earlier.

Alternatively, ribozyme domains are implanted one by one. Another alternative is to isolate the right DNA fragment after each PCR reaction, then use it as template for next round of PCR implantation/amplification.

Miniplasmids were screened by StuI digestion for various antisense-ribozyme clones. There are two StuI sites (nt 5404 and 6831) in the provirus sequences of the HXB2, producing a fragment of 1427 bps with the area to be turned antisense lying in between. This StuI fragment remains the same in antisense clones pXE-a and pXE-b. Since every ribozyme catalytic domain contains one StuI site, the implantation of one, two or three ribozymes will, respectively, interrupt the StuI fragment into two, three or four bands whose exact sizes can be calculated as indicated in the following graphics, where S=StuI site,
R1=Ribozyme 1,
R2=Ribozyme 2,
R3=Ribozyme 3.

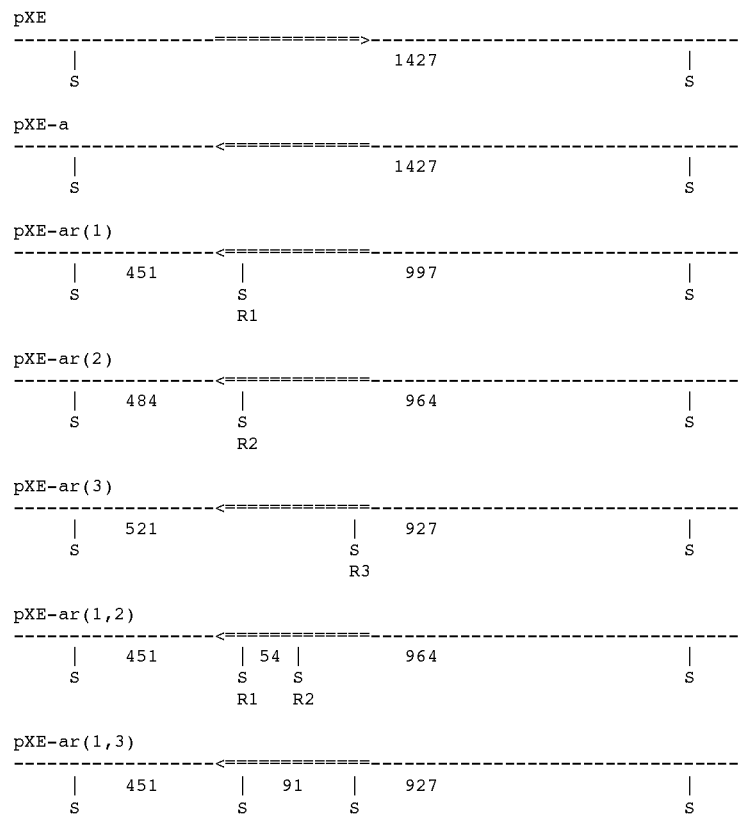

```
                     -continued
              R1           R3 pXE-ar(2,3)
-----------------<===========---------------------------------
     |    484        | 58 |      927                      |
     s               s    s                               s
                     R2   R3 pXE-ar(1,2,3)
-----------------<===========---------------------------------
     |    451     | 54 | 58 |    927                      |
     s            s    s    s                             s
                  R1   R2   R3
```

Clones of pXE-br series are exactly the same as those of pXE-ar for StuI digestion.

pX as well as pXE has two other StuI sites in the plasmid vector sequence. The internal proviral band (1427 bps) is the smallest. Moreover, the addition of the StuI sites in the ribozyme sequences results in even smaller bands. So the screening of the miniplasmids using StuI digestion proved to be handy and precise. Note the incorporation of one ribozyme has effectively inserted 21 bps into the sequence (plus 22-bp ribozyme, minus 1 bp the ribozyme replaced), causing the sum of base pairs with antisense-ribozyme clones to be larger than 1427.

Restriction Digestion Patterns of Molecular HIV-1 (HXB2) Full-Length Clones and Major Subclones If the exact size of a particular fragment (band) is known, it is indicated by exact number in bp (base pairs); If the exact size is not known, the estimated size will be indicated by kb (kilobase). Bold-type indicates major clones or bands of interest for the particular restriction enzyme digestion.

| | | | | | | | | | |
|---|---|---|---|---|---|---|---|---|---|
| X = pX | E = pXE | Ea = pXE-a | | Eb = pXE-b | | | | | |
| Ear = pXE-ar | Ebr = pXE-br | N = pX-N | | NE = pX-N-E | | | | | |
| E2 = pX-E2 | E = pXE | XCS = pX-CS | | | | | | | |
| StuI | | | | | | | | | |
| | X | E | Ea | Eb | Ear | Ebr | N | NE | E2 | E | XCS |
| 7.8kb | — | — — | — — | — | ? | ? | — | — | ? |
| 4.3kb | — | — — | — — | — | ? | ? | — | — | ? |
| 3.5kb | — | — — | — — | — | ? | ? | — | — | ? |
| 1427bp | — | — — | — | | | | — | — | — |
| 964bp | | | | — | — | | | | |
| 484bp | | | | — | — | | | | |

Note: The only antisense-ribozyme clones listed in all restriction digestion charts are pXE-ar(2) and pXE-br(2), shown as Ear and Ebr.

The "antisense-ribozyme HIV-1 proviral clones" pXE-ar series [constructed with Trev(+) primer] and pXE-br series [constructed with Trev(−) primer] are transfected into antisense/ribozyme virus producer cell line (see below). The virus particles produced (antisense-ribozyme viruses, ARV) are very powerful in inhibiting the replication of the natural HIV-1 viruses. In addition to the blockage activity as that of antisense viruses (ASV), the ARV also possess the ability to cleave the bound tat mRNA at 1 to 3 loci, rendering tat mRNA impossible to be translated into TAT protein.

Example 4

PREPARATION OF HIV-1 PLASMID CLONE FOR ANTISENSE/RIBOZYME PROVIRUS CONSTRUCTIONS

The construction of antisense/ribozyme HIV-1 proviral clones began with pX. pNL was employed for some special purposes.

Restriction site rearrangements became necessary after the area to be turned antisense was chosen and the restriction sites to be used were selected. Before the HIV-1 antisense/ribozyme proviral clones could be constructed with precision and convenience, it was necessary to obtain pXE. As discussed above, pXE contains a unique SalI site and a unique EcoNI site. The DNA sequence between these two unique sites can be replaced conveniently and precisely by antisense/ribozyme fragments, with the replacement products becoming antisense/ribozyme proviral clones.

Restriction mapping shows that there are three EcoNI sites in pX, yielding three bands of about 11.5, 3.8 and 1.7 kb respectively (see FIG. 2). Since it was necessary that the EcoNI site at nt 5966 be unique for convenient and precise antisense/ribozyme clone construction, the other two EcoNI sites were removed from the plasmid. The product of having the other two EcoNI sites removed is pXE.

pX contains another EcoNI site at nt 7631 in the proviral sequence (the corresponding site is also present in pNL). The third EcoNI site in pX is about 1.8 kb beyond the 3'-LTR of the proviral sequences, most likely located in the cellular sequence flanking the provirus. The EcoNI site outside the proviral sequence can be deleted by any means without having to worry about any adverse effect. The nt7631 EcoNI site, however, must be removed in a way that preserves the gene in which it resides.

The plasmid preparation strategy, in order to obtain pXE, was to protect the nt 5966 EcoNI site by removing the NdeI fragment (nt 5121–6402 containing the 5966 EcoNI site) from pX. The resultant clone (pX-N) was then subjected to point-mutation of nt 7631 EcoNI by recombinant PCR, followed by DNA polymerase filling-in to erase the EcoNI site outside the HIV-1 sequence. The resultant EcoNI-free subclone, pX-N-E, was reinstalled with the 5121–6402 NdeI fragment. The reestablished full-length proviral clone with the unique EcoNI site at nt 5966, pXE, was used as wild type HIV-1 plasmid and as parental plasmid for constructing all antisense/ribozyme HIV-1 proviral clones.

Similar rearrangements for restriction endonuclease sites are also made to pSE (HIV-2), pK102 (SIV) and p239F (SIV) for the precision and convenience in constructing antisense/ribozyme proviral clones.

This Example explains in detail the steps taken in preparing pXE, the restriction-site-rearranged HIV-1 wild type plasmid clone which has been used directly for the construction of HIV-1 antisense/ribozyme proviral clones.

REMOVAL OF ECONI SITE AT NT 5966 FROM PX (1) pX was digested with NdeI (CA|TATG) which occurs in HIV-1 sequence only at position 5121 and 6402, between which lies the HIV-1 EcoNI site at position 5966. Also in between is the unique SalI site at nt 5785.

| pX, 500 ug/ml | | 5 µl |
|---|---|---|
| Reaction buffer, 10x | | 5 µl |
| Tris-acetate, pH 7.9 | 20 mM | |
| Magnesium acetate | 10 mM | |
| Potassium acetate | 50 mM | |
| DTT | 1 mM | |
| Nde I, 20 u/µl, NEB | | 1 µl |
| Double distilled water | | 39 µl |
| | | 50 µl |

Incubation was in 37° C. for 1 hours.

(2) Ten microliter of the digest was run on agarose gel to ensure that the digestion was satisfactory. NdeI cuts pX twice, yielding two bands of 1281 bp and 16 kb respectively. The digest was heat-inactivated at 65° C. for 10 minutes and used directly for ligation:

| Above digest, undiluted | 4 µl |
|---|---|
| Ligase reaction buffer, 5x | 4 µl |
| T4 DNA ligase, 1 u/µl, BRL | 1 µl |
| Double distilled water | 11 µl |
| | 20 µl |

(3) 20 µl of competent *E. coli* cell strain HB101 was transfected with 1 µl of 10-fold dilution of the ligation according to the instruction of the manufacturer (BRL) of the competent cells with minor modifications as necessary. After incubating the LBamp agar plate in 37° C. overnight, single colonies were picked into 2 ml LB medium supplemented with ampicillin in the final concentration of 50 µg/ml (LBamp). The bacterial cultures were placed in 37° C. shaker-incubator overnight.

(4) The bacteria were harvested and miniplasmid DNA extracted according to Sambrook, Fritsch and Maniatis (Molecular Cloning, a laboratory manual, second edition, Cold Spring Harbor Laboratory Press, 1989) with minor modifications as necessary.

(5) Miniplasmids were digested with BglII. pX was also digested and used as control.

| Miniplasmid DNA, | | 3 µl |
|---|---|---|
| Reaction buffer, 10x | | 3 µl |
| Tris-HCl, pH 7.9 | 50 mM | |
| MgCl2 | 10 mM | |
| NaCl | 100 mM | |
| Dithiothreitol | 1 mM | |
| BglII, 8 u/µl | | 0.2 µl |
| Double distilled water | | 23.8 µl |
| | | 30.0 µl |

Incubation was at 37° C. for at least 3 hours.

For a cleaner agarose gel picture, ribonuclease A (RNase A, Sigma Chemicals) is regularly included at a final concentration of 50 µg/ml in the restriction enzyme digestion system for miniplasmids to destroy the contaminating RNAs. The resultant pictures were much better than restriction digestion without the RNase addition.

Compared to pX parental clone, the subclone with NdeI fragment deleted, pX-N, has one of the Bgl-II fragment (between positions 2095 and 7040) reduced from 4945 bp to a smaller fragment of 3663 bp.

```
▬■▬─────     ─────▒
|    | |     |   | | |
C    R N     N   E B X
```

| AS = Antisense | B = BamHI | C = ClaI | E = EcoNI |
|---|---|---|---|
| N = NdeI | R = EcoRI | S = SalI | X = XhoI |

Restriction digestion patterns of molecular HIV-1 (HXB2) full-length clones and major subclones.

If the exact size of a particular fragment (band) is known, the exact number in bp (base pairs) is indicated; if the exact size is not known, the estimated size is indicated by kb (kilobase). Bold-type is used for major clones or bands of interest for the particular restriction enzyme digestion.

| X = pX | E = pXE | Ea = pXE-a | Eb = pXE-b |
|---|---|---|---|
| Ear = pXE-ar | Ebr = pXE-br | N = pX-N | NE = pX-N-E |
| E2 = pX-E2 | E = pXE | XCS = pX-CS | |

| BglII | X | E | Ea | Eb | Ear | Ebr | N | NE | E2 | E | XCS |
|---|---|---|---|---|---|---|---|---|---|---|---|
| 4.9kb | = | = | = | = | = | = | — | — | = | = | — |
| 3663bp | | | | | | | — | — | | | |
| 3.0kb | — | — | — | — | — | — | — | — | — | — | — |
| 1622bp | — | — | — | — | — | — | — | — | — | — | — |
| 1430bp | — | — | — | — | — | — | — | — | — | — | — |
| 580bp | — | — | — | — | — | — | — | — | — | — | — |
| 507bp | — | — | — | — | — | — | — | — | — | — | — |

Restriction enzyme HindIII is also used to screen HIV-1 plasmids.

| HindIII | X | E | Ea | Eb | Ear | Ebr | N | NE | E2 | E | XCS |
|---|---|---|---|---|---|---|---|---|---|---|---|
| 5.1kb | | | | | | | — | — | | | |
| 4.3kb | = | = | = | = | = | = | — | — | = | = | — |
| 3.0kb | — | — | — | — | — | — | — | — | — | — | — |
| 2114bp | — | — | — | — | — | — | | | — | — | — |
| 1475bp | — | — | — | — | — | — | | | — | — | — |
| 1011bp | | | | | | | | | | | — |
| 627bp | — | — | — | — | — | — | — | — | — | — | — |
| 553bp | — | — | — | — | — | — | — | — | — | — | — |

Note: BglII and HindIII are routinely used in the construction procedures for HIV-1 plasmid clones. The enzymes are used either to do the first screening of miniplasmids or to further check the correctness of general structure of all HIV-1 plasmid clones. These digestion patterns should be referred to where a BglII or HindIII digestion is discussed.

(6) The deletion subclone pX-N had only two EcoNI sites both of which were to be removed. One was at nt 7631 while the other was about 1.8 kb beyond 3'-LTR of the HIV-1 sequence, most likely within the flanking cellular sequence. Digestion of pX-N with EcoNI yielded only two bands, about 12.0 and 3.8 kb respectively.

Restriction digestion patterns of molecular HIV-1 (HXB2) full-length clones and major subclones.

If the exact size of a particular fragment (band) is known, the exact number in bp (base pairs) is indicated; if the exact size is not known, the estimated size is indicated by kb (kilobase). Bold-type is used for major clones or bands of interest for the particular restriction enzyme digestion.

| | X | E | Ea | Eb | Ear | Ebr | N | NE | E2 | E | XCS |
|---|---|---|---|---|---|---|---|---|---|---|---|
| X = pX  E = pXE  Ea = pXE-a  Eb = pXE-b | | | | | | | | | | | |
| Ear = pXE-ar  Ebr = pXE-br  N = pX-N  NE = pX-N-E | | | | | | | | | | | |
| E2 = pX-E2  E = pXE  XCS = pX-CS | | | | | | | | | | | |
| EcoNI | | | | | | | | | | | |
| 17.0kb | | — | — | — | — | — | | — | | | |
| 15.7kb | | | | | | | * | | | | |
| 15.3kb | | | | | | | | | — | | |
| 12.0kb | | | | | | | — | | | | |
| 11.5kb | — | | | | | | | | | | |
| 7.0kb | | | | | | | | — | | | |
| 3.8kb | — | | | | | | | | — | | |
| 1665bp | — | | | | | | | | — | — | |

Note: This digestion pattern should be referred to while reading the text, especially in this Example at an EcoNI digestion. This Example fully details manipulations taken to achieve a wild type HIV-1 plasmid clone with unique EcoNI site at proviral position nt 5966 (pXE). The purpose of constructing pXE is to facilitate the subsequent construction steps for antisense/ribozyme proviral clones. * not cut by EcoNI

POINT-MUTATION OF ECONI SITE AT NT 7631 BY PCR (7) To erase the EcoNI site at nt 7631, a point mutation was made to change the nt 7633 "T" to a "G", without altering the encoded envelope protein sequence, since the original codon CCT and the changed codon CCG both encode for the same amino acid proline. (orig nt=original nucleotides; orig pt=original protein; chge to=change to; same pt=same protein; B primer=Bridging primer)

involves three (or more) primers instead of two in the traditional PCR system. For the elimination of the nt 7631 EcoNI site, the three primers used were as follows:

5'primer: EcoRI-down 4623

```
        GGGCGGGAATCAAGCAGG
        |-- 4623-4640 -->|
```

SEQ ID NO:13

GGGCGGGAAT CAAGCAGG                18

3'primer: HTX 8670

```
        TTGAGAATTCTAACAGCACTATTCTTTAG
        |------- 8670-8642 -------->|
```

SEQ ID NO:14

TTGAGAATTC TAACAGCACT ATTCTTTAG    29

Bridging primer: B 7633

```
        CCGAGATCTTCAGACCGGGAGGAGGAGATATGAGGG
        |----------- 7617-7652 ----------->|
```

SEQ ID NO:15

CCGAGATCTT CAGACCGGGA GGAGGAGATA TGAGGG    36

```
Orig nt:    GAG TCC GAG ATC TTC AGA CCT GGA GGA GGA GAT ATG AGG GAC    (SEQ ID NO:58)

Orig pt:     E   S   E   I   F   R   P   G   G   G   D   M   R   D

EcoNI:                                   CCT NNN NNA GG

Chge to:    GAG TCC GAG ATC TTC AGA CCG GGA GGA GGA GAT ATG AGG GAC    (SEQ ID NO:59)

Same pt:     E   S   E   I   F   R   P   G   G   G   D   M   R   D

B primer:       CC GAG ATC TTC AGA CCG GGA GGA GGA GAT ATG AGG G

EcoNI                                    CCG NNN NNA GG
removed:
```

The point-mutation and the EcoNI recognition site elimination were accomplished by a special PCR protocol of the subject invention, bridging PCR. Bridging PCR usually The sequential events of this Bridging PCR employed to introduce the point mutation into the sequence is illustrated as follows:

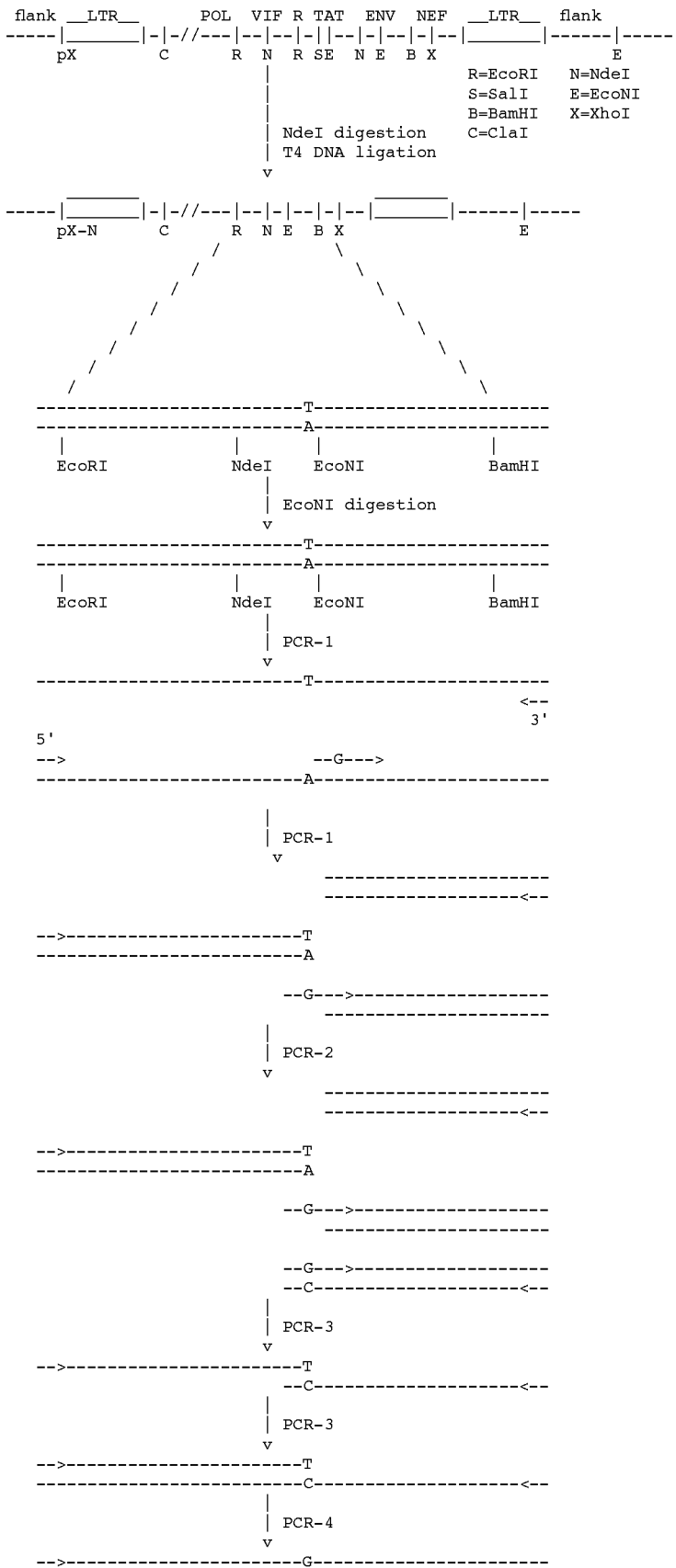

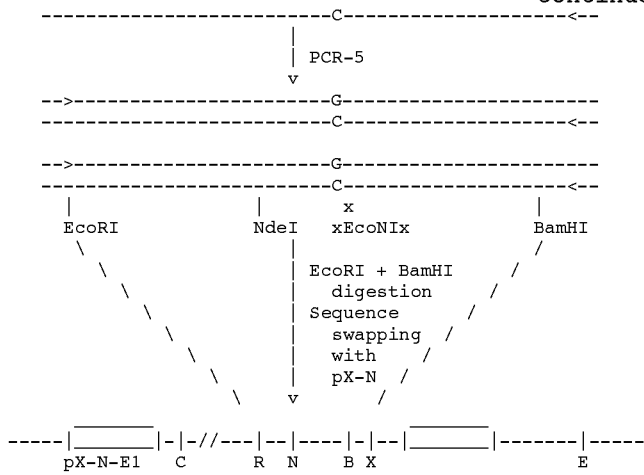

```
The bridging PCR reaction system consisted of:
    pX-N, EcoNI digest, about 50 ng/u1      2 µl
    Reaction buffer, 10x                    5 µl
        Tris-HCl, pH8.3     500 nM
        KCl                 500 nM
        MgCl2                20 nM
        Gelatin             0.05 %
    dNTP, 2.5 nM each                       3 µl
    5'primer, 4623-4640 60 ug/ml            2 µl
    3'primer, 8670-8670 60 ug/ml            2 µl
    "B"primer, 7617-7652 6 ug/ml            2 µl
    AmpliTaq DNA polymerase, 5 u/µl       0.2 µl
        (from Perkin Elmer-Cetus)
    Double distilled water                33.8 µl
                                          -------
                                          50.0 µl
```

The sample with proper controls was run on a DNA Thermal Cycler (Perkin Elmer Cetus) for 50 cycles each consisting of 94° C. for 20 seconds, 50° C. for 20 seconds and 74° C. for 120 seconds. 10 µl of the PCR product was run on agarose gel (NuSieve 3:1, FMC). The correct size of the PCR product should be 2766 base pairs, which was confirmed.

To establish whether the point mutation had been made, PCR products were digested with EcoNI. PCR product from reaction using undigested pX-N template, 5' and 3' (without bridging) primers, was cut into two bands of 1731 and 1035 bps. The bridging PCR product amplified with the system described above was not cut, indicating that the EcoNI site had been eliminated.

(8) The bridging PCR product was digested with EcoRI and BamHI simultaneously and the EcoRI-BamHI fragment of 2546 bp was used to replace the corresponding fragment of pX-N.

The bridging PCR product was extracted once with phenol-chloroform-isoamyl alcohol (25:24:1), mixed with plasmid DNA of pX-N and digested with both restriction enzymes EcoRI and BamHI:

| | |
|---|---|
| "Bridging" PCR product, extracted | 5 µl |
| pX-N, about 500 ug/ml | 2 µl |
| Reaction buffer, 10x | 5 µl |
| Tris-HCl, pH 8.0      20 mM | |
| MgCl2                 10 mM | |
| NaCL                 100 mM | |
| EcoRI, 10 u/µl, BRL | 1 µl |

-continued

| | |
|---|---|
| BamHI, 10 u/µl, BRL | 1 µl |
| Double distilled water | 36 µl |
| | 50 µl |

Incubation was at 37° C. for at least 3 hours.

Ten µl of the digest was run on agarose gel to make sure that the digestion had been satisfactory. The digest was heat-inactivated at 65° C. for 10 minutes and used directly for ligation:

| | |
|---|---|
| Above digest, undiluted | 4 µl |
| Ligase reaction buffer, 5x | 4 µl |
| T4 DNA ligase, 1 u/µl, BRL | 1 µl |
| Double distilled water | 11 µl |
| | 20 µl |

Incubation was at 15° C. for at least 3 hours.

One microliter of the 10-fold dilution of the ligation was used to transform 20 µl of competent HB101 cells. Colonies were picked and miniplasmids were extracted and digested by BglII as well as EcoNI. Successful recombinant clones (pX-N-E1) were cut only once by EcoNI instead of twice for pX-N; while the BglII digestion pattern of pX-N-E1 was the same as that for pX-N. In fact, pX-N-E1 had the same structure as pX-N except the nt 7633 "T" is changed to a "G". (see the restriction digestion patterns).

ELIMINATION OF OUTSIDE ECONI SITE BY POLYMERASE "FILL-IN"

(9) To abolish the remaining EcoNI site outside of the proviral sequence, pX-N-E1 (5 µg) was cut with EcoNI. The digest was purified by PCI extraction, ethanol precipitation and was resuspended in 50 µl of 1× TaqI DNA polymerase reaction buffer (diluted from 10× buffer of Perkin Elmer Cetus) with 50 uM of each dNTP and 1.0 unit of TaqI DNA polymerase. The mixture was placed in 70° C. for 1 minute ("fill-in" took place here) then subjected to PCI extraction (phenol-chloroform-isoamyl alcohol (25:24:1)). 4 µl of the mixture was used for ligation in a 20 µl system as in paragraph (8) above. One microliter of the 10-fold dilution of the ligation was used to transform 20 µl of competent DM1 cells which are dam methylase negative (GIBCO BRL). Colonies were picked and miniplasmids were extracted and digested by HindIII as well as EcoNI. Successful recombinant clones (pX-N-E) were not cut by EcoNI, but showed the same HindIII digestion pattern as pX-N and pX-N-E1 (see the restriction digestion patterns). In fact, pX-N-E has the same structure as pX-N except the nt 7633 "T" is changed to "G" and the outside EcoNI is eliminated.

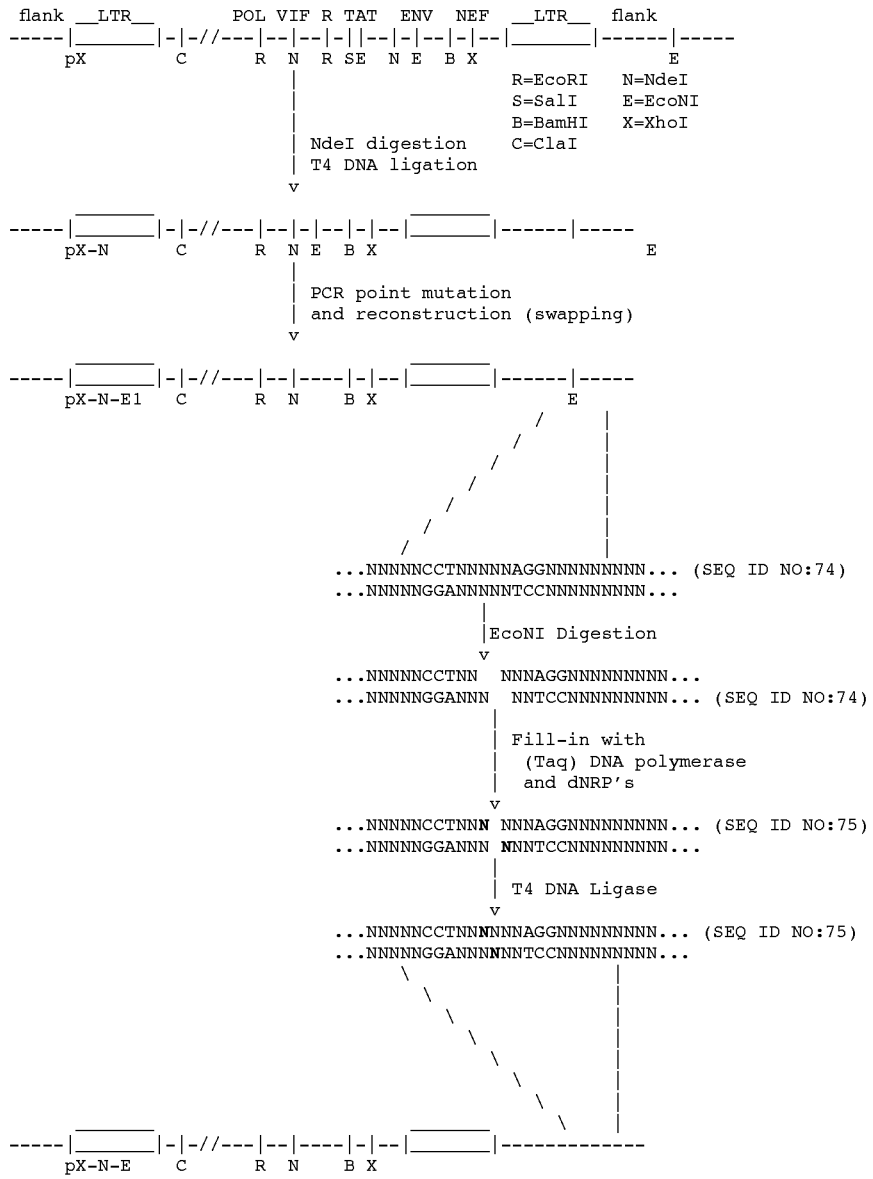

EcoNI cuts the sequence CCT(N)5AGG. When there are six (6) bases in between CTT and AGG, i.e., CCT(N)6AGG, EcoNI will not cut any more.

Reinstallation of the NDEI Fragment

Because of the limited availability of convenient restriction sites, the re-installation of the NdeI fragment took two-steps: first to reconstruct full-length plasmid (pX-E2), then to mutate the EcoNI site at nt 7631 again.

(10) pX-N-E and parental pX (both prepared from transformed DM1 cells) were digested simultaneously with ClaI (nt 829) and BamHI (nt 8474). The digest mixture was self-ligated and used to transform competent HB101 *E. Coli* cells.

(11) Miniplasmids were screened by BglII and HindIII digestion. Those with the same digestion patterns as pX would be the full-length clones.

(12) The full-length clones were further checked by digesting with EcoNI, and the clone cut twice and yielding a band of 1665 bps was chosen and named as pXE-2. pXE-2 is the same wild type clone as pX but with the outside EcoNI site removed.

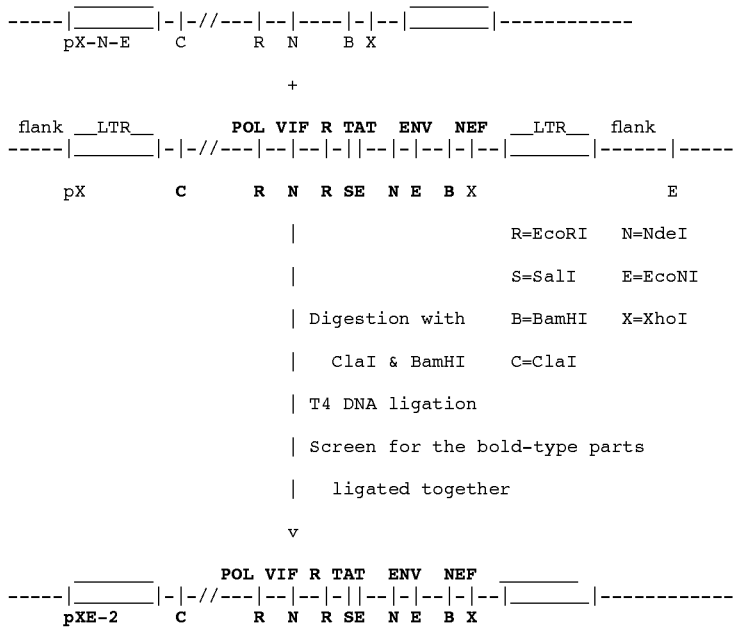

(13) Another bridging PCR, in order to mutate the EcoNI site at nt 7631 which had been reinstated into pXE-2.

| | | |
|---|---|---|
| pX, 1 ug/ml | | 1 µl |
| Reaction buffer, 10x | | 5 µl |
| Tris-HCl, pH 8.3 | 500 mM | |
| KCl | 500 mM | |
| MgCl2 | 20 mM | |
| Gelatine | 0.05% | |
| dNTP, 2.5 mM each | | 3 µl |
| 5'primer, 5738-5761 60 ug/ml | | 2 µl |
| 3'primer, 8670-8642 60 ug/ml | | 2 µl |
| "B"primer, 7617-7652 6 ug/ml | | 2 µl |
| AmpliTaq DNA polymerase, 5 u/µl (from Perkin Elmer Cetus) | | 0.2 µl |
| Double distilled water | | 34.8 µl |
| | | 50.0 µl |

Here only the 5' primer is new, the other two are SEQ ID NO:14 & 15.

```
5'primer: HTX 5738

ATAAGAATTCTGCAACAACTGCTG
        |----- 5738-5761 ----->|

SEQ ID NO:16

ATAAGAATTC TGCAACAACT GCTG            24
```

The samples were run on a DNA Thermal Cycler (Perkin Elmer Cetus) for 50 cycles each consisting of 94° C. for 20 seconds, 60° C. for 20 seconds and 74° C. for three minutes. 10 µl of the PCR product was run on agarose gel (NuSieve 3:1, FMC). The correct size of the PCR product should be 2932 base pairs, which was confirmed.

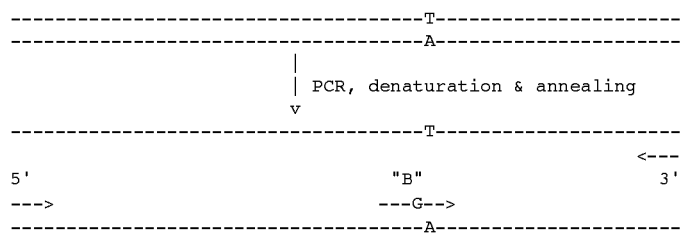

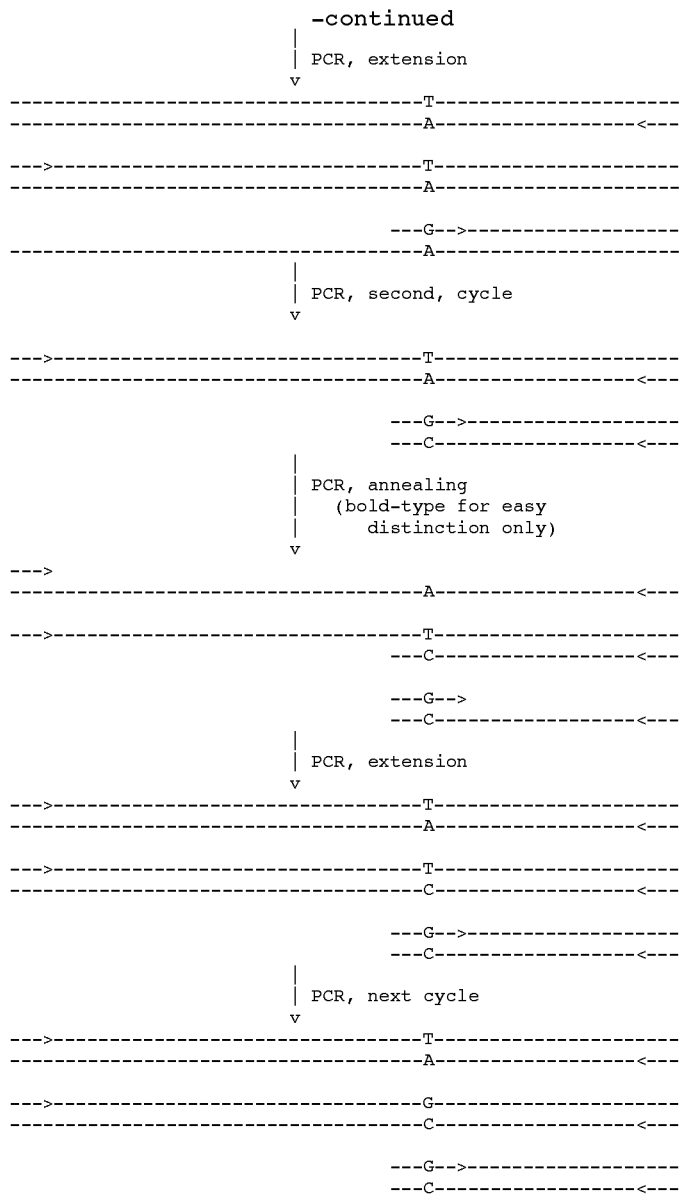

It becomes clear that, even with an intact template, the bridging primer would be able to insert its sequence into some of the amplified fragments. To confirm the successful implantation of the "T→G" (i.e., CCTNNNNNAGG→CCGNNNNNAGG) point mutation at nt 7633, the PCR products were digested with EcoNI. Control with only 5' and 3' primers the whole fragment was 2932 bps. The product was cut into three bands of 232, 1665 and 1035 bps respectively.

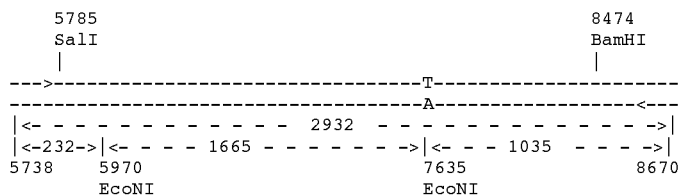

For the PCR with three primers, the undigested product was a mixture containing two bands of 2932 and 1053 respectively. When cut with EcoNI, four bands appeared. Besides the 1665, 1053+1035, and 232 bp bands, another band appeared at 2.7 kb, due to considerable amount of the product carrying the point mutation at nt 7633 resulting in the elimination of EcoNI site at nt 7631.

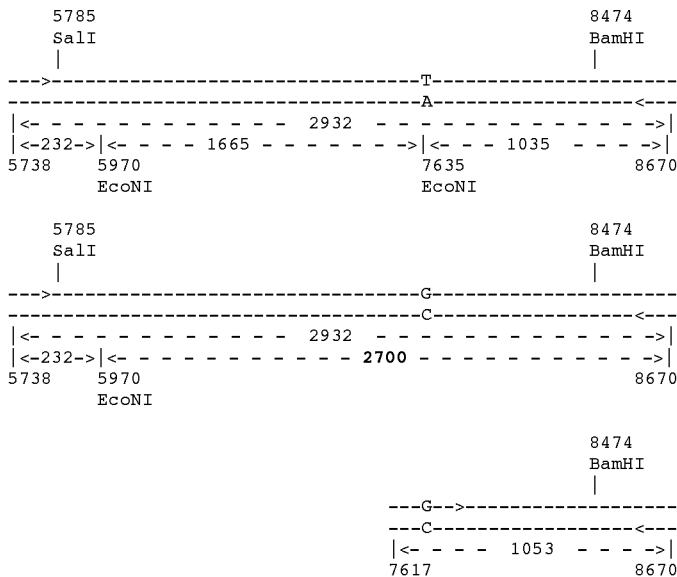

The PCR product with 2.7 kb band was digested along with pXE-2 plasmid by restriction enzymes SalI and BamHI. The digest was selfligated. The ligation was used to transform competent HB101 cells. Miniplasmids were screened with HindIII then with EcoNI. The clone with nt 7631 EcoNI site mutated, pXE, showed the same HindIII digestion pattern as that of pX or pXE-2, but was cut only once by EcoNI compared to twice for pXE-2 and three times for pX.

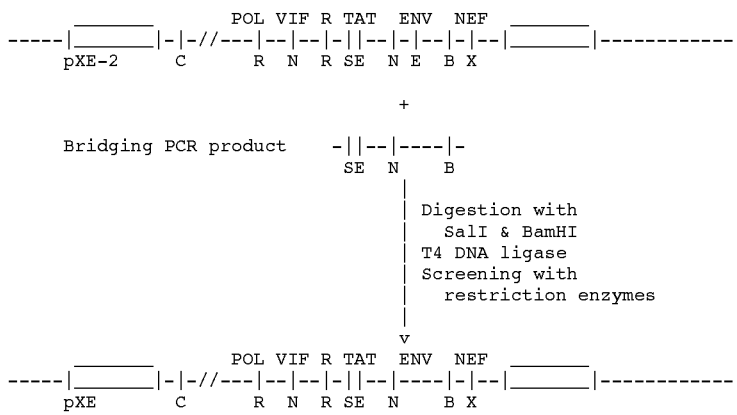

pXE was used later for constructing antisense molecular clones. pXE can also be used as wild type control just as pX.

(**) The abolishment of the two extra EcoNI restriction sites can be done in an alternative way. The starting pX plasmid prepared from DM1 competent cells can be digested simultaneously or consecutively with both BclI (nt 2428) and BamHI (nt 8474) then self-ligated.

(Note: BclI and BamHI produce compatible cohesive ends that can be ligated to each other. But the ligation product cannot be recut by either enzyme. Compatible cohesive ends unable to be recut after ligation also occur between SalI and XhoI, see gene-expression vector construction below. BclI recognizes TGATCA and cuts between "T" and "G", but this sequence will not be cut by BclI when the middle "A" is methylated by Dam methylase. DM-1 *E. coli* cells are Dam methylase negative. DNA prepared from DM-1 cells are not methylated and therefore can be cut by BclI.)

The plasmid clone with BclI-BamHI fragment deleted ("pX-BB") has both proviral EcoNI sites removed. pX-BB can be cut with EcoNI, treated with TaqI polymerase, self-ligated and used to transform DM1 competent cells. This results in the abolishment of the outside EcoNI site. This clone ("pX-BB-Eo") together with pX can be cleaved simultaneously with ClaI (nt 829, ClaI is also Dam methylation sensitive and demands DM-1 cell prepared DNA for effective cleavage) and XhoI (nt 8896), selfligated, and used to transform competent cells. The full-length clone with only two proviral EcoNI sites (pX-E2) can be used for sequence swapping with "bridging PCR" product between SalI and BamHI as described in Step (13). The final clone with only one EcoNI site at nt 5966 is pXE.

Construction of Full-Length Antisense/Ribozyme Molecular Clones

(14) PCR reactions were performed using pX or other appropriate plasmids as templates and Tvpr/Trev or/and other primers as depicted previously. The PCR product was checked by running 10 μl on agarose gel. The fragments were shown to be of expected sizes and/or of expected restriction digestion patterns.

(15) Each of the PCR products together with plasmid pXE were digested with SalI and EcoNI, simultaneously.

Restriction Digestion Patterns of Molecular HIV-1 (HXB2) Full-Length Clones and Major Subclones If the exact size of a particular fragment (band) is known, it is indicated by exact number in bp (base pairs); if the exact size is not known, the estimated size is indicated by kb (kilobase). Bold-type indicates major clones or bands of interest for the particular restriction enzyme digestion.

| X = pX | E = pXE | Ea = pXE-a | Eb = pXE-b |
|---|---|---|---|
| Ear = pXE-ar | Ebr = pXE-br | N = pX-N | NE = pX-N-E |
| E2 = pX-E2 | E = pXE | XCS = pX-CS | |

SalI + EcoNI

| | X | E | Ea | Eb | Ear | Ebr | N | NE | E2 | E | XCS |
|---|---|---|---|---|---|---|---|---|---|---|---|
| 17.0kb | — | | | | | | | — | | | |
| 15.7kb | | | | | | | | | | — | |
| 15.3kb | | | | | | | | | | | — |
| 12.0kb | | | | | | | — | | | | |
| 11.5kb | — | | | | | | | | | | |
| 7.0kb | | | | | | | | | | | — |
| 3.8kb | | | | | | | — | | | | |
| 1665bp | — | | | | | | | | | | |
| 206bp | | | | | | | — | — | | | |
| 185bp | — | — | — | — | | | | | — | — | — |

Note: Though done in one tube, the construction of antisense/ribozyme proviral clones is actually done stepwise involving the simultaneous digestion of pXE with SalI and EcoNI, and the replacement of the SalI-EcoNI fragment (185 bps) by PCR-inverted antisense/ribozyme fragments (185 bps for pXE-a and pXE-b; 206 bps with one ribozyme incorporated, 227 with two, and 248 with three).

(16) The digestion mixture was self-ligated and used to transform competent HB101 *E. Coli* cells. Colonies were picked.

(17) Miniplasmids were screened for antisense/ribozyme clones by cutting with Bsu36I, choosing clones whose original 1360 bp band had been changed to 1514 bp or bigger. Digestions with other restriction enzymes have also been used to confirm the correctness of constructions. See previous digestion patterns.

Restriction Digestion Patterns of Molecular HIV-1 (HXB2) Full-Length Clones and Major Subclones If the exact size of a particular fragment (band) is known, it is indicated by the exact number in bp (base pairs); If the exact size is not known, the estimated size is indicated by kb (kilobase). Bold-type indicates major clones or bands of interest for the particular restriction enzyme digestion.

| X = pX | E = pXE | Ea = pXE-a | Eb = pXE-b |
|---|---|---|---|
| Ear = pXE-ar | Ebr = pXE-br | N = pX-N | NE = pX-N-E |
| E2 = pX-E2 | E = pXE | XCS = pX-CS | |

Bsu36I (SauI)

| | X | E | Ea | Eb | Ear | Ebr | N | NE | E2 | E | XCS |
|---|---|---|---|---|---|---|---|---|---|---|---|
| 13.0kb | — | — | | | — | — | | — | — | — | |
| 8.5kb | | | | | | | | | | | — |
| 1695bp | — | — | — | | | — | — | — | — | — | |
| 1514bp | | | — | | —* | —* | | | | | |
| 1360bp | — | — | | | | | | | — | — | — |
| 0.7kb | — | — | — | | — | — | — | — | — | — | |

*This band is 1535 bps with one ribozyme incorporated. It will be 1556 with two, and 1577 with three.

(18) The antisense/ribozyme molecular constructions are confirmed by dideoxy sequencing of the inverted areas using primer HIV-1 5738–5761, i.e., SEQ ID NO:16.

5'-ATAAGAATTCTGCAACAACTGCTG-3'/Eco-RI

EXAMPLE 5

Construction of TAT-Expression Vectors Using HIV-1 Molecular Clones

Recombinant PCR is employed to construct tat-expression clone with major HIV-1 genes truncated. The advantage of PCR recombination is that it is easy to construct the molecular clone(s) with precision. The steps used are as follows:

(1) The tat-expression clone, as mentioned above, has the gag, pol reading frames truncated but has vpr, tat, rev and env intact. Examining pX, the sequences at the beginning of the gag open reading frame and the sequences starting from position 5320 (in the mid-frame of vif, before splice junction site 5388/5389) are as follow:

```
              789                            825       835      942
               |                              |    Cla -I|        |
HXB2    ..ATGGGTGCGAGAGCGTCAGTATTATGCGGGGAGAATTAGATCGATGGGAAAAA..     (SEQ ID NO:60)
(GAG)     M  G  A  R  A  S  V  L  S  G  G  E  L  D  R  W  E  K..
NL43    ..ATGGGTGCGAGAGCGTCGGTATTATGCGGGGGAGAATTAGATaaATGGGAAAAA..     (SEQ ID NO:62)
```

```
                                                   -continued
                                       K
      (790)                                     (943)

5320              5340
               |                 |
HXB2    ..AGATATAGCACACAAGTAGACCCTGAACTAGCAGACCAACTAATTCATCTGTAT..        (SEQ ID NO:61)
(VIF)    ..R  Y  S  T  Q  V  D  P  E  L  A  D  Q  L  I  H  L  Y..
NL43    ..AGATATAGCACACAAGTAGACCCTGAcCTAGCAGACCAACTAATTCATCTGTAT..        (SEQ ID NO:63)
               |                |D
            (5321)           (5341)
```

(2) The sequences written in bold letters were arranged into one oligonucleotide primer. Remember that all numbering are of HXB2 clone, even though sometimes NL4-3 sequences are actually employed. In such cases, the corresponding sequences are given in parentheses.

```
                      825    835   5320(5321)         5340(5341)
                       |      Cla-I \/                    |
       HTX 835-5320   TTAGATCGATGATAGCACACAAGTAGACCCTG         SEQ ID NO:17

TTAGATCGAT GATAGCACAC AAGTAGACCC TG                             32
```

(3) Primer HTX 835-5320 was used to couple with another primer, Rvpr 5794–5767, in the PCR reaction with pNL as the template.

```
Rvpr 5794-5767 CTATGTCGACACCCAATTCTG
      AAATGG                             SEQ ID NO:18

CTATGTCGAC ACCCAATTCT GAAATGG 27
```

This is a negative-strand primer specially designed to restore the "perfect" vpr reading frame by deleting a "T" at 5770 of HXB2. Compare this primer with the original sequences in HXB2 and NL4-3:

```
HXB2 SEQ    5767  CCATTTTCAGAATTGGGTGTCGACATAG 5794  (positive)  (SEQ ID NO:64)
                  GGTAAAAGTCTTAACCCACAGCTGTATC        (negative)

Rvpr SEQ    5767  GGT-AAAGTCTTAACCCACAGCTGTATC 5794  (negative)  (SEQ ID NO:76)

NL43 SEQ    5768  CCATTTCAGAATTGGGTGTCGACATAG 5794   (positive)  (SEQ ID NO:65)
                  GGTAAAGTCTTAACCCACAGCTGTATC        (negative)
```

It becomes clear that primer Rvpr is actually made of sequences of pNL which preserve intact and functional vpr gene. As discussed previously, the vpr gene has been truncated and is functionless with HXB2, the plasmid clone of which, pX, has been used as parental structure for all the antisense/ribozyme proviral clones. Restoration of vpr function in the gene expression vector benefits the antisense/ribozyme viruses' ability to replicate by providing the antisense/ribozyme virus producer cell lines with the "weak transcriptional activator" (see FIG. 2). That is, the use of pNL sequence is to restore vpr function with the gene-expression vector. The inclusion of the ClaI restriction site is to facilitate the subsequent cloning of the gene-expression vector.

| | |
|---|---|
| pNL, 1 ug/ml | 1 µl |
| Reaction buffer, 10x | 5 µl |
| Tris-HCl, pH 8.3 | 500 mM |
| KCl | 500 mM |
| MgCl2 | 20 mM |
| Gelatine | 0.05% |
| dNTPs, 2.5 mM each | 3 µl |
| HTX 835-5320, 60 ug/ml | 2 µl |
| Rvpr 5794-5767, 60 ug/ml | 2 µl |
| AmpliTaq DNA polymerase, 5 u/µl | 0.2 µl |
| Double distilled water | 36.8 µl |
| | 50.0 µl |

Fifty cycles of thermal cycling were done, each consisting of 94° C. for 20 seconds, 50° C. for 20 seconds and 74° C. for 2 minutes.

The PCR product was 485 bps total. The main part of it was a 474-bp fragment from nt 5320 (pNL nt 5321) to nt 5794 (same for both clones). This 474-bp fragment is of NL4-3 origin, which is 1 bp shorter than and 26 bps different from the corresponding fragment of HXB2. The PCR product further included at its 5' end 11 bps of HXB2 origin (nt 825–835) where the unique Cla-I site is located. The following shows the actual sequences of the PCR product.

(4) The PCR product together with full-length pX (prepared from dam methylase negative DM-1 competent cells from GIBCO BRL) were cleaved with Cla-I and Sal-I simultaneously. The digest was religated with T4 DNA ligase and the ligation was used to transformed HB101 as well as DM-1 cells. Miniplasmids were screened with restriction enzyme digestion, looking for the clone where the natural ClaI-SalI fragment (4955 bps) had been replaced by the PCR ClaI-SalI fragment (470 bps). 4484 bps had been

```
                                                              SEQ ID NO:19
TTA GAT CGA TGATAGCACA CAAGTAGACC CTGACCTAGC AGACCAAGTA        49
Leu Asp Arg

ATTCATCTGC ACTATTTTGA TTGTTTTTCA GAATCTGCTA TAAGAAATAC         99

CATATTAGGA CGTATAGTTA GTCCTAGGTG TGAATATCAA GCAGGACATA        149

ACAAGGTAGG ATCTCTACAG TACTTGGCAC TAGCAGCATT AATAAAACCA        199

AAACAGATAA AGCCACCTTT GCCTAGTGTT AGGAAACTGA CAGAGGACAG        249

ATG GAA CAA GCC CCA GAA GAC CAA GGG CCA CAG AGG GAG CCA TAC   294
Met Glu Gln Ala Pro Glu Asp Gln Gly Pro Gln Arg Glu Pro Tyr
              5                  10                  15

AAT GAA TGG ACA CTA GAG CTT TTA GAG GAA CTT AAG AGT GAA GCT   339
Asn Glu Trp Thr Leu Glu Leu Leu Glu Glu Leu Lys Ser Glu Ala
             20                  25                  30

GTT AGA CAT TTT CCT AGG ATA TGG CTC CAT AAC TTA GGA CAA CAT   384
Val Arg His Phe Pro Arg Ile Trp Leu His Asn Leu Gly Gln His
             35                  40                  45

ATC TAT GAA ACT TAC GGG GAT ACT TGG GCA GGA GTG GAA GCC ATA   429
Ile Tyr Glu Thr Tyr Gly Asp Thr Trp Ala Gly Val Glu Ala Ile
             50                  55                  60

ATA AGA ATT CTG CAA CAA CTG CTG TTT ATC CAT TTC AGA ATT GGG   474
Ile Arg Ile Leu Gln Gln Leu Leu Phe Ile His Phe Arg Ile Gly
             65                  70                  75

TGT CGA CAT AG                                                485
Cys Arg His Ser
             79
```

The first coding region at the beginning of the fragment where only 3 amino acid residues are shown is the carboxyl terminus of the truncated GAG protein. The second coding region starting at nt 250 is VPR which continues beyond this fragment as shown in SEQ ID NO:20.

deleted. The miniplasmids were cut with BglII. The right deletion clone yielded a 2083 bp fragment while the two wild type fragments of 1622 bp (nt 473–2095) and 4945 bp (nt 2095–7040) disappeared. Mathematically, 6567 bp (nt 473–7040) minus 4484 bp (nt 836–5319) equals 2083 bp.

PCR made fragment (SEQ ID NO:19, with the portion truncated)

was used to replace the ClaI-SalI fragment of the wild type pX,

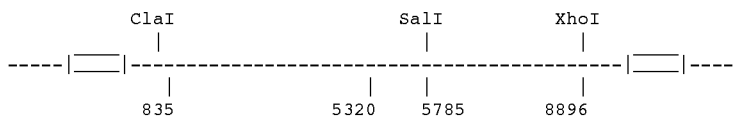

and yielded the recombinant truncation clone pX-CS.

ClaI                    SalI                    XhoI

```
                      -continued
      |    |    |                        |    |
------|    |----|xxxxxxxxxxxxxxxx|-------------------|    |----
      |    |    |   (deleted)    |       |           |    |
      835        5320           5785    8896
```

Restriction Digestion Patterns of Molecular HIV-1 (HXB2)
Full-Length Clones and Major Subclones.

If the exact size of a particular fragment (band) is known, it will be indicated by exact number in bp (base pairs); If the exact size is not known, the estimated size will be indicated by kb (kilobase). Bold-type indicates major clones or bands of interest for the particular restriction enzyme digestion.

constructed). Compare "X" and "XCS" where 4955 base pair band in "X" is reduced to 470 base pair band in "XCS".

The recombinant sequences from the beginning of gag to the end of vpr are as follows.

```
                                                              SEQ ID NO:20
ATG GGT GCG AGA GCG TCA GTA TTA TGC GGG GGA GAA TTA GAT CGA   45
Met Gly Ala Arg Ala Ser Val Leu Ser Gly Gly Glu Leu Asp Arg
                5               10              15

TGATAGCACA CAAGTAGACC CTGACCTAGC AGACCAACTA ATTCATCTGC        95

ACTATTTTGA TTGTTTTTCA GAATCTGCTA TAAGAAATAC CATATTAGGA       145

CGTATAGTTA GTCCTAGGTG TGAATATCAA GCAGGACATA ACAAGGTAGG       195

ATCTCTACAG TACTTGGCAC TAGCAGCATT AATAAAACCA AAACAGATAA       245

AGCCACCTTT GCCTAGTGTT AGGAAACTGA CAGAGGACAG ATG GAA CAA GCC  297
                                             Met Glu Gln Ala

CCA GGA GAC CAA GGG CCA CAG AGG GAG CCA TAC AAT GAA TGG AGA  342
Pro Glu Asp Gln Gly Pro Gln Arg Glu Pro Tyr Asn Glu Trp Thr
5               10              15

CTA GAG CTT TTA GAG GAA CTT AAG AGT GAA GCT GTT AGA CAT TTT  387
Leu Glu Leu Leu Glu Glu Leu Lys Ser Glu Ala Val Arg His Phe
20              25              30

CCT AGG ATA TGG CTC CAT AAC TTA GGA CAA CAT ATC TAT GAA ACT  432
Pro Arg Ile Trp Leu His Asn Leu Gly Gln His Ile Tyr Glu Thr
35              40              45

TAC GGG GAT ACT TGG GCA GGA GTG GAA GCC ATA ATA AGA ATT GTG  477
Tyr Gly Asp Thr Trp Ala Gly Val Glu Ala Ile Ile Arg Ile Leu
50              55              60

CAA CAA CTG CTG TTT ATC CAT TTC AGA ATT GGG TGT CGA CAT AGC  522
Gln Gln Leu Leu Phe Ile His Phe Arg Ile Gly Cys Arg His Ser
65              70              75

AGA ATA GGC GTT ACT CGA CAG AGG AGA GCA AGA AAT GGA GCC AGT  567
Arg Ile Gly Val Thr Arg Gln Arg Arg Ala Arg Asn Gly Ala Ser
80              85              90

AGA TCC TAG                                                  576
Arg Ser
95
```

| X = pX | E = pXE | Ea = pXE-a | Eb = pXE-b |
|---|---|---|---|
| Ear = pXE-ar | Ebr = pXE-br | N = pX-N | NE = pX-N-E |
| E2 = pX-E2 | E = pXE | XCS = pX-CS | |
| ClaI + SalI | | | |

|  | X | E | Ea | Eb | Ear | Ebr | N | NE | E2 | E | XCS |
|---|---|---|---|---|---|---|---|---|---|---|---|
| 15.7kb | | | | | | | | | | — | — |
| 12.0kb | — | — | — | | | — | | | | — | — |
| 4955 | — | — | — | — | — | — | | | | — | |
| 470 | | | | | | | | | | | — |

Note: This enzyme combination was used to construct pX-CS (from which pX-CSneo and pxneo were In this recombinant truncation clone, "pX-CS", the gag gene is truncated to 15 amino acids only; a "perfect" vpr gene has been reinstated (by replacing HXB2 vpr gene with NL4-3 vpr gene); while most of the gag gene, all of pol gene, and the 5' portion of the vif gene have been deleted. Preserved are the major 5' splice donor site 742/743, splice junction sites 5388/5389, 5462/5463, 5776/5777, 5975/5976, 6044/6045, and 8377/8378. Tat, rev, vpr and env genes are intact. The nef open reading frame (orf) is also intact, but it is interrupted by the insertion of a neo(r) cassette into the unique XhoI site at nt 8896.

(5) The neomycin resistance cartridge from pMClneoPolyA (Stratagene) is inserted into the XhoI site (8896) of pX-CS. The cartridge is 1146 bp long between XhoI (nt 451 of pMClneoPolyA) and SalI (nt 1597 of pMClneoPolyA), containing the neo(r) gene from Tn5, the Herpes Simplex thymidine kinase promoter and the enhancer sequence from polyoma virus Py F441. pX-CS was digested with XhoI, and pMClneoPolyA was digested with XhoI and SalI. After killing the restriction enzymes' activities by heating the digests at 65° C. for 15 minutes, the two digests were mixed together for ligation. SalI and XhoI produce compatible restriction ends capable of ligating to each other, the ligation product of which, however, cannot be cut by either enzyme.

(6) The ligation is then used to transform competent *E. Coli* HB101 cells. Single colonies were picked into LBamp medium.

(7) Recombinant miniplasmids are digested with BglII and XhoI simultaneously.

Clones without insertion have, among others, two bands of 1276 bp (BglII 7620-XhoI 8896) and 154 bp (XhoI 8896-BglII 9050). Note the GenBank BglII site 8085 is missing from pX.

Clones with insertions have either a 1276 bp band and a 1300 bp band (154+1146=1300, right orientation), or, a 2422 bp band (1276+1146=1957, wrong orientation) and a 154 bp band.

The binding together of the neomycin resistance gene and the tat gene assures the entry of both genes into the cells at the same time, transforming the cells into neomycin resistance and tat expression simultaneously. By including antibiotic G418 in the cell culture medium, every surviving cell produces TAT protein, capable of supporting the production of the antisense/ribozyme viruses.

(9) As control, a tat(−) but neomycin(r)(+) clone is constructed from pX-CSneo. pX-CSneo is simultaneously digested with SalI (cut HIV1 nt 5785 only) and XhoI (cuts the ligation junction HIV1 nt 8896-XhoI and pMCneoPolyA nt 452-XhoI, but does not cut the ligation junction between pMCneoPolyA nt 1597-SalI and HIV1 nt 8897-XhoI, the latter junction is not be cut by SalI either). Religation of the fragments is used to transform competent *E. Coli* HB101. Miniplasmids are screened for the clone with SalI (5785) to XhoI (8896) fragment (3111 bp) deleted. This clone basically carries two HIV-1 LTRs with the neo(r) gene in between. It is named pX-neo.

The TAT-expression control clone pX-neo

```
No insertion:

1276              154
...---|--------------------|-----|---...
    BglII             XhoI/XhoI BglII
        |<----- 1276 ------>|<154>|

Insertion in right orientation:

1276           1146(insert)     154
...---|--------------------|=================>|-----|---...
    BglII             XhoI/XhoI          SalI/XhoI BglII
        |<----- 1276------->|<-------- 1300---------->|

Insertion in wrong orientation:

1276           1146(insert)     154
...---|--------------------|<=================|-----|---...
    BglII             XhoI/SalI           XhoI/XhoI BglII
        |<---------------- 2422 ---------------->|<154>|
```

XhoI/XhoI=XhoI end ligated to XhoI end. The ligation product can be recut by XhoI.

SalI/XhoI=SalI end ligated to XhoI end. The ligation product cannot be cut by either SalI or XhoI.

The clone with 1300 bp band is chosen as HIV-1-tat-expression vector (pX-CSneo). The nef open reading frame has been interrupted by the insertion of a neo(r) cassette.

The TAT-expression clone pX-CSneo

```
        ClaI                    SalI         XhoI
         |                       |            |
-----|_____|---|xxxxxxxxxxxxxxxx|------------|_____|----
     |          |   (deleted)    |            |
                835             5320        5785  8896
                                                  /\
                                                 /  \
                                                / Neo(r) \
                                          XhoI ---------- SalI
                                          (451)  insert |(1597)
                                                        |
                                                      BamHI
                                                      (1591)
```

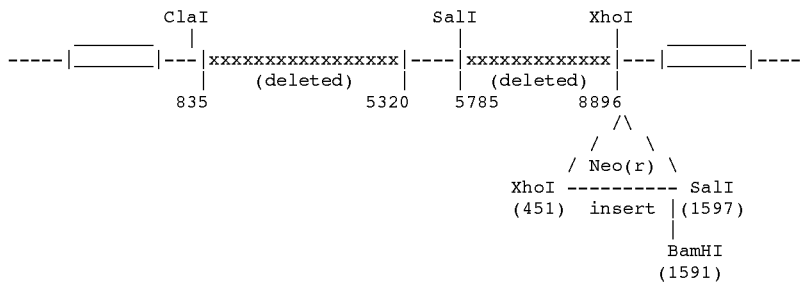

EXAMPLE 6

Construction of TAT-Expression Clone Using Non-HIV1 Vector

The aforementioned truncation tat-expression vectors employ identical promoter/enhancer systems with HIV-1 antisense/ribozyme proviral clones. Tat-expression vectors using other promotors were also constructed. This is done by inserting the tat coding sequence into one of many gene expression vectors such as SFneo. SFneo contains spleen focus forming virus (SFFV) LTR as the promotor to drive the inserted gene to express protein. SFneo also contains a neomycin resistance gene expression cassette [Neo(r)], enabling the transformed cells to grow in the presence of antibiotic G418. Since the tat and rev coding regions overlap with each other, it was decided that both coding frames be kept intact. It was also decided that the two exons of the coding frame be linked together before being inserted into the expression vector. The two halves of the coding regions are as follows:

The first exon:

```
            Eco -I          .          .          . \/sa     .Sal -I    .
      ATAATAAGAATTCTGCAACAACTGCTGTTTATCCATTTTCAGAATTGGGTGTCGACATAG  5794   (SEQ ID NO:66)

.          .          .          .          .          .
      CAGAATAGGCGTTACTCGACAGAGGAGAGCAAGAAATGGAGCCAGTAGATCCTAGACTAG  5854
                                          (TAT) M   E   P   V   D   P   R   L

.          .          .          .          .          .
      AGCCCTGGAAGCATCCAGGAAGTCAGCCTAAAACTGCTTGTACCAATTGCTATTGTAAAA  5914
       E   P   W   K   H   P   G   S   Q   P   K   T   A   C   T   N   C   Y   C   K

.          .          .          .          .          .
      AGTGTTGCTTTCATTGCCAAGTTTGTTTCATAACAAAAGCCTTAGGCATCTCCTATGGCA  5974
       K   C   C   F   H   C   Q   V   C   F   I   T   K   A   L   G   I   S   Y   G
                                                                          (REV) M   A

\/sa       .          .     Sac -I          .          . HindIII .
      GGAAGAAGCGGAGACAGCGACGAAGAGCTCATCAGAACAGTCAGACTCATCAAGCTTCTC  6034
       R   K   K   R   R   Q   R   R   R   A   H   Q   N   S   Q   T   H   Q   A   S
         G   R   S   G   D   S   D   E   E   L   I   R   T   V   R   L   I   K   L   L \sd
      TATCAAAGCA                                                      6044
       L   S   K   Q
         Y   Q   S
```

The second exon:

```
            \/sa       .          .          .          .          .
                  ACCCACCTCCCAACCCCGAGGGGACCCGACAGGCCCGAAGGAATAGAAGA  8427   (SEQ ID NO:67)
             (TAT) P   T   S   Q   P   R   G   D   P   T   G   P   K   E
             (REV) N   P   P   P   N   P   E   G   T   R   Q   A   R   R   N   R   R

.          .          .          .     Bam-HI     .
      AGAAGGTGGAGAGAGAGACAGAGACAGATCCATTCGATTAGTGAACGGATCCTTGGCACT  8487

R   R   W   R   E   R   Q   R   Q   I   H   S   I   S   E   R   I   L   G   T
            .          .          .          .          .          .
      TATCTGGGACGATCTGCGGAGCCTGTGCCTCTTCAGCTACCACCGCTTGAGAGACTTACT  8457

Y   L   G   R   S   A   E   P   V   P   L   Q   L   P   P   L   E   R   L   T
            .          .          .          .          .          .
      CTTGATTGTAACGAGGATTGTGGAACTTCTGGGACGCAGGGGGTGGGAAGCCCTCAAATA  8607
```

-continued

```
L   D   C   N   E   D   C   G   T   S   G   T   Q   G   V   G   S   P   Q   I
TTGGTGGAATCTCCTACAGTATTGGAGTCAGGAACTAAAGAATAGTGCTGTTAGCTTGCT  8667

L   V   E   S   P   T   V   L   E   S   G   T   K   E
CAATGCCACAGCC
```

Note: The numbers given on right side of the sequences are the original position for the last base of that line. TAT and REV proteins are lined up with their coding nucleotide sequences. Also given are splice donor (sd) and splice accepter (sa) sites, as well as some important restriction sites.

For easy demonstration of the procedures by which the two parts of the genes are linked together, the protein sequences are removed and the complementary DNA sequences are added.

The first exon:

PCR was employed to accomplish the linkage. The PCR protocol used is "bridging PCR". The protocol was designed to link together at precise positions two segments of originally separated DNA and to amplify the linked sequences with the same PCR reaction in the same tube. A critical feature of "bridging PCR" is to include three (or more) primers in the PCR reaction: two ordinary primers to anneal to either end of the linked fragment, and one (or more) "bridging primer" to span the intended areas of linking. A "bridging primer" can be either orientation, but amplification may be more efficient if it points to the shorter half of the linked fragment.

For linking together the two exons of tat and rev genes, the three primers are designed as follows.

```
        Eco -I          .       .       . \/sa     .Sal -I  .
ATAATAAGAATTCTGCAACAACTGCTGTTTATCCATTTTCAGAATTGGGTGTCGACATAG 5794  (SEQ ID NO:66)
TATTATTCTTAAGACGTTGTTGACGTCAAATAGGTAAAAGTCTTAACCCACAGCTGTATC

CAGAATAGGCGTTACTCGACAGAGGAGAGCAAGAAATGGAGCCAGTAGATCCTAGACTAG 5854
GTCTTATCCGCAATGAGCTGTCTCCTCTCGTTCTTTACCTCGGTCATCTAGGATCTGATC

AGCCCTGGAAGCATCCAGGAAGTCAGCCTAAAACTGCTTGTACCAATTGCTATTGTAAAA 5914
TCGGGACCTTCGTAGGTCCTTCAGTCGGATTTTGACGAACATGGTTAACGATAACATTTT

AGTGTTCGTTTCATTGCCAAGTTTGTTTCATAACAAAAGCCTTAGGCATCTCCTATGGCA 5974
TCACAACGAAAGTAACGGTTCAAACAAAGTATTGTTTTCGGAATCCGTAGAGGATACCGT
\/sa        .           .     Sac -I     .        . HindIII .
GGAAGAAGCGGAGACAGCGACGAAGAGCTCATCAGAACAGTCAGACTCATCAAGCTTCTC 6034
CCTTCTTCGCCTCTGTCGCTGCTTCTCGAGTAGTCTTGTCAGTCTGAGTAGTTCGAAGAG
        \/sd
TATCAAAGCA                                                    6044
ATAGTTTCGT
```

The second exon:

```
    \/sa        .           .       .       .       . 8427  (SEQ ID NO:67)
         ACCCACCTCCCAACCCCGAGGGGACCCGACAGGCCCGAAGGAATAGAAGA
         TGGGTGGAGGGTTGGGGCTCCCCTGGGCTGTCCGGGCTTCCTTATCTTCT

.           .           .           .   Bam-HI  .
AGAAGGTGGAGAGAGAGACAGAGACAGATCCATTCGATTAGTGAACGGATCCTTGGCAGT 8487
TCTTCCACCTCTCTCTCTGTCGCTGTCTAGGTAAGCTAATCACTTGCCTAGGAACCGTGA

TATCTGGGACGATCTGCGGAGCCTGTGCCTCTTCAGCTACCACCGCTTGAGAGACTTACT 8547
ATAGACCCTGCTAGACGCCTCGGACACGGAGAAGTCGATGGTGGCGAACTCTCTGAATGA

CTTGATTGTAACGAGGATTGTGGAACTTCTGGGACGCAGGGGGTGGGAAGCCCTCAAATA 8607
GAACTAACATTGCTCCTAACACCTTGAAGACCCTGCGTCCCCCACCCTTCGGGAGTTTAT

TTGGTGGAATCTCCTACAGTATTGGAGTCAGGAACTAAAGAATAGTGCTGTTAGCTTGCT 8667
AACCACCTTAGAGGATGTCATAACCTCAGTAATTGATTTCTTATCACGACAATCGAACGA

CAATGCCACAGCC
GTTACGGTGTCGG
```

5'-end primer: HTX 5738, i.e., SEQ ID NO:16

```
        Eco RI
ATAAGAATTCTGCAACAACTGCTG
|------5738-5761------>|
```

"Bridging primer": HTX 6044-8378

```
 Hind-III
CAAGCTTCTCTATCAAAGCAACCCACCTCCCAACCCCGAG
|----6025-6044----->----8378-8397----->|
```

-continued
CAAGCTTCTC TATCAAAGCA ACCCACCTCC CAACCCCGAG  40

3'-end primer: HTX 8670, i.e., SEQ ID NO:14.
the 3 bases underlined has been changed to
accommodate an EcoRI site.

```
       Eco-RI
TTGAGAATTCTAACAGCACTATTGTTTAG
|---------8670-8642-------- |
```

SEQ ID NO:21

The primers, in bold-type letters, anneal to the sequences at positions:

```
           Eco RI   HTX 5738
              ATAAGAATTCTGCAACAACTGCTG .         . \/sa    .Sal -I  .  (SEQ ID NO:16)
         ATAATAAGAATTCTGCAACAACTGCTGTTTATCCATTTTCAGAATTGGGTGTCGACATAG 5794
         TATTATTCTTAAGACGTTGTTGACGTCAAATAGGTAAAAGTCTTAACCCACAGCTGTATC

CAGAATAGGCGTTACTCGACAGAGGAGAGCAAGAAATGGAGCCAGTAGATCCTAGACTAG 5854
         GTCTTATCCGCAATGAGCTGTCTCCTCTCGTTCTTTACCTCGGTCATCTAGGATCTGATC

AGCCCTGGAAGCATCCAGGAAGTCAGCCTAAAACTGCTTGTACCAATTGCTATTGTAAAA 5914
         TCGGGACCTTCGTAGGTCCTTCAGTCGGATTTTGACGAACATGGTTAACGATAACATTTT

AGTGTTGCTTTCATTGCCAAGTTTGTTTCATAACAAAAGCCTTAGGCATCTCCTATGGCA 5974
         TCACAACGAAAGTAACGGTTCAAACAAAGTATTGTTTTCGGAATCCGTAGAGGATACCGT
                                                        HindIII
        \/sa   .         .   Sac -I    .                  .CAAGCTTCTC (SEQ ID NO:21)
         GGAAGAAGCGGAGACAGCGACGAAGAGCTCATCAGAACAGTCAGACTCATCAAGCTTCTC 6034
         CCTTCTTCGCCTCTGTCGCTGCTTCTCGAGTAGTCTTGTCAGTCTGAGTAGTTCGAAGAG TATCAAAGCA----/(SEQ ID NO:66)
TATCAAAGCA    /                                                       6044
ATAGTTTCGT   /
            /
           /
          /
         /
        /
       /     HTX 6044-8378
      /----ACCCACCTCCCAACCCCGAG           .         .         .
              ACCCACCTCCCAACCCCGAGGGGGACCCGACAGGCCCGAAGGAATAGAAGA 8427
              TGGGTGGAGGGTTGGGGCTCCCCTGGGCTGTCCGGGCTTCCTTATCTTCT .         .         .         .   Bam-HI   .
         AGAAGGTGGAGAGAGAGACAGAGACAGATCCATTCGATTAGTGAACGGATCCTTGGCACT 8487
         TCTTCCACCTCTCTCTCTGTCGCTGTCTAGGTAAGCTAATCACTTGCCTAGGAACCGTGA TATCTGGGACGATCTGCGGAGCCTGTGCCTCTTCAGCTACCACCGCTTGAGAGACTTACT 8547
         ATAGACCCTGCTAGACGCCTCGGACACGGAGAAGTCGATGGTGGCGAACTCTCTGAATGA CTTGATTGTAACGAGGATTGTGGAACTTCTGGGACGCAGGGGGTGGGAAGCCCTCAAATA 8607
         GAACTAACATTGCTCCTAACACCTTGAAGACCCTGCGTCCCCCACCCTTCGGGAGTTTAT TTGGTGGAATCTCCTACAGTATTGGAGTCAGGAACTAAAGAATAGTGCTGTTAGCTTGCT 8667
         AACCACCTTAGAGGATGTCATAACCTCAGTCCTTGATTTCTTATCACGACAATCGAACGA
                                        GATTTCTTATCACGACAATCTTAAGA (SEQ ID NO:14)
                                                    HTX 8670
                  .
         CAATGCCACAGCC   (SEQ ID NO:67)                                  8680
         GTTACGGTGTCGG
         GTT
```

The "bridging primer" (HTX 6044-8378, 40 mer) was composed of the sequence 6025–6044 (20 mer) and the sequence 8378–8397 (also 20mer), pointing down towards the 3'-end of HIV genome. Although the "bridging primer" also anneals to the negative strand at the positions of 6025–6044, only when it bound to the position 8378–8397 can the polymerization (elongation) be initiated. Therefore the "bridging primer" pairs with the 3'-end primer (8670–8642) to amplify the fragment from 8378 to 8670 plus 20 base pairs corresponding to the positions 6025–6044, totaling 312 base pairs in length. When there are more 3'-end primer than the "bridging primer", more negative strands (initiated by 3'-end primer) than positive ones (initiated by "bridging primer") are amplified. The negative strands would carry at their 3'-ends the complementary sequence to the "bridging primer." The very 3'-end of these single-stranded DNA would anneal to the positive strands at position 6025–6044 of the original templates or to the single-stranded DNA initiated by the 5'-end primer (5738–5761). As soon as the "bridging primer complementary sequence"-initiated DNA elongation reached the positions 5738–5761, the two fragments are physically linked together. From then on the amplification depends only on two primers annealing to either end of the linked fragment. The events are illustrated as follows:

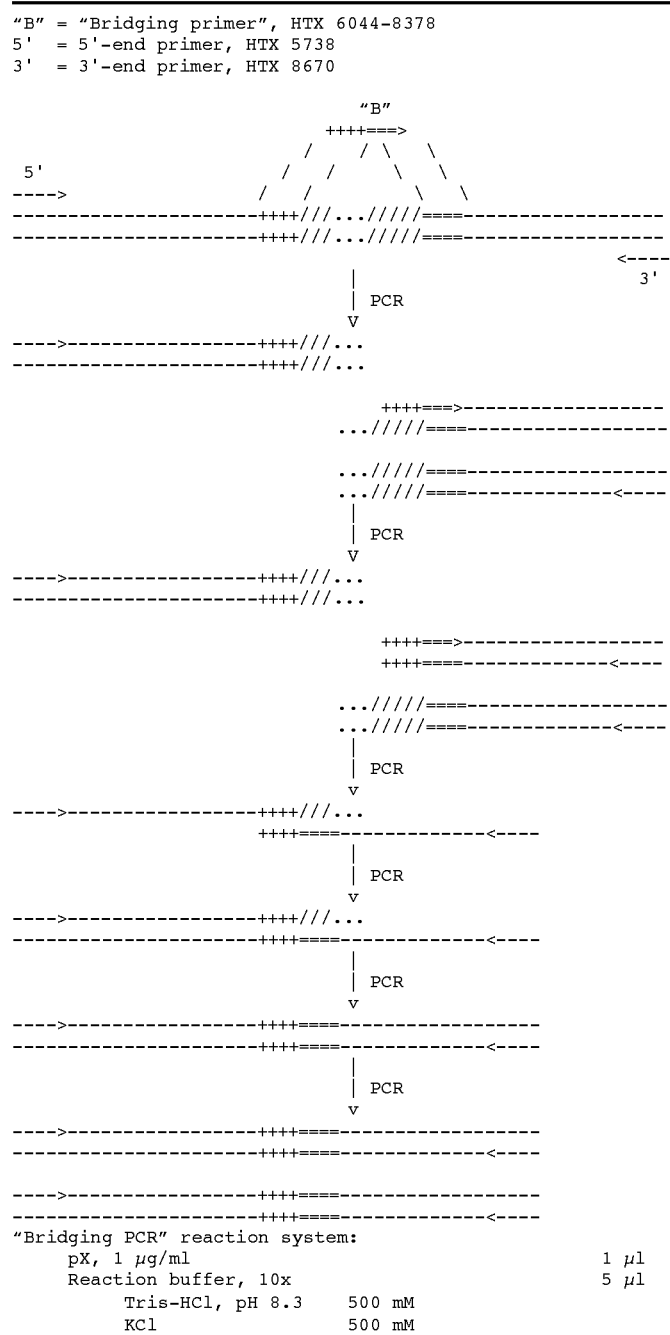

```
"B" = "Bridging primer", HTX 6044-8378
5'  = 5'-end primer, HTX 5738
3'  = 3'-end primer, HTX 8670
```

"Bridging PCR" reaction system:
```
    pX, 1 µg/ml                          1 µl
    Reaction buffer, 10x                 5 µl
        Tris-HCl, pH 8.3    500 mM
        KCl                 500 mM
```

-continued

```
    MgCl2               20 mM
    Gelatine            0.05%
dNTP's, 2.5 mM each                          3 µl
5'-primer, HTX 5738-5761, 60 µg/ml           2 µl
3'-primer, HTX 8670-8642, 60 µg/ml           2 µl
"B"primer, HTX 6044-8378,  6 µg/ml           2 µl
AmpliTaq DNA polymerase, 5 u/µl              0.2 µl
(from Perkin Elmer Cetus)
Double distilled water                      34.8 µl
                                            ─────
                                            50.0 µl
```

The thermal cycling setting was 50 cycles, each consisting of 94° C. for 20 seconds, 54° C. for 20 seconds and 74° C. for 60 seconds.

The amplified fragments would have the sequences 5738–6044 (307 bp) and 8378–8670 (293 bp) linked into one piece (600 bp) containing full-length tat and rev sequences in continuation.

```
              Eco -I              .          .        \/sa    .Sal -I    .
        ATAAGAATTCTGCAACAACTGCTGTTTATCCATTTTCAGAATTGGGTGTCGACATAG          5794
        TATTCTTAAGACGTTGTTGACGTCAAATAGGTAAAAGTCTTAACCCACAGCTGTATC

.            .            .            .            .
        CAGAATAGGCGTTACTCGACAGAGGAGAGCAAGAAATGGAGCCAGTAGATCCTAGACTAG        5854
        GTCTTATCCGCAATGAGCTGTCTCCTCTCGTTCTTTACCTCGGTCATCTAGGATCTGATC

.            .            .            .            .
        AGCCCTGGAAGCATCCAGGAAGTCAGCCTAAAACTGCTTGTACCAATTGCTATTGTAAAA        5914
        TCGGGACCTTCGTAGGTCCTTCAGTCGGATTTTGACGAACATGGTTAACGATAACATTTT

.            .            .            .            .
        AGTGTTGCTTTCATTGCCAAGTTTGTTTCATAACAAAAGCCTTAGGCATCTCCTATGGCA        5974
        TCACAACGAAAGTAACGGTTCAAACAAAGTATTGTTTTCGGAATCCGTAGAGGATACCGT

\/sa        .            .   Sac -I       .         . HindIII .
        GGAAGAAGCGGAGACAGCGACGAAGAGCTCATCAGAACAGTCAGACTCATCAAGCTTCTC        6034
        CCTTCTTCGCCTCTGTCGCTGCTTCTCGAGTAGTCTTGTCAGTCTGAGTAGTTCGAAGAG 6044  8378
              sd\/sa        .            .            .            .
        TATCAAAGCAACCCACCTCCCAACCCCGAGGGGACCCGACAGGCCCGAAGGAATAGAAGA        8427
        ATAGTTTCGTTGGGTGGAGGGTTGGGGCTCCCCTGGGCTGTCCGGGCTTCCTTATCTTCT .            .            .            .      Bam-HI    .
        AGAAGGTGGAGAGAGAGACAGAGACAGATCCATTCGATTAGTGAACGGATCCTTGGCACT        8487
        TCTTCCACCTCTCTCTGTCGCTGTCTAGGTAAGCTAATCACTTGCCTAGGAACCGTGA .            .            .            .            .
        TATCTGGGACGATCTGCGGAGCCTGTGCCTCTTCAGCTACCACCGCTTGAGAGACTTACT        8547
        ATAGACCCTGCTAGACGCCTCGGACACGGAGAAGTCGATGGTGGCGAACTCTCTGAATGA .            .            .            .            .
        CTTGATTGTAACGAGGATTGTGGAACTTCTGGGACGCAGGGGGTGGGAAGCCCTCAAATA        8607
        GAACTAACATTGCTCCTAACACCTTGAAGACCCTGCGTCCCCACCCTTCGGGAGTTTAT .            .            .            .        Eco-RI.
        TTGGTGGAATCTCCTACAGTATTGGAGTCAGGAACTAAAGAATAGTGCTGTTAGAATTCT       8667
        AACCACCTTAGAGGATGTCATAACCTCAGTCCTTGATTTCTTATCACGACAATCTTAAGA CAA                                                                8670
        GTT SEQ ID NO:22 (without coding information)

ATAAGAATTC TGCAACAACT GCTGTTTATC CATTTTCAGA ATTGGGTGTC                50

GACATAGCAG AATAGGCGTT ACTCGACAGA GGAGAGCAAG AAATGGAGCC               100

AGTAGATCCT AGACTAGAGC CTGGAAGCA  TCCAGGAAGT CAGCCTAAAA               150

CTGCTTGTAC CAATTGCTAT TGTAAAAAGT GTTGCTTTCA TTGCCAAGTT               200

TGTTTCATAA CAAAAGCCTT AGGCATCTCC TATGGCAGGA AGAAGCGGAG               250
```

```
                           -continued
ACAGCGACGA AGAGCTCATC AGAACAGTCA GACTCATCAA GCTTCTCTAT           300

CAAAGCAACC CACCTCCCAA CCCCGAGGGG ACCCGACAGG CCCGAAGGAA           350

TAGAAGAAGA AGGTGGAGAG AGAGACAGAG ACAGATCCAT TCGATTAGTG           400

AACGGATCCT TGGCACTTAT CTGGGACGAT CTGCGGAGCC TGTGCCTCTT           450

CAGCTACCAC CGCTTGAGAG ACTTACTCTT GATTGTAACG AGGATTGTGG           500

AACTTCTGGG ACGCAGGGGG TGGGAAGCCC TCAAATATTG GTGGAATCTC           550

CTACAGTATT GGAGTCAGGA ACTAAAGAAT AGTGCTGTTA GAATTCTCAA           600

SEQ ID NO:72 (with TAT protein sequence)

ATAAGAATTC TGCAACAACT GCTGTTTATC CATTTTCAGA ATTGGGTGTC            50

GACATAGCAG AATAGGCGTT ACTCGACAGA GGAGAGCAAG AA ATG GAG CCA       101
                                               Met Glu Pro

GTA GAT CCT AGA CTA GAG CCC TGG AAG CAT CCA GGA AGT CAG CCT      146
Val Asp Pro Arg Leu Glu Pro Trp Lys His Pro Gly Ser Gln Pro
  5              10                  15

AAA ACT GCT TGT ACC AAT TGC TAT TGT AAA AAG TGT TGC TTT CAT      191
Lys Thr Ala Cys Thr Asn Cys Tyr Cys Lys Lys Cys Cys Phe His
 20                  25                  30

TGC CAA GTT TGT TTC ATA ACA AAA GCC TTA GGC ATC TCC TAT GGC      236
Cys Gln Val Cys Phe Ile Thr Lys Ala Leu Gly Ile Ser Tyr Gly
     35                  40                  45

AGG AAG AAG CGG AGA CAG CGA CGA AGA GCT CAT CAG AAC AGT CAG      281
Arg Lys Lys Arg Arg Gln Arg Arg Arg Ala His Gln Asn Ser Gln
 50                  55                  60

ACT CAT CAA GCT TCT CTA TCA AAG CAA CCC ACC TCC CAA CCC CGA      326
Thr His Gln Ala Ser Leu Ser Lys Gln Pro Thr Ser Gln Pro Arg
 65                  70                  75

GGG GAC CCG ACA GGC CCG AAG GAA TAGAAGAAGA AGGTGGAGAG            370
Gly Asp Pro Thr Gly Pro Lys Glu
 80                  85

AGAGACAGAG ACAGATCCAT TCGATTAGTG AACGGATCCT TGGCACTTAT           420

CTGGGACGAT CTGCGGAGCC TGTGCCTCTT CAGCTACCAC CGCTTGAGAG           470

ACTTACTCTT GATTGTAACG AGGATTGTGG AACTTCTGGG ACGCAGGGGG           520

TGGGAAGCCC TCAAATATTG GTGGAATCTC CTACAGTATT GGAGTCAGGA           570

ACTAAAGAAT AGTGCTGTTA GAATTCTCAA                                 600

SEQ ID NO:73 (with REV protein sequence)

ATAAGAATTC TGCAACAACT GCTGTTTATC CATTTTCAGA ATTGGGTGTC            50

GACATAGCAG AATAGGCGTT ACTCGACAGA GGAGAGCAAG AAATGGAGCC           100

AGTAGATCCT AGACTAGAGC CCTGGAAGCA TCCAGGAAGT CAGCCTAAAA           150

CTGCTTGTAC CAATTGCTAT TGTAAAAAGT GTTGCTTTCA TTGCCAAGTT           200

TGTTTCATAA CAAAAGCCTT AGGCATCTCC T ATG GCA GGA AGA AGC GGA       249
                                  Met Ala Gly Arg Ser Gly
                                                        5

GAC AGC GAC GAA GAG CTC ATC AGA ACA GTC AGA CTC ATC AAG CTT      294
Asp Ser Asp Glu Glu Leu Ile Arg Thr Val Arg Leu Ile Lys Leu
         10                  15                  20

CTC TAT CAA AGC AAC CCA CCT CCC AAC CCC GAG GGG ACC CGA CAG      339
Leu Tyr Gln Ser Asn Pro Pro Pro Asn Pro Glu Gly Thr Arg Gln
             25                  30                  35

GCC CGA AGG AAT AGA AGA AGA AGG TGG AGA GAG AGA CAG AGA CAG      384
Ala Arg Arg Asn Arg Arg Arg Arg Trp Arg Glu Arg Gln Arg Gln
             40                  45                  50
```

-continued

```
ATC CAT TCG ATT AGT GAA CGG ATC CTT GGC ACT TAT CTG GGA CGA      429
Ile His Ser Ile Ser Glu Arg Ile Leu Gly Thr Tyr Leu Gly Arg
            55                  60                  65

TCT GCG GAG CCT GTG CCT CTT CAG CTA CCA CCG CTT GAG AGA CTT      474
Ser Ala Glu Pro Val Pro Leu Gln Leu Pro Pro Leu Gln Arg Leu
            70                  75                  80

ACT CTT GAT TGT AAC GAG GAT TGT GGA ACT TCT GGG ACG CAG GGG      519
Thr Leu Asp Cys Asn Glu Asp Cys Gly Thr Ser Gly Thr Gln Gly
            85                  90                  95

GTG GGA AGC CCT CAA ATA TTG GTG GAA TCT CCT ACA GTA TTG GAG      564
Val Gly Ser Pro Gln Ile Leu Val Glu Ser Pro Thr Val Leu Glu
            100                 105                 110

TCA GGA ACT AAA GAA TAGTGCTGTT AGAATTCTCA A                      600
Ser Gly Thr Lys Glu
            115
```

The EcoRI fragment (586 bp) of the PCR product is inserted into Eco RI site of SFneo (see FIG. 5). The recombinant plasmid are screened with Sal-I enzyme digestion. The plasmid without the insert yield a single band of 7227 bps (SFneo only). Plasmid with inserts show two bands, the smaller of which is either 743 bps (insertion in right orientation) or 1247 bps (insertion in wrong orientation). The recombinant plasmid in right orientation, SFneo-t/r(+) (stands for tat/rev positive or sense) is advantageously chosen as the complemental gene expression vector for antisense/ribozyme proviral clones. The one in wrong orientation, "SFneo-t/r(−)" (stands for tat/rev negative or antisense), is used in the experiments of vector-expressed antisense tat-rev RNA inhibition of wild type HIV-1 viruses.

and inactivate the sense tat mRNA from the gene-expression vectors. This potential problem rests on the one-hundred-percent sequence complementation between the tat's in antisense/ribozyme molecular clones and that in the gene expression vectors. If this occurs, there may not be enough TAT protein available for efficient replication of antisense/ribozyme viruses.

Proteins are composed of amino acids which in turn are encoded by nucleotide triplets. The fact that most amino acids (except methionine and tryptophan) are encoded by more than one nucleotide triplet creates the possibility of diversifying nucleotide sequence while keeping the amino acid sequence unchanged for a particular protein.

The following shows one of the diversifications for tat-protein-coding nucleotide sequences. The first line shows t

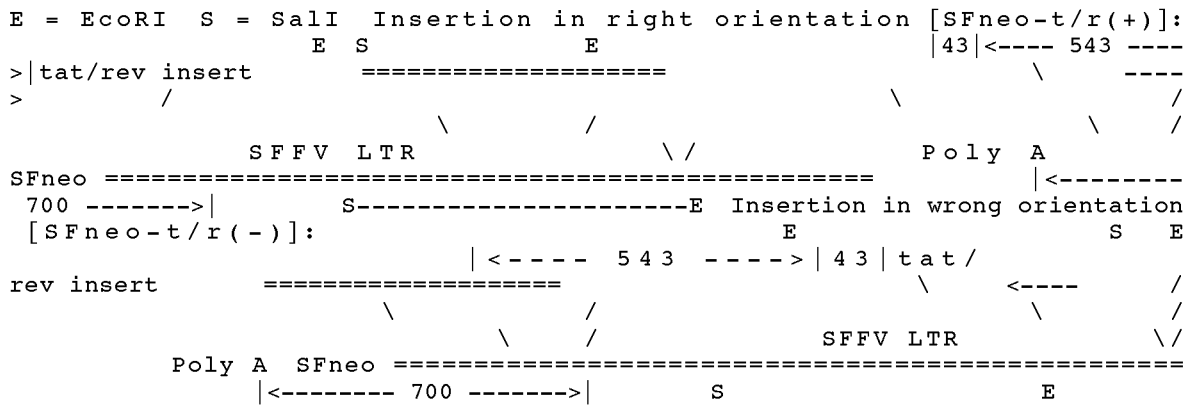

```
E = EcoRI  S = SalI  Insertion in right orientation [SFneo-t/r(+)]:
                     E  S            E                    |43|<---- 543 ----
>|tat/rev insert        ===================                     \      ----
>         /                                           \                   /
                  \        /                                      \     /
             SFFV LTR                \/                  Poly  A
SFneo =====================================================       |<--------
 700 ------->|       S----------------------E  Insertion in wrong orientation
 [SFneo-t/r(-)]:                               E                       S   E
                        |<---- 543 ---->|43|tat/
rev insert      ===================                    \    <----      /
                      \            /                          \         /
                             \     /                 SFFV LTR           \/
          Poly A  SFneo ================================================
                 |<-------- 700 ------->|          S                 E
```

EXAMPLE 7

Construction of TAT-Expression Vectors Containing Containing Chemically Synthesized TAT Encoding Sequence With gene-expression vectors constructed by the above-mentioned protocols, either driven by HIV-1 or another promotor, there exists the possibility that the antisense RNA transcribed from the antisense/ribozyme clones will bind he original tat nucleotide sequence (HXB2); the second the amino acid sequence; and the third the diversification of tat nucleotide sequence. Of the 87 codons, all except two (the initiator methionine and the eleventh residue tryptophan) can be altered at at least one base. 8 arginines and 3 leucines can be changed at two bases. The 7 serines can be changed at all three bases. The stop codon too can be changed at two bases. In total, 111 out of 261 (42.5%) nucleotides can be changed, enough to nullify complementation.

```
ATG GAG CCA GTA GAT CCT AGA CTA GAG CCC TGG AAG CAT CCA GGA AGT
```

```
                     -continued
 M   E   P   V   D   P   R   L   E   P   W   K   H   P   G   S
ATG GAA CCT GTG GAC CCA CGT TTG GAA CCA TGG AAA CAC CCT GGT TCA
 *   *   *   *   * * * * *   *   *       *   *   *   * ***

CAG CCT AAA ACT GCT TGT ACC AAT TGC TAT TGT AAA AAG TGT TGC TTT
 Q   P   K   T   A   C   T   N   C   Y   C   K   K   C   C   F
CAA CCA AAG ACA GCA TGC ACG AAC TGT TAC TGC AAG AAA TGC TGT TTC
 *   *   *   *   *   *   *   *   *   *   *   *   *   *   *   *

CAT TGC CAA GTT TGT TTC ATA ACA AAA GCC TTA GGC ATC TCC TAT GGC
 H   C   Q   V   C   F   I   T   K   A   L   G   I   S   Y   G
CAC TGT CAG GTA TGC TTT ATT ACT AAG GCA CTT GGG ATT AGT TAC GGA
 *   *   *   *   *   *   *   *   *   * * *   *   * ***   *   *

AGG AAG AAG CGG AGA CAG CGA CGA AGA GCT CAT CAG AAC AGT CAG ACT
 R   K   K   R   Q   R   R   R   A   H   Q   N   S   Q   T
CGT AAA AAA AGA CGT CAA AGG AGG CGT GCA CAC CAA AAT TCA CAA ACA
 * *   *   * * * * *   * * * * * * *   *   *   *   * ***   *   *

CAT CAA GCT TCT CTA TCA AAG CAA CCC ACC TCC CAA TCC CGA GGG GAC
 H   Q   A   S   L   S   K   Q | P   T   S   Q   S   R   G   D
CAC CAG GCA AGC TTG AGT AAA CAG CCG ACG AGT CAG AGT AGG GGC GAT
 *   *   * *** * * ***   *   *   * * *   * *** * * * *   *   *

CCG ACA GGC CCG AAG GAA TAG (SEQ ID NO:68)
 P   T   G   P   K   E   *
CCT ACT GGG CCC AAA GAG TGA (SEQ ID NO:69)
 *   *   *   *   *   * **
```

Since the expression vectors will also be utilized for the production of antisense-ribozyme viruses (ARV), care has been taken to nullify the potential ribozyme target sites, in order to avoid the binding of diversified tat mRNA by ribozymes expressed by the ARVs.

Removing the original nucleotide sequence:

```
 M   E   P   V   D   P   R   L   E   P   W   K   H   P   G   S
ATG GAA CCT GTG GAC CCA CGT TTG GAA CCA TGG AAA CAC CCT GGT TCA

Q   P   K   T   A   C   T   N   C   Y   C   K   K   C   C   F
CAA CCA AAG ACA GCA TGC ACG AAC TGT TAC TGC AAG AAA TGC TGT TTC

H   C   Q   V   C   F   I   T   K   A   L   G   I   S   Y   G
CAC TGT CAG GTA TGC TTT ATT ACT AAG GCA CTT GGG ATT AGT TAC GGA

R   K   K   R   Q   R   R   R   A   H   Q   N   S   Q   T
CGT AAA AAA AGA CGT CAA AGG AGG CGT GCA CAC CAA AAT TCA CAA ACA

H   Q   A   S   L   S   K   Q | P   T   S   Q   S   R   G   D
CAC CAG GCA AGC TTG AGT AAA CAG CCG ACG AGT CAG AGT AGG GGC GAT

P   T   G   P   K   E   *
CCT ACT GGG CCC AAA GAG TGA (SEQ ID NO:69)
```

Removing the amino acid sequence as well. This is the diversified HIV-1 tat gene to be synthesized chemically.

```
ATG GAA CCT GTG GAC CCA CGT TTG GAA CCA TGG AAA CAC CCT GGT TCA

CAA CCA AAG ACA GCA TGC ACG AAC TGT TAC TGC AAG AAA TGC TGT TTC

CAC TGT CAG GTA TGC TTT ATT ACT AAG GCA CTT GGG ATT AGT TAC GGA

CGT AAA AAA AGA CGT CAA AGG AGG CGT GCA CAC CAA AAT TCA CAA ACA

CAC CAG GCA AGC TTG AGT AAA CAG CCG ACG AGT CAG AGT AGG GGC GAT

CCT ACT GGG CCC AAA GAG TGA (SEQ ID NO: 69)
```

To facilitate the post-synthesis gene construction, to each end was added a 12-base tail which contains an EcoRI restriction enzyme site:

```
                                         GTC GGA ATT CAC
ATG GAA CCT GTG GAC CCA CGT TTG GAA CCA TGG AAA CAC CCT GGT TCA

CAA CCA AAG ACA GCA TGC ACG AAC TGT TAC TGC AAG AAA TGC TGT TTC

CAC TGT CAG GTA TGC TTT ATT ACT AAG GCA CTT GGG ATT AGT TAC GGA

CGT AAA AAA AGA CGT CAA AGG AGG CGT GCA CAC CAA AAT TCA CAA ACA

CAC CAG GCA AGC TTG AGT AAA CAG CCG ACG AGT CAG AGT AGG GGC GAT

CCT ACT GGG CCC AAA GAG TGA CAG AAT TCC GAG   (SEQ ID NO:23)
```

This is the whole artificial gene of diversification to be synthesized chemically.

```
GTCGGAATTC AC ATG GAA CCT GTG GAC CCA CGT TTG GAA CCA TGG       45  SEQ ID NO:23
              Met Glu Pro Val As

```
         Apa-I                    Eco-RI
CCT ACT GGG CCC AAA GAG TGA CAG AAT TCC GAG (SEQ ID NO:23)
GGA TGA CCC GGG TTT CTC ACT GTC TTA AGG CTC
```

For the effectiveness of the synthesis, the whole fragment totaling 285 base pairs is broken down and synthesized as six oligonucleotides, each has a 15-base overlap with the adjacent oligonucleotides, because the middle oligo overlap with two other oligos.

```
1. GTCGGAATTCACATGGAACCTGTGGACCCACGTTTGGAACCATGGAAACACCCTGGTTCA
2. ACAGCATTTCTTGCAGTAACAGTTCGTGCATGCTGTCTTTGGTTGTGAACCAGGGTGTTT
3. TGCAAGAAATGCTGTTTCCACTGTCAGGTATGCTTTATTACTAAGGCACTTGGGATTAGT
4. ATTTTGGTGTGCACGCCTCCTTTGACGTCTTTTTTTACGTCCGTAACTAATCCCAAGTGC
5. CGTGCACACCAAAATTCACAAACACACCAGGCAAGCTTGAGTAAACAGCCGACGAGTCAG
6. CTCGGAATTCTGTCACTCTTTGGGCCCAGTAGCATCGCCCCTACTCTGACTCGTCGGCTG

SEQ ID NO:24 (#1)
GTCGGAATTC ACATGGAACC TGTGGACCCA CGTTTGGAAC CATGGAAACA       50

CCCTGGTTCA                                                   60

SEQ ID NO:25 (#2)
ACAGCATTTC TTGCAGTAAC AGTTCGTGCA TGCTGTCTTT GGTTGTGAAC       50

CAGGGTGTTT                                                   60

SEQ ID NO:26 (#3)
TGCAAGAAAT GCTGTTTCCA CTGTCAGGTA TGCTTTATTA CTAAGGCACT       50

TGGGATTAGT                                                   60

SEQ ID NO:27 (#4)
ATTTTGGTGT GCACGCCTCC TTTGACGTCT TTTTTTACGT CCGTAACTAA       50

TCCCAAGTGC                                                   60

SEQ ID NO:28 (#5)
CGTGCACACC AAAATTCACA AACACACCAG GCAAGCTTGA GTAAACAGCC       50

GACGAGTCAG                                                   60

SEQ ID NO:29 (#6)
CTCGGAATTC TGTCACTCTT TGGGCCCAGT AGCATCGCCC CTACTCTGAC       50

TCGTCGGCTG                                                   60
```

The corresponding positions of the oligonucleotides are shown in bold-type or underlined in the sequence below. Also shown are the overlapping areas of the adjacent oligonucleotides.

```
                                            GTC GGA ATT CAC
                                            CAG CCT TAA GTG

1-->
ATG GAA CCT GTG GAC CCA CGT TTG GAA CCA TGG AAA CAC CCT GGT TCA
TAC CTT GGA CAC CTG GGT GCA AAC CTT GGT ACC TTT GTG GGA CCA AGT
                                              <--2

CAA CCA AAG ACA GCA TGC ACG AAC TGT TAC TGC AAG AAA TGC TGT TTC
GTT GGT TTC TGT CGT ACG TGC TTG ACA ATG ACG TTC TTT ACG ACA AAG

3-->
CAC TGT CAG GTA TGC TTT ATT ACT AAG GCA CTT GGG ATT AGT TAC GGA
GTG ACA GTC CAT ACG AAA TAA TGA TTC CGT GAA CCC TAA TCA ATG CCT
                                    <--4

CGT AAA AAA AGA CGT CAA AGG AGG CGT GCA CAC CAA AAT TCA CAA ACA
GCA TTT TTT TCT GCA GTT TCC TCC GCA CGT GTG GTT TAA AGT GTT TGT
```

```
                                                                  5-->
CAC CAG GCA AGC TTG AGT AAA CAG CCG ACG AGT CAG AGT AGG GGC GAT
GTG GTC CGT TCG AAC TCA TTT GTC GGC TGC TCA GTC TCA TCC CCG CTA
                                <--6

CCT ACT GGG CCC AAA GAG TGA CAG AAT TCC GAG    (SEQ ID NO:23)
GGA TGA CCC GGG TTT CTC ACT GTC TTA AGG CTC
```

The oligonucleotides, each with a 15-base overlap with the adjacent oligonucleotide, were linked into the full-length DNA fragment of 285 bps. All the oligonucleotides were mixed together, with the first and the last ones (numbers 1 & 6) added in amounts ten times as much as the others. In the presence of dNTP's and TaqI DNA polymerase, the mixture underwent thermal cycling just as in an ordinary PCR reaction. By priming to each other, the oligonucleotides were linked together and amplified, as shown below:

The full-length fragment to be made:
----------------------------------------------------------------------
----------------------------------------------------------------------

Chemically synthesized single stranded oligonucleotides, arrows point from 5' to 3':

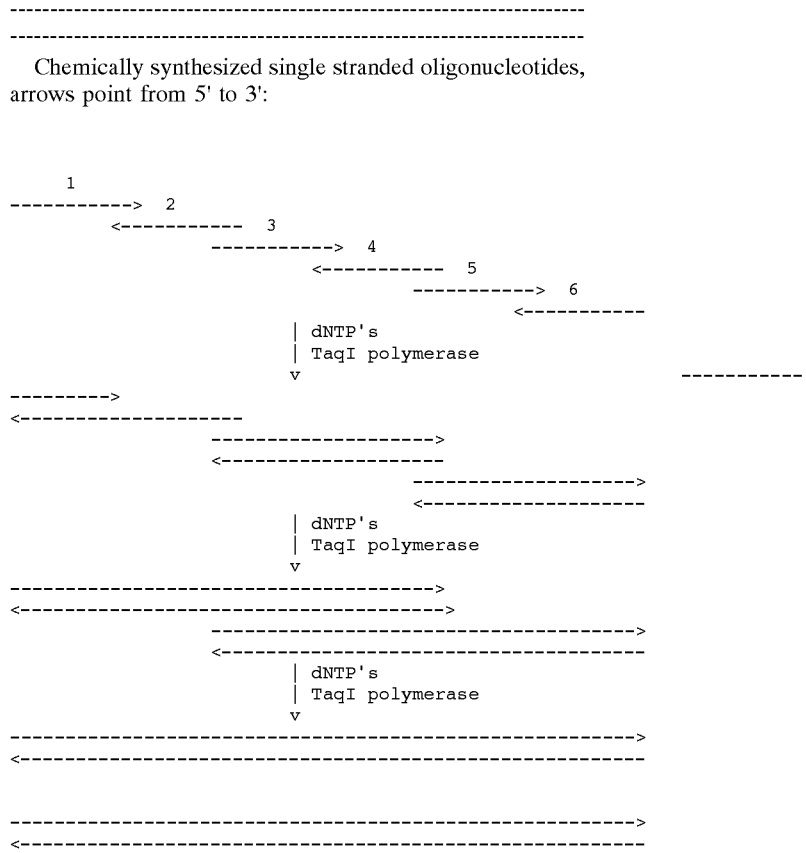

Figure 7:
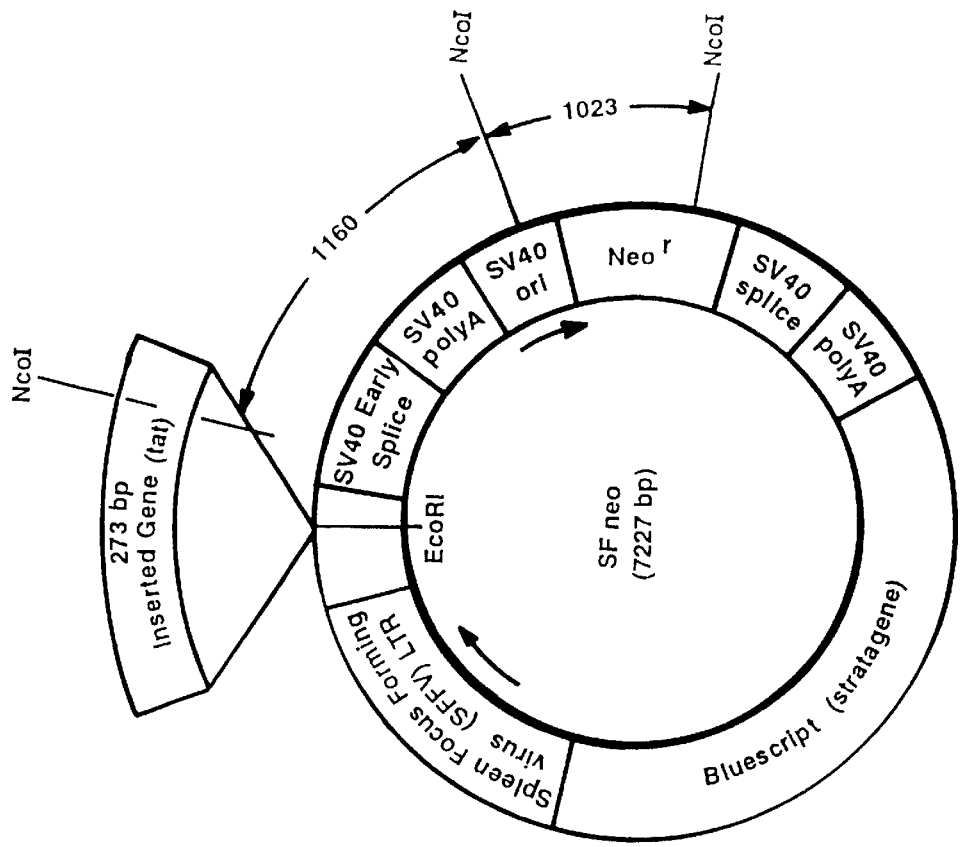
Figure 7:
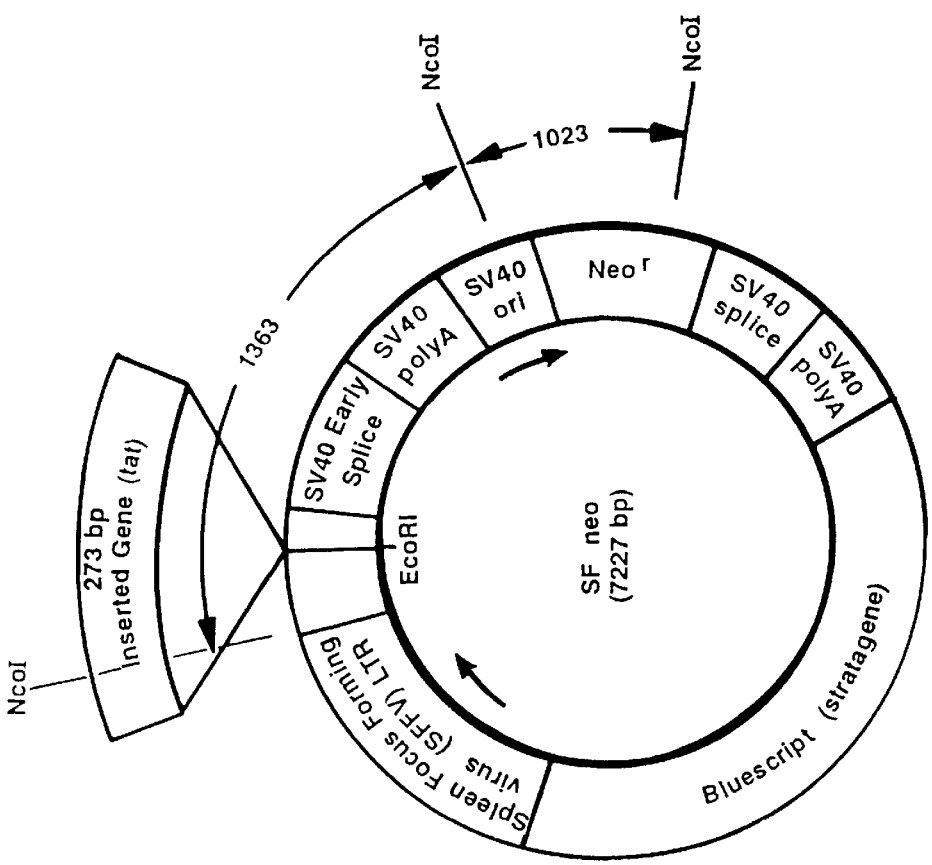

The reaction product was cleaved with EcoRI and the 273 bp fragment inserted into SFneo at EcoRI site. The recombinant clones were screened with NcoI restriction enzyme digestion. Clones without insertions (SFneo per se) yield two bands of 6024 and 1023 bps respectively. Clones with insertions have three bands which are either 5114, 1363 and 1023 bps [insertion in right orientation, "SFneo-tat(+)"] or 5317, 1160 and 1023 bps [insertion in wrong orientation, "SFneo-tat(−)"]. See FIG. 7.

Similarly, the coding sequence for HIV-1 rev can also be diversified:

The original HIV-1 IIIB rev nucleotide and amino acid sequences, is shown below. Note the splice junction site at 26th codon.

```
ATG GCA GGA AGA AGC GGA GAC AGC GAC GAA GAG CTC   (SEQ ID NO:70)
 M   A   G   R   S   G   D   S   D   E   E   L
```

```
                                       sd\/sa
ATC AGA ACA GTC AGA CTC ATC AAG CTT CTC TAT CAA AGC AAC CCA CCT
 I   R   T   V   R   L   I   K   L   L   Y   Q   S   N   P   P

CCC AAC CCC GAG GGG ACC CGA CAG GCC CGA AGG AAT AGA AGA AGA AGG
 P   N   P   E   G   T   R   Q   A   R   R   N   R   R   R   R

TGG AGA GAG AGA CAG AGA CAG ATC CAT TCG ATT AGT GAA CGG ATC CTT
 W   R   E   R   Q   R   Q   I   H   S   I   S   E   R   I   L

GGC ACT TAT CTG GGA CGA TCT GCG GAG CCT GTG CCT CTT CAG CTA CCA
 G   T   Y   L   G   R   S   A   E   P   V   P   L   Q   L   P

CCG CTT GAG AGA CTT ACT CTT GAT TGT AAC GAG GAT TGT GGA ACT TCT
 P   L   E   R   L   T   L   D   C   N   E   D   C   G   T   S

GGG ACG CAG GGG GTG GGA AGC CCT CAA ATA TTG GTG GAA TCT CCT ACA
 G   T   Q   G   V   G   S   P   Q   I   L   V   E   S   P   T

GTA TTG GAG TCA GGA ACT AAA GAA TAG
 V   L   E   S   G   T   K   E   *
```

Keeping the amino acid sequence unchanged, the nucleotide sequence can be diversified at points marked by stars:

```
                ATG GCA GGA AGA AGC GGA GAC AGC GAC GAA GAG CTC   (SEQ ID NO:71)
                 M   A   G   R   S   G   D   S   D   E   E   L
                ATG GCT GGT CGT TCG GGT GAT TCG GAT GAG GAA TTG

```
                                      -continued
ATA CGT ACT GTG CGT TTG ATA AAA TTA TTG TAC CAG TCG AAT CCT CCG
 *  *  *   *   *  *  *  *  *   *   *   *   *   *   *   *

P   N   P   E   G   T   R   Q   A   R   R   N   R   R   R   R
CCT AAT CCT GAA GGT ACG AGG CAA GCT AGG CGT AAC CGT CGA CGG CGC
 *   *   *   *   *   *  *   *   *  *   *   *   *   *   *   *

W   R   E   R   Q   R   Q   I   H   S   I   S   E   R   I   L
TGG CGT GAA CGT CAA CGT CAA ATA CAC AGC ATC TCA GAG AGA ATA TTA
 * *    *  *   *  *   *   *   *  ***   *  ***   * *   *   * *

G   T   Y   L   G   R   S   A   E   P   V   P   L   Q   L   P
GGG ACA TAC TTA GGT AGG AGC GCC GAA CCA GTC CCA TTA CAA TTG CCT
 *  *   *  *   *  *  ***  *   *   *   *  *  *   *  *   *

P   L   E   R   L   T   L   D   C   N   E   D   C   G   T   S
CCT TTG GAA CGT TTG ACA TTA GAC TGC AAT GAA GAC TGC GGT ACA AGC
 * *   *  *  *   *  *   *   *   *   *   *   *   *   *  ***

G   T   Q   G   V   G   S   P   Q   I   L   V   E   S   P   T
GGT ACC CAA GGT GTC GGT TCG CCA CAG ATC CTA GTC GAG AGC CCA ACT
 *  *   *   *   *  *  ***   *   *  *  *   *   *  ***   *   *

V   L   E   S   G   T   K   E   *
GGT CTT GAA AGT GGT ACA AAG GAG TGA
 * *    *  ***   *   *   *   *  **
```

Removing the amino acid sequence as well:

```
            ATG GCT GGT CGT TCG GGT GAT TCG GAT GAG GAA TTG  (SEQ ID NO:71)
             *  * * ***  *  ***   *   * *   *  *
ATA CGT ACT GTG CGT TTG ATA AAA TTA TTG TAC CAG TCG AAT CCT CCG
 *  *  *   *   *  *  *  *  *   *   *   *   *   *   *   *

CCT AAT CCT GAA GGT ACG AGG CAA GCT AGG CGT AAC CGT CGA CGG CGC
 *   *   *   *   *   *  *   *   *  *   *   *   *   *   *   *

TGG CGT GAA CGT CAA CGT CAA ATA CAC AGC ATC TCA GAG AGA ATA TTA
 * *    *  *   *  *   *   *   *  ***   *  ***   * *   *   * *

GGG ACA TAC TTA GGT AGG AGC GCC GAA CCA GTC CCA TTA CAA TTG CCT
 *  *   *  *   *  *  ***  *   *   *   *  *  *   *  *   *

CCT TTG GAA CGT TTG ACA TTA GAC TGC AAT GAA GAC TGC GGT ACA AGC
 * *   *  *  *   *  *   *   *   *   *   *   *   *   *  ***

GGT ACC CAA GGT GTC GGT TCG CCA CAG ATC CTA GTC GAG AGC CCA ACT
 *  *   *   *   *  *  ***   *   *  *  *   *   *  ***   *   *

GTT CTT GAA AGT GGT ACA AAG GAG TGA
 * *    *  ***   *   *   *   *  **
```

Removing the stars:

```
            ATG GCT GGT CGT TCG GGT GAT TCG GAT GAG GAA TTG  (SEQ ID NO:71)
ATA CGT ACT GTG CGT TTG ATA AAA TTA TTG TAC CAG TCG AAT CCT CCG
CCT AAT CCT GAA GGT ACG AGG CAA GCT AGG CGT AAC CGT CGA CGG CGC
TGG CGT GAA CGT CAA CGT CAA ATA CAC AGC ATC TCA GAG AGA ATA TTA
GGG ACA TAC TTA GGT AGG AGC GCC GAA CCA GTC CCA TTA CAA TTG CCT
CCT TTG GAA CGT TTG ACA TTA GAC TGC AAT GAA GAC TGC GGT ACA AGC
GGT ACC CAA GGT GTC GGT TCG CCA CAG ATC CTA GTC GAG AGC CCA ACT
GTT CTT GAA AGT GGT ACA AAG GAG TGA
```

Adding to each end a 12 basepair tail carrying an Eco RI site:

```
GAC TGA ATT CAT ATG GCT GGT CGT TCG GGT GAT TCG GAT GAG GAA TTG    (SEQ ID NO:30)

ATA CGT ACT GTG CGT TTG ATA AAA TTA TTG TAC CAG TCG AAT CCT CCG

CCT AAT CCT GAA GGT ACG AGG CAA GCT AGG CGT AAC CGT CGA CGG CGC

TGG CGT GAA CGT CAA CGT CAA ATA CAC AGC ATC TCA GAG AGA ATA TTA

GGG ACA TYA TTA GGT AGG AGC GCC GAA CCA GTC CCA TTA CAA TTG CCT

CCT TTG GAA CGT TTG ACA TTA GAC TGC AAT GAA GAC TGC GGT ACA AGC

GGT ACC CAA GGT GTC GGT TCG CCA CAG ATC CTA GTC GAG AGC CCA ACT

GTT CTT GAA AGT GGT ACA AAG GAG TGA TCG AAT TCC GTC
                                                    15
```

Adding the complementary strand:

```
    Eco-RI Nde-I                                                   (SEQ ID NO:30)
GAC TGA ATT CAT ATG GCT GGT CGT TCG GGT GAT TCG GAT GAG GAA TTG
CTC ACT TAA GTA TAC CGA CCA GCA AGC CCA CTA AGC CTA CTC CTT AAC

ATA CGT ACT GTG CGT TTG ATA AAA TTA TTG TAC CAG TCG AAT CCT CCG
TAT GCA TGA CAC GCA AAC TAT TTT AAT AAC ATG GTC AGC TTA GGA GGC

S a l -I
CCT AAT CCT GAA GGT ACG AGG CAA GCT AGG CGT AAC CGT CGA CGG CGC
GGA TTA GGA CTT CCA TGC TCC GTT CGA TCC CGA TTG GCA GCT GCC GCG

TGG CGT GAA CGT CAA CGT CAA ATA CAC AGC ATC TCA GAG AGA ATA TTA
ACC GCA CTT GCA GTT GCA GTT TAT GTG TCG TAG AGT CTC TCT TAT AAT

GGG ACA TAC TTA GGT AGG AGC GCC GAA CCA GTC CCA TTA CAA TTG CCT
CCC TGT ATG AAT CCA TCC TCG CGG CTT GGT CAG GGT AAT GTT AAC GGA

CCT TTG GAA CGT TTG ACA TTA GAC TGC AAT GAA GAC TGC GGT ACA AGC
GGA AAC CTT GCA AAC TGT AAT CTG ACG TTA CTT CTG ACG CCA TGT TCG

GGT ACC CAA GGT GTC GGT TCG CCA CAG ATC CTA GTC GAG AGC CCA ACT
CCA TGG GTT CCA CAG CCA AGC GGT GTC TAG GAT CAG CTC TCG GGT TGA

Eco-RI
GTT CTT GAA AGT GGT ACA AAG GAG TGA TCG AAT TCC GTC
CAA GAA CTT TCA CCA TGT TTC CTC ACG AGC TTA AGG CAG
```

To synthesize this fragment, eight (8) oligonucleotides are needed. The positions of the oligonucleotide primers are shown in bold-type characters or underlined with numbering and arrows pointing to their 3' ends:

```
    Eco-RI Nde-I                                                   (SEQ ID NO:30)
GAC TGA ATT CAT-ATG GCT GGT CGT TCG GGT GAT TCG GAT GAG GAA TTG
CTC ACT TAA GTA-TAC CGA CCA GCA AGC CCA CTA AGC CTA CTC CTT AAC

1-->
ATA CGT ACT GTG CGT TTG ATA AAA TTA TTG TAC CAG TCG AAT CCT CCG
TAT GCA TGA CAC GCA AAC TAT TTT AAT AAC ATG GTC AGC TTA GGA GGC
<--2

S a l -I
CCT AAT CCT GAA GGT ACG AGG CAA GCT AGG CGT AAC CGT CGA CGG CGC
GGA TTA GGA CTT CCA TGC TCC GTT CGA TCC GCA TTG GCA GCT GCC GCG

3-->
TGG CGT GAA CGT CAA CGT CAA ATA CAC AGC ATC TCA GAG AGA ATA TTA
ACC GCA CTT GCA GTT GCA GTT TAT GTG TCG TAG AGT CTC TCT TAT AAT
<--4

GGG ACA TAC TTA GGT AGG AGC GCC GAA CCA GTC CCA TTA CAA TTG CCT
CCC TGT ATG AAT CCA TCC TCG CGG CTT GGT CAG GGT AAT GTT AAC GGA

5-->
```

```
-continued
CCT TTG GAA CGT TTG ACA TTA GAC TGC AAT GAA GAC TGC GGT ACA AGC
GGA AAC CTT GCA AAC TGT AAT CTG ACG TTA CTT CTG ACG CCA TGT TCG
<--6

GGT ACC CAA GGT GTC GGT TCG CCA CAG ATC CTA GTC GAG AGC CCA ACT
CCA TGG GTT CCA CAG CCA AGC CGT GTC TAG GAT CAG CTC TCG GGT TGA

7-->                         Eco-RI
GTT CTT GAA AGT GGT ACA AAG GAG TGA-TCG AAT TCC GTC
CAA GAA CTT TCA CCA TGT TTC CTC ACG-AGC TTA AGG CAG
<--8
```

SEQ ID NO:30 (diversified rev DNA sequence with protein)

```
GACTGAATTC AT ATG GCT GGT CGT TCG GGT GAT TCG GAT GAG GAA     45
          Met Ala Gly Arg Ser Gly Asp Ser Asp Glu Glu
                        5                       10

TTG ATA CGT ACT GTG CGT TTG ATA AAA TTA TTG TAC CAG TCG AAT    90
Leu Ile Arg Thr Val Arg Leu Ile Lys Leu Leu Tyr Gln Ser Asn
             15                  20                  25

CCT CCG CCT AAT CCT GAA GGT ACG AGG CAA GCT AGG CGT AAC CGT   135
Pro Pro Pro Asn Pro Glu Gly Thr Arg Gln Ala Arg Arg Asn Arg
             30                  35                  40

CGA CGG CGC TGG CGT GAA CGT CAA CGT CAA ATA CAC AGC ATC TCA   180
Arg Arg Arg Trp Arg Glu Arg Gln Arg Gln Ile His Ser Ile Ser
             45                  50                  55

GAG AGA ATA TTA GGG ACA TAC TTA GGT AGG AGC GCC GAA CCA GTC   225
Glu Arg Ile Leu Gly Thr Tyr Leu Gly Arg Ser Ala Glu Pro Val
             60                  65                  70

CCA TTA CAA TTG CCT CCT TTG GAA CGT TTG ACA TTA GAC TGC AAT   270
Pro Leu Gln Leu Pro Pro Leu Glu Arg Leu Thr Leu Asp Cys Asn
             75                  80                  85

GAA GAC TGC GGT ACA AGC GGT ACC CAA GGT GTC GGT TCG CCA CAG   315
Glu Asp Cys Gly Thr Ser Gly Thr Gln Gly Val Gly Ser Pro Gln
             90                  95                 100

ATC CTA GTC GAG AGC CCA ACT GTT CTT GAA AGT GGT ACA AAG GAG   360
Ile Leu Val Glu Ser Pro Thr Val Leu Glu Ser Gly Thr Lys Glu
            105                 110                 115

TGATCGAATT CCGTC                                              375
```

Oligonucleotide primers needed to synthesize SEQ ID NO:30

SEQ ID NO:31 (#1)

```
GACTGAATTC ATATGGCTGG TCGTTCGGGT GATTCGGATG AGGAATTGAT      50
ACGTACTGTG CGT                                              63
```

SEQ ID NO:32 (#2)

```
ACCTTCAGGA TTAGGCGGAG GATTCGACTG GTACAATAAT TTTATCAAAC      50
GCACAGTACG TAT                                              63
```

SEQ NO ID:33 (#3)

```
CCTAATCCTG AAGGTACGAG GCAAGCTAGG CGTAACCGTC GACGGCGCTG      50
GCGTGAACGT CAA                                              63
```

SEQ NO ID:34 (#4)

```
ACCTAAGTAT GTCCCTAATA TTCTCTCTGA GATGCTGTGT ATTTGACGTT      50
GACGTTCACG CCA                                              63
```

SEQ ID NO:35 (#5)

```
GGGACATACT TAGGTAGGAG CGCCGAACCA GTCCCATTAC AATTGCCTCC      50
```

-continued

```
TTTGGAACGT TTG                                                     63

SEQ ID NO:36 (#6)

GACACCTTGG GTACCGCTTG TACCGCAGTC TTCATTGCAG TCTAATGTCA              50

AACGTTCCAA AGG                                                     63

SEQ ID NO:37 (#7)

GGTACCCAAG GTGTCGGTTC GCCACAGATC CTAGTCGAGA GCCCAACTGT              50

TCTTGAAAGT GGT                                                     63

SEQ ID NO:38 (#8)

GACGGAATTC GAGCACTCCT TTGTACCACT TTCAAGAAC                         39
```

EXAMPLE 8

Co-Transfection Experiments

Transfection of pXE (or pX), pXE-a, pXE-b, pXE-ar and pXE-br into a cell line optionally transfected with one of the tat-expression vectors tat-neo or with neo-only control, the viral production, infectivity and viral replication upon infection with or without further TAT complementation is as follows:

| Transfection | | Virion | Virion | Viral Replication Upon infection of | |
|---|---|---|---|---|---|
| 1st | 2nd | Production | Infectivity | CD4+ Cells | CD4+/Tat+ Cells |
| (1) none | none | No | No | No | No |
| (2) none | pXE | Yes | Yes | Yes | Yes |
| (3) none | pXE-a | No | No | No | No |
| (4) none | pXE-b | No | No | No | No |
| (5) none | pXE-ar | No | No | No | No |
| (6) none | pXE-br | No | No | No | No |
| (7) -neo | none | No | No | No | No |
| (8) -neo | pXE | Yes | Yes | Yes | Yes |
| (9) -neo | pXE-a | No | No | No | No |
| (10) -neo | pXE-b | No | No | No | No |
| (11) -neo | pXE-ar | No | No | No | No |
| (12) -neo | pXE-br | No | No | No | No |
| (13) tat-neo | none | No | No | No | No |
| (14) tat-neo | pXE | Yes | Yes | Yes | Yes |
| (15) tat-neo | pXE-a | Yes | Yes | No | Yes |
| (16) tat-neo | pXE-b | Yes | Yes | No | Yes |
| (17) tat-neo | pXE-ar | Yes | Yes | No | Yes |
| (18) tat-neo | pXE-br | Yes | Yes | No | Yes |

Virus Co-Infection Experiments

When supernatant from different transfections (numbered as in the above table) are collected and the combination is used to infect CD4+ cell line, the results are as follows:

|    | 1 | 2 | 3 | 4 | 5 | 6 | 7 | 8 | 9 | 10 | 11 | 12 | 13 | 14 | 15 | 16 | 17 | 18 |
|----|---|---|---|---|---|---|---|---|---|----|----|----|----|----|----|----|----|----|
| 1  | − | + | − | − | − | − | − | + | − | −  | −  | −  | −  | +  | −  | −  | −  | −  |
| 2  | + | + | + | + | + | + | + | + | + | +  | +  | +  | +  | +  | +  | +  | +  | +  |
| 3  | − | + | − | − | − | − | − | + | − | −  | −  | −  | −  | +  | −  | −  | −  | −  |
| 4  | − | + | − | − | − | − | − | + | − | −  | −  | −  | −  | +  | −  | −  | −  | −  |
| 5  | − | + | − | − | − | − | − | + | − | −  | −  | −  | −  | +  | −  | −  | −  | −  |
| 6  | − | + | − | − | − | − | − | + | − | −  | −  | −  | −  | +  | −  | −  | −  | −  |
| 7  | − | + | − | − | − | − | − | + | − | −  | −  | −  | −  | +  | −  | −  | −  | −  |
| 8  | + | + | + | + | + | + | + | + | + | +  | +  | +  | +  | +  | +  | +  | +  | +  |
| 9  | − | + | − | − | − | − | − | + | − | −  | −  | −  | −  | +  | −  | −  | −  | −  |
| 10 | − | + | − | − | − | − | − | + | − | −  | −  | −  | −  | +  | −  | −  | −  | −  |
| 11 | − | + | − | − | − | − | − | + | − | −  | −  | −  | −  | +  | −  | −  | −  | −  |
| 12 | − | + | − | − | − | − | − | + | − | −  | −  | −  | −  | +  | −  | −  | −  | −  |
| 13 | − | + | − | − | − | − | − | + | − | −  | −  | −  | −  | +  | −  | −  | −  | −  |
| 14 | + | + | + | + | + | + | + | + | + | +  | +  | +  | +  | +  | +  | +  | +  | +  |
| 15 | − | ± | − | − | − | − | − | ± | − | −  | −  | −  | −  | ±  | −  | −  | −  | −  |
| 16 | − | ± | − | − | − | − | − | ± | − | −  | −  | −  | −  | ±  | −  | −  | −  | −  |
| 17 | − | ± | − | − | − | − | − | ± | − | −  | −  | −  | −  | ±  | −  | −  | −  | −  |
| 18 | − | ± | − | − | − | − | − | ± | − | −  | −  | −  | −  | ±  | −  | −  | −  | −  |

+ Virus particles are produced;
− Virus particles are not produced;
± Virus particles are produced transiently.

While the present invention has been described in terms of preferred embodiments, it is understood that variations and modifications will occur to those skilled in the art. Therefore, it is intended that the appended claims cover all such equivalent variations which come within the scope of the invention as claimed.

The features disclosed in the foregoing description, in the following claims and/or in the accompanying drawings may, both separately and in any combination thereof, be material for realizing the invention in diverse forms thereof.

What is claimed is:

1. An HIV antisense virus comprising:
a viral coat the same as the viral coat of an HIV virus, and nucleic acid including an antisense fragment which is antisense to a section of a gene encoding a transactivating protein required for said HIV virus to replicate, said antisense fragment encoding antisense RNA which binds and inactivates mRNA encoded by said gene encoding a transactivating protein.

2. An antisense virus as in claim 1 wherein said antisense virus is replication defective.

3. An antisense virus as in claim 1 wherein said nucleic acid includes all of the structural genes of said HIV virus.

4. An antisense virus as in claim 1 wherein said nucleic acid includes all of the regulatory genes of said HIV virus except said gene encoding a transactivating protein.

5. An antisense virus as in claim 1 wherein except for said antisense fragment which encodes antisense RNA, said antisense virus is the same as said HIV virus.

6. An antisense virus as in claim 1 wherein said HIV virus is selected from the group consisting of HIV-1, HIV-2.

7. The antisense virus as in claim 6 wherein said antisense fragment which encodes antisense RNA is a section of a gene selected from the group consisting of tat, rev and vpr, which has been turned antisense.

8. An antisense virus as in claim 6 wherein said mRNA is an mRNA encoded by a gene selected from the group consisting of tat, rev, and vpr.

9. An antisense proviral molecular clone including
structural genes of an HIV virus, and
an antisense fragment which is antisense to a section of a gene encoding a transactivating protein required for said HIV virus to replicate, said antisense fragment encoding antisense RNA and mRNA encoded by said gene encoding a transactivating protein.

10. A method of synthesizing an antisense proviral molecular clone comprising the steps of:

a) inserting DNA encoding an HIV virus into a vector; and b) creating an antisense fragment in said DNA by turning antisense a section of a gene of said DNA, said gene encoding a transactivating protein required for said HIV virus to replicate, said antisense fragment encoding antisense RNA mRNA encoded by said gene encoding a transactivating protein.

11. A method as in claim 10 wherein said vector is a plasmid.

* * * * *